United States Patent
Shih et al.

(10) Patent No.: US 10,633,449 B2
(45) Date of Patent: Apr. 28, 2020

(54) TREATMENT AND REVERSAL OF FIBROSIS AND INFLAMMATION BY INHIBITION OF THE TL1A-DR3 SIGNALING PATHWAY

(71) Applicant: Cedars-Sinai Medical Center, Los Angeles, CA (US)

(72) Inventors: David Q. Shih, La Crescenta, CA (US); Stephan R. Targan, Santa Monica, CA (US); Dalin Li, Walnut, CA (US); Janine Bilsborough, Simi Valley, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 10 days.

(21) Appl. No.: 14/779,893

(22) PCT Filed: Mar. 27, 2014

(86) PCT No.: PCT/US2014/032054
§ 371 (c)(1),
(2) Date: Sep. 24, 2015

(87) PCT Pub. No.: WO2014/160883
PCT Pub. Date: Oct. 2, 2014

(65) Prior Publication Data
US 2016/0060335 A1    Mar. 3, 2016

Related U.S. Application Data

(60) Provisional application No. 61/805,806, filed on Mar. 27, 2013, provisional application No. 61/872,020, filed on Aug. 30, 2013.

(51) Int. Cl.
*A61K 39/395* (2006.01)
*G01N 33/50* (2006.01)
(Continued)

(52) U.S. Cl.
CPC ...... *C07K 16/2866* (2013.01); *A61K 39/3955* (2013.01); *A61K 45/06* (2013.01);
(Continued)

(58) Field of Classification Search
None
See application file for complete search history.

(56) References Cited

U.S. PATENT DOCUMENTS 3,654,090 A   4/1972  Antonius et al.
3,850,752 A   11/1974 Schuurs et al.
(Continued)

FOREIGN PATENT DOCUMENTS

AU         698604 B2    11/1998
AU      2014317991 A1    3/2016
(Continued)

OTHER PUBLICATIONS

Burstein et al., Atrial fibrosis: mechanisms and clinical relevance in atrial fibrillation, J. Am. College Cardiol., 51(8), 2008.*
(Continued)

*Primary Examiner* — Claire Kaufman
(74) *Attorney, Agent, or Firm* — Wilson Sonsini Goodrich & Rosati

(57) ABSTRACT

The invention relates to methods of treating fibrosis and inflammatory bowel disease. In one embodiment, the present invention treats gut inflammation by administering a therapeutically effective dosage of TL1A inhibitors and/or DR3 inhibitors to an individual. In another embodiment, the present invention provides a method of reversing tissue fibrosis in an individual by inhibiting TL1A-DR3 signaling function.

17 Claims, 15 Drawing Sheets

(51) Int. Cl.
  *C12Q 1/68* (2018.01)
  *C07K 14/715* (2006.01)
  *C07K 16/28* (2006.01)
  *C12Q 1/6883* (2018.01)
  *A61K 45/06* (2006.01)
  *C07K 16/24* (2006.01)
  *C12N 15/113* (2010.01)
  *G01N 33/68* (2006.01)

(52) U.S. Cl.
  CPC .......... *C07K 16/24* (2013.01); *C12N 15/1138* (2013.01); *C12Q 1/6883* (2013.01); *G01N 33/6869* (2013.01); *C07K 2317/76* (2013.01); *C12N 2320/30* (2013.01); *C12Q 2600/112* (2013.01); *C12Q 2600/156* (2013.01); *C12Q 2600/158* (2013.01); *G01N 2333/7155* (2013.01); *G01N 2800/065* (2013.01); *G01N 2800/10* (2013.01)

(56) References Cited

U.S. PATENT DOCUMENTS

| | | |
|---|---|---|
| 4,016,043 A | 4/1977 | Schuurs et al. |
| 4,265,823 A | 5/1981 | Nobile |
| 4,518,584 A | 5/1985 | Mark et al. |
| 4,698,195 A | 10/1987 | Okumura et al. |
| 4,699,880 A | 10/1987 | Goldstein |
| 4,704,692 A | 11/1987 | Ladner |
| 4,737,462 A | 4/1988 | Mark et al. |
| 4,800,159 A | 1/1989 | Mullis et al. |
| 4,880,548 A | 11/1989 | Pall et al. |
| 4,925,572 A | 5/1990 | Pall |
| 4,935,234 A | 6/1990 | Todd, III et al. |
| 4,946,778 A | 8/1990 | Ladner et al. |
| 5,002,873 A | 3/1991 | St. John et al. |
| 5,085,318 A | 2/1992 | Leverick |
| 5,091,302 A | 2/1992 | Newman et al. |
| 5,114,842 A | 5/1992 | Plow et al. |
| 5,137,806 A | 8/1992 | LeMaistre et al. |
| 5,147,637 A | 9/1992 | Wright et al. |
| 5,210,015 A | 5/1993 | Gelfand et al. |
| 5,219,997 A | 6/1993 | Schlossman et al. |
| 5,225,539 A | 7/1993 | Winter |
| 5,227,369 A | 7/1993 | Rosen et al. |
| 5,234,810 A | 8/1993 | Kehrli, Jr. et al. |
| 5,235,049 A | 8/1993 | McClelland et al. |
| 5,236,081 A | 8/1993 | Fitzsimmons et al. |
| 5,263,743 A | 11/1993 | Jones |
| 5,264,554 A | 11/1993 | Newman |
| 5,272,263 A | 12/1993 | Hession et al. |
| 5,284,931 A | 2/1994 | Springer et al. |
| 5,411,842 A | 5/1995 | Ridgway et al. |
| 5,491,063 A | 2/1996 | Fisher et al. |
| 5,494,920 A | 2/1996 | Glasebrook et al. |
| 5,518,488 A | 5/1996 | Schluger |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,590,769 A | 1/1997 | Lin |
| 5,607,879 A | 3/1997 | Wuu et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,683,698 A | 11/1997 | Chavali et al. |
| 5,691,151 A | 11/1997 | Braun et al. |
| 5,713,061 A | 1/1998 | Yoshioka |
| 5,750,355 A | 5/1998 | Targan et al. |
| 5,830,675 A | 11/1998 | Targan et al. |
| 5,840,300 A | 11/1998 | Williams et al. |
| 5,861,155 A | 1/1999 | Lin |
| 5,874,233 A | 2/1999 | Targan et al. |
| 5,885,793 A | 3/1999 | Griffiths et al. |
| 5,905,827 A | 5/1999 | Naganuma et al. |
| 5,916,748 A | 6/1999 | Targan et al. |
| 5,937,862 A | 8/1999 | Targan et al. |
| 5,942,390 A | 8/1999 | Cominelli et al. |
| 5,947,281 A | 9/1999 | Kaneff |
| 5,968,741 A | 10/1999 | Plevy et al. |
| 5,969,108 A | 10/1999 | McCafferty et al. |
| 6,034,102 A | 3/2000 | Aiello |
| 6,074,835 A | 6/2000 | Braun et al. |
| 6,114,395 A | 9/2000 | Aiello |
| 6,172,197 B1 | 1/2001 | McCafferty et al. |
| 6,183,951 B1 | 2/2001 | Plevy et al. |
| 6,215,040 B1 | 4/2001 | Lee et al. |
| 6,297,367 B1 | 10/2001 | Tribouley |
| 6,300,064 B1 | 10/2001 | Knappik et al. |
| 6,348,316 B1 | 2/2002 | Taylor et al. |
| 6,376,176 B1 | 4/2002 | Taylor et al. |
| 6,406,701 B1 | 6/2002 | Pulido-Cejudo |
| 6,407,213 B1 | 6/2002 | Carter et al. |
| 6,479,284 B1 | 11/2002 | Marasco et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,599,719 B2 | 7/2003 | Yu et al. |
| 6,607,879 B1 | 8/2003 | Cocks et al. |
| 6,632,976 B1 | 10/2003 | Tomizuka et al. |
| 6,653,068 B2 | 11/2003 | Frisch et al. |
| 6,692,916 B2 | 2/2004 | Bevilacqua et al. |
| 6,706,484 B1 | 3/2004 | Knappik et al. |
| 6,713,061 B1 | 3/2004 | Yu et al. |
| 6,762,042 B2 | 7/2004 | Liu et al. |
| 6,812,339 B1 | 11/2004 | Venter et al. |
| 6,824,767 B2 | 11/2004 | Yu et al. |
| 6,824,989 B1 | 11/2004 | Eisinger et al. |
| 6,835,823 B2 | 12/2004 | Le et al. |
| 6,858,391 B2 | 2/2005 | Nunez et al. |
| 6,869,762 B1 | 3/2005 | Daly et al. |
| 6,905,827 B2 | 6/2005 | Wohlgemuth et al. |
| 6,950,827 B2 | 9/2005 | Jung |
| 7,060,869 B2 | 6/2006 | Tsien et al. |
| 7,138,237 B1 | 11/2006 | Targan et al. |
| 7,186,800 B1 | 3/2007 | Gentz et al. |
| 7,252,971 B2 | 8/2007 | Benson et al. |
| 7,264,963 B1 | 9/2007 | Knappik et al. |
| 7,285,267 B2 | 10/2007 | Gentz et al. |
| 7,332,156 B2 | 2/2008 | Bowman et al. |
| 7,332,631 B2 | 2/2008 | Hogarth et al. |
| 7,361,491 B2 | 4/2008 | Liu et al. |
| 7,361,733 B2 | 4/2008 | Hersberg et al. |
| 7,368,527 B2 | 5/2008 | Rosen et al. |
| 7,534,428 B2 | 5/2009 | Gentz et al. |
| 7,597,886 B2 | 10/2009 | Yu et al. |
| 7,612,181 B2 | 11/2009 | Wu et al. |
| 7,708,996 B2 | 5/2010 | Yu et al. |
| 7,709,218 B2 | 5/2010 | Gentz et al. |
| 7,745,391 B2 | 6/2010 | Mintz et al. |
| 7,759,079 B2 | 7/2010 | Oh et al. |
| 7,820,447 B2 | 10/2010 | Morris et al. |
| 7,820,798 B2 | 10/2010 | Yu et al. |
| 7,838,239 B2 | 11/2010 | Mitsuhashi et al. |
| 7,892,730 B2 | 2/2011 | Morris et al. |
| 7,993,833 B2 | 8/2011 | Begovich et al. |
| 8,003,099 B2 | 8/2011 | Auer et al. |
| 8,003,386 B1 | 8/2011 | Gentz et al. |
| 8,017,122 B2 * | 9/2011 | Siadak ................ C07K 16/244 |
| 8,093,363 B2 | 1/2012 | Yu et al. |
| 8,263,743 B2 | 9/2012 | Smith et al. |
| 8,409,577 B2 | 4/2013 | Thompson et al. |
| 8,524,869 B2 | 9/2013 | Smith et al. |
| 8,642,741 B2 | 2/2014 | Classon et al. |
| 8,728,282 B2 | 5/2014 | Niu |
| 8,728,475 B2 | 5/2014 | Burkly et al. |
| 8,728,482 B2 | 5/2014 | Smith et al. |
| 8,766,034 B2 | 7/2014 | Shih et al. |
| 8,781,750 B2 | 7/2014 | Stuart et al. |
| 8,859,739 B2 | 10/2014 | Kontermann et al. |
| 8,883,975 B2 | 11/2014 | Brandt et al. |

(56) References Cited

U.S. PATENT DOCUMENTS

| | | |
|---|---|---|
| 8,975,022 B2 | 3/2015 | Begovich et al. |
| 9,017,679 B2 | 4/2015 | Podack et al. |
| 9,068,003 B2 * | 6/2015 | Siegel ............... C07K 16/2875 |
| 9,102,733 B2 | 8/2015 | Endl et al. |
| 9,290,576 B2 | 3/2016 | Attinger et al. |
| 9,305,137 B1 | 4/2016 | Targan et al. |
| 9,332,741 B2 | 5/2016 | Shih et al. |
| 9,371,565 B2 | 6/2016 | Begovich et al. |
| 9,416,185 B2 | 8/2016 | Smith et al. |
| 9,556,277 B2 | 1/2017 | Classon et al. |
| 9,580,752 B2 | 2/2017 | Rotter et al. |
| 9,683,998 B2 | 6/2017 | Arch et al. |
| 9,834,606 B2 | 12/2017 | Li et al. |
| 9,839,670 B2 | 12/2017 | Podack et al. |
| 9,896,511 B2 | 2/2018 | Siegel et al. |
| 9,902,996 B2 | 2/2018 | Dubinsky et al. |
| 2001/0006789 A1 | 7/2001 | Maino et al. |
| 2002/0006613 A1 | 1/2002 | Shyjan et al. |
| 2002/0019837 A1 | 2/2002 | Balnaves |
| 2002/0048566 A1 | 4/2002 | El-Deiry et al. |
| 2002/0078757 A1 | 6/2002 | Hines et al. |
| 2002/0106684 A1 | 8/2002 | Kopreski |
| 2002/0150939 A1 | 10/2002 | Taylor et al. |
| 2002/0165137 A1 | 11/2002 | Ruben et al. |
| 2002/0198371 A1 | 12/2002 | Wang |
| 2003/0017518 A1 | 1/2003 | Lam et al. |
| 2003/0092019 A1 | 5/2003 | Meyer et al. |
| 2003/0129189 A1 | 7/2003 | Yu et al. |
| 2003/0129215 A1 | 7/2003 | Mollison et al. |
| 2003/0138781 A1 | 7/2003 | Whitehead |
| 2003/0148345 A1 | 8/2003 | Kopreski |
| 2003/0166871 A1 | 9/2003 | Barbas et al. |
| 2003/0176409 A1 | 9/2003 | Offner |
| 2003/0198640 A1 | 10/2003 | Yu et al. |
| 2004/0013655 A1 | 1/2004 | Shiozawa et al. |
| 2004/0053262 A1 | 3/2004 | Lu |
| 2004/0072154 A1 | 4/2004 | Morris et al. |
| 2004/0123343 A1 | 6/2004 | La Rosa et al. |
| 2004/0142325 A1 | 7/2004 | Mintz et al. |
| 2004/0181048 A1 | 9/2004 | Wang |
| 2004/0203076 A1 | 10/2004 | Targan et al. |
| 2004/0213761 A1 | 10/2004 | Bowman et al. |
| 2004/0219555 A1 | 11/2004 | Van Heel |
| 2004/0265864 A1 | 12/2004 | Mitsuhashi |
| 2005/0054021 A1 | 3/2005 | Targan et al. |
| 2005/0143333 A1 | 6/2005 | Richards et al. |
| 2005/0163764 A1 | 7/2005 | Medzhitov et al. |
| 2005/0182007 A1 | 8/2005 | McSwiggen et al. |
| 2005/0228172 A9 | 10/2005 | Wang |
| 2005/0260204 A1 | 11/2005 | Allan |
| 2005/0261219 A1 | 11/2005 | Richards et al. |
| 2006/0003392 A1 | 1/2006 | Oh et al. |
| 2006/0008819 A1 | 1/2006 | Curtis et al. |
| 2006/0067936 A1 | 3/2006 | Benson et al. |
| 2006/0100132 A1 | 5/2006 | Corneliussen et al. |
| 2006/0134663 A1 | 6/2006 | Harkin et al. |
| 2006/0141478 A1 | 6/2006 | Brant et al. |
| 2006/0154276 A1 | 7/2006 | Lois et al. |
| 2006/0211020 A1 | 9/2006 | Farrer et al. |
| 2006/0234285 A1 | 10/2006 | Gentz et al. |
| 2007/0015271 A1 | 1/2007 | Rosen et al. |
| 2007/0020268 A1 | 1/2007 | Ashkenazi et al. |
| 2007/0020637 A1 | 1/2007 | Isogai et al. |
| 2007/0037165 A1 | 2/2007 | Venter et al. |
| 2007/0054278 A1 | 3/2007 | Cargill |
| 2007/0054282 A1 | 3/2007 | Liew |
| 2007/0059758 A1 | 3/2007 | Levine |
| 2007/0072180 A1 | 3/2007 | Abreu et al. |
| 2007/0083334 A1 | 4/2007 | Mintz et al. |
| 2007/0161031 A1 | 7/2007 | Trinklein et al. |
| 2007/0196835 A1 | 8/2007 | Bankaitis-Davis et al. |
| 2007/0237770 A1 | 10/2007 | Lai et al. |
| 2007/0254850 A1 | 11/2007 | Lieberman et al. |
| 2007/0275424 A1 | 11/2007 | Gewirtz et al. |
| 2008/0003221 A1 | 1/2008 | Podack et al. |
| 2008/0038746 A1 | 2/2008 | Rosenberg et al. |
| 2008/0038831 A1 | 2/2008 | Benson |
| 2008/0081822 A1 | 4/2008 | Berry et al. |
| 2008/0091471 A1 | 4/2008 | Michon et al. |
| 2008/0095775 A1 | 4/2008 | Lewis et al. |
| 2008/0103180 A1 | 5/2008 | Fleming et al. |
| 2008/0108713 A1 | 5/2008 | Begovich et al. |
| 2008/0131887 A1 | 6/2008 | Stephan et al. |
| 2008/0177048 A1 | 7/2008 | Gagnon |
| 2008/0206762 A1 | 8/2008 | Ferrer et al. |
| 2008/0261207 A1 | 10/2008 | Mitsuhashi |
| 2008/0274467 A1 | 11/2008 | Morris et al. |
| 2008/0293582 A1 | 11/2008 | Li et al. |
| 2009/0018031 A1 | 1/2009 | Trinklein et al. |
| 2009/0048119 A1 | 2/2009 | Krjutskov et al. |
| 2009/0099789 A1 | 4/2009 | Stephan et al. |
| 2009/0162350 A1 | 6/2009 | Abbas et al. |
| 2009/0180380 A1 | 7/2009 | Prabhakar et al. |
| 2009/0186034 A1 | 7/2009 | Abbas et al. |
| 2009/0187005 A1 | 7/2009 | Gagnon |
| 2009/0220417 A1 * | 9/2009 | Siadak ................ C07K 16/244 |
| 2009/0221437 A1 | 9/2009 | Harkin et al. |
| 2009/0253133 A1 | 10/2009 | Mitsuhashi et al. |
| 2009/0258848 A1 | 10/2009 | Chakravarti et al. |
| 2009/0297563 A1 | 12/2009 | Borglum et al. |
| 2009/0317388 A1 * | 12/2009 | Burkly ............... A01K 67/0276 424/134.1 |
| 2010/0015156 A1 | 1/2010 | Dubinsky et al. |
| 2010/0019016 A1 | 1/2010 | Edoga et al. |
| 2010/0021455 A1 | 1/2010 | Targan et al. |
| 2010/0021917 A1 | 1/2010 | Rotter et al. |
| 2010/0041600 A1 | 2/2010 | Russel et al. |
| 2010/0055700 A1 | 3/2010 | Targan et al. |
| 2010/0099092 A1 | 4/2010 | Song et al. |
| 2010/0105044 A1 | 4/2010 | Fleshner et al. |
| 2010/0136543 A1 | 6/2010 | Georges et al. |
| 2010/0144903 A1 | 6/2010 | Taylor et al. |
| 2010/0184050 A1 | 7/2010 | Rotter et al. |
| 2010/0190162 A1 | 7/2010 | Rotter et al. |
| 2010/0240043 A1 | 9/2010 | Rotter et al. |
| 2010/0240077 A1 | 9/2010 | Targan et al. |
| 2010/0254971 A1 | 10/2010 | Dotan et al. |
| 2010/0266594 A1 | 10/2010 | Reed |
| 2010/0284999 A1 | 11/2010 | Taylor et al. |
| 2010/0291551 A1 | 11/2010 | Belouchi |
| 2010/0298232 A1 | 11/2010 | Liu |
| 2011/0003707 A1 | 1/2011 | Goix et al. |
| 2011/0033486 A1 | 2/2011 | Abbas et al. |
| 2011/0045476 A1 | 2/2011 | Barken et al. |
| 2011/0111418 A1 | 5/2011 | Rhodes et al. |
| 2011/0124644 A1 | 5/2011 | Targan et al. |
| 2011/0136113 A1 | 6/2011 | Uga et al. |
| 2011/0159011 A1 | 6/2011 | Carrier et al. |
| 2011/0160085 A1 | 6/2011 | Li et al. |
| 2011/0177502 A1 | 7/2011 | Hakonarson et al. |
| 2011/0177969 A1 | 7/2011 | Rotter et al. |
| 2011/0189685 A1 | 8/2011 | Taylor et al. |
| 2011/0217310 A1 | 9/2011 | Siegel et al. |
| 2011/0229471 A1 | 9/2011 | Rotter et al. |
| 2011/0243951 A1 | 10/2011 | Podack et al. |
| 2012/0014950 A1 | 1/2012 | Migone et al. |
| 2012/0026371 A1 | 2/2012 | Itano et al. |
| 2012/0041082 A1 | 2/2012 | Rotter et al. |
| 2012/0053131 A1 | 3/2012 | Rotter et al. |
| 2012/0073585 A1 | 3/2012 | Rotter et al. |
| 2012/0079611 A1 | 3/2012 | Shih et al. |
| 2012/0094934 A1 | 4/2012 | Collard et al. |
| 2012/0114654 A1 | 5/2012 | Classon et al. |
| 2012/0135011 A1 | 5/2012 | Podack et al. |
| 2012/0190698 A1 | 7/2012 | Dubinsky et al. |
| 2012/0208900 A1 | 8/2012 | Dubinsky et al. |
| 2012/0263718 A1 | 10/2012 | Siegel et al. |
| 2012/0315282 A1 | 12/2012 | Bedinger et al. |
| 2012/0328559 A1 | 12/2012 | Podack et al. |
| 2013/0012602 A1 | 1/2013 | Haritunians et al. |
| 2013/0012604 A1 | 1/2013 | Rotter et al. |
| 2013/0123117 A1 | 5/2013 | Xu et al. |
| 2013/0129668 A1 | 5/2013 | Firestein et al. |
| 2013/0136720 A1 | 5/2013 | McGovern et al. |

(56) References Cited

U.S. PATENT DOCUMENTS

| | | |
|---|---|---|
| 2013/0142809 A1 | 6/2013 | Welcher et al. |
| 2013/0344621 A1 | 12/2013 | Wang et al. |
| 2014/0017711 A1 | 1/2014 | Taylor et al. |
| 2014/0018447 A1 | 1/2014 | McGovern et al. |
| 2014/0018448 A1 | 1/2014 | Gonsky et al. |
| 2014/0037618 A1 | 2/2014 | Pidasheva et al. |
| 2014/0162894 A1 | 6/2014 | Hatchwell et al. |
| 2014/0255302 A1* | 9/2014 | Poulton ............... C07K 16/241 424/1.49 |
| 2015/0026831 A1 | 1/2015 | Shih et al. |
| 2015/0031972 A1 | 1/2015 | Freeman et al. |
| 2015/0086567 A1 | 3/2015 | Gonsky et al. |
| 2015/0132311 A1 | 5/2015 | Arch et al. |
| 2015/0313904 A1 | 11/2015 | Kolatch et al. |
| 2015/0337378 A1 | 11/2015 | Targan et al. |
| 2015/0376612 A1 | 12/2015 | Lee et al. |
| 2015/0376707 A1 | 12/2015 | Targan |
| 2016/0053007 A1 | 2/2016 | Siegel et al. |
| 2016/0060330 A1 | 3/2016 | Presta |
| 2016/0060335 A1 | 3/2016 | Shih et al. |
| 2016/0090629 A1 | 3/2016 | McGovern |
| 2016/0096885 A1 | 4/2016 | Shih et al. |
| 2016/0200833 A1 | 7/2016 | Amann et al. |
| 2016/0208329 A1 | 7/2016 | Targan et al. |
| 2016/0215046 A1 | 7/2016 | Michelson et al. |
| 2016/0222450 A1 | 8/2016 | Schrodi et al. |
| 2016/0333104 A1 | 11/2016 | Poulton et al. |
| 2017/0044615 A1 | 2/2017 | Rotter et al. |
| 2017/0081400 A1 | 3/2017 | Poulton et al. |
| 2017/0096491 A1 | 4/2017 | Classon et al. |
| 2017/0166967 A1 | 6/2017 | Rotter et al. |
| 2018/0021696 A1 | 1/2018 | Wang et al. |
| 2018/0051078 A1 | 2/2018 | Targan et al. |
| 2018/0052175 A1 | 2/2018 | Arch et al. |
| 2018/0078611 A1 | 3/2018 | Podack et al. |
| 2018/0086840 A1 | 3/2018 | Attinger et al. |
| 2018/0110855 A1 | 4/2018 | Bilsborough |
| 2018/0142302 A1 | 5/2018 | Dubinsky |
| 2018/0156781 A1 | 6/2018 | Shih |
| 2018/0208988 A1 | 7/2018 | Targan et al. |
| 2018/0230543 A1 | 8/2018 | Mcgovern |
| 2018/0305689 A1 | 10/2018 | Sætrom et al. |

FOREIGN PATENT DOCUMENTS

| | | |
|---|---|---|
| CA | 2468316 A1 | 6/2003 |
| CA | 2471840 A1 | 7/2003 |
| CA | 2668691 A1 | 6/2008 |
| CA | 2830351 A1 | 10/2012 |
| CA | 2830362 A1 | 10/2012 |
| CA | 2830365 A1 | 10/2012 |
| CA | 2922381 A1 | 3/2015 |
| CL | 2015002866-15 A1 | 8/2016 |
| CN | 101198624 A | 6/2008 |
| CN | 101903402 A | 12/2010 |
| CN | 202109170 U | 1/2012 |
| CN | 103149371 A | 6/2013 |
| CN | 105246501 A | 1/2016 |
| CN | 105358713 A | 2/2016 |
| CN | 105636648 A | 6/2016 |
| EP | 0760010 B1 | 10/2001 |
| EP | 1285271 B1 | 8/2005 |
| EP | 1716227 A2 | 11/2006 |
| EP | 1243274 B1 | 6/2008 |
| EP | 2005175 A2 | 12/2008 |
| EP | 2034030 A2 | 3/2009 |
| EP | 2064345 A2 | 6/2009 |
| EP | 2097540 A2 | 9/2009 |
| EP | 1819827 B1 | 8/2010 |
| EP | 2270512 A1 | 1/2011 |
| EP | 2565277 A1 | 3/2013 |
| EP | 2689034 A2 | 1/2014 |
| EP | 2689036 A2 | 1/2014 |
| EP | 2689246 A1 | 1/2014 |
| EP | 2978440 A1 | 3/2016 |
| EP | 2996717 A2 | 3/2016 |
| EP | 2997165 A2 | 3/2016 |
| EP | 2462165 B1 | 5/2016 |
| EP | 3022295 A2 | 5/2016 |
| EP | 3041580 A2 | 7/2016 |
| EP | 2638069 B1 | 1/2018 |
| EP | 3270964 A1 | 1/2018 |
| EP | 3294336 A1 | 3/2018 |
| IN | 2776MUMNP2015 A | 3/2016 |
| JP | 2005510225 A | 4/2005 |
| JP | 2005514923 A | 5/2005 |
| JP | 2008518610 A | 6/2008 |
| JP | 2009526756 A | 7/2009 |
| JP | 2009195249 A | 9/2009 |
| JP | 2009535016 A | 10/2009 |
| JP | 2010088432 A | 4/2010 |
| JP | 2014515599 A | 7/2014 |
| JP | 2016522164 A | 7/2016 |
| JP | 2016526875 A | 9/2016 |
| JP | 2016536002 A | 11/2016 |
| JP | 2016198116 A | 12/2016 |
| KR | 20150134393 A | 12/2015 |
| KR | 20160009582 A | 1/2016 |
| KR | 20160052585 A | 5/2016 |
| WO | WO-9116928 A1 | 11/1991 |
| WO | WO-9202819 A2 | 2/1992 |
| WO | WO-9222323 A1 | 12/1992 |
| WO | WO-9307485 A1 | 4/1993 |
| WO | WO-9312248 A1 | 6/1993 |
| WO | WO-9404188 A1 | 3/1994 |
| WO | WO-9521941 A1 | 8/1995 |
| WO | WO-9531575 A1 | 11/1995 |
| WO | WO-9614328 A1 | 5/1996 |
| WO | WO-9725445 A1 | 7/1997 |
| WO | WO-9847004 A1 | 10/1998 |
| WO | WO-0066608 A1 | 11/2000 |
| WO | WO-0076492 A1 | 12/2000 |
| WO | WO-0120036 A2 | 3/2001 |
| WO | WO-0142511 A2 | 6/2001 |
| WO | WO-0157182 A2 | 8/2001 |
| WO | WO-0204643 A1 | 1/2002 |
| WO | WO-0157182 A3 | 3/2002 |
| WO | WO-0228999 A2 | 4/2002 |
| WO | WO-03008583 A2 | 1/2003 |
| WO | WO-03025148 A2 | 3/2003 |
| WO | WO-03040404 A1 | 5/2003 |
| WO | WO-03053220 A2 | 7/2003 |
| WO | WO-03057146 A2 | 7/2003 |
| WO | WO-03059333 A2 | 7/2003 |
| WO | WO-03090694 A2 | 11/2003 |
| WO | WO-03099312 A1 | 12/2003 |
| WO | WO-2004020968 A2 | 3/2004 |
| WO | WO-2004031159 A1 | 4/2004 |
| WO | WO-2004035537 A2 | 4/2004 |
| WO | WO-2004048600 A2 | 6/2004 |
| WO | WO-2004050836 A2 | 6/2004 |
| WO | WO-2005044792 A2 | 5/2005 |
| WO | WO-2005114469 A1 | 12/2005 |
| WO | WO-2005115115 A2 | 12/2005 |
| WO | WO-2005116251 A1 | 12/2005 |
| WO | WO-2006017173 A2 | 2/2006 |
| WO | WO-2006063093 A2 | 6/2006 |
| WO | WO 2006075254 A2 | 7/2006 |
| WO | WO-2006110091 A1 | 10/2006 |
| WO | WO-2006116721 A1 | 11/2006 |
| WO | WO-2007005608 A2 | 1/2007 |
| WO | WO-2007025989 A2 | 3/2007 |
| WO | WO-2007117611 A2 | 10/2007 |
| WO | WO-2007133816 A2 | 11/2007 |
| WO | WO-2007140625 A1 | 12/2007 |
| WO | WO-2008014400 A2 | 1/2008 |
| WO | WO-2008033239 A2 | 3/2008 |
| WO | WO-2008048902 A2 | 4/2008 |
| WO | WO-2008048984 A2 | 4/2008 |
| WO | WO-2008048986 A2 | 4/2008 |
| WO | WO-2008101133 A2 | 8/2008 |
| WO | WO 2008106451 A2 | 9/2008 |
| WO | WO-2008106579 A2 | 9/2008 |

(56) References Cited

FOREIGN PATENT DOCUMENTS

| | | |
|---|---|---|
| WO | WO 2008109782 A2 | 9/2008 |
| WO | WO-2008112990 A2 | 9/2008 |
| WO | WO-2008116150 A2 | 9/2008 |
| WO | WO-2008106451 A3 | 11/2008 |
| WO | WO-2008134569 A2 | 11/2008 |
| WO | WO-2008137762 A2 | 11/2008 |
| WO | WO-2008141148 A2 | 11/2008 |
| WO | WO-2009020403 A1 | 2/2009 |
| WO | WO 2009052512 A2 | 4/2009 |
| WO | WO-2009073628 A2 | 6/2009 |
| WO | WO 2009105590 A2 | 8/2009 |
| WO | WO-2009117122 A2 | 9/2009 |
| WO | WO-2009143278 A2 | 11/2009 |
| WO | WO-2009105590 A3 | 1/2010 |
| WO | WO-2010008858 A1 | 1/2010 |
| WO | WO 2010075579 A2 | 1/2010 |
| WO | WO-2010039931 A2 | 4/2010 |
| WO | WO-2010048415 A1 | 4/2010 |
| WO | WO-2010056682 A2 | 5/2010 |
| WO | WO-2010062960 A2 | 6/2010 |
| WO | WO-2010075584 A1 | 7/2010 |
| WO | WO-2010083234 A1 | 7/2010 |
| WO | WO-2010118210 A1 | 10/2010 |
| WO | WO-2010120814 A1 | 10/2010 |
| WO | WO-2011017120 A1 | 2/2011 |
| WO | WO-2011088237 A1 | 7/2011 |
| WO | WO-2011088306 A1 | 7/2011 |
| WO | WO-2011088380 A1 | 7/2011 |
| WO | WO-2011116111 A1 | 9/2011 |
| WO | WO-2012054532 A1 | 4/2012 |
| WO | WO 2012064682 A1 | 5/2012 |
| WO | WO-2012135142 A1 | 10/2012 |
| WO | WO-2012135144 A2 | 10/2012 |
| WO | WO-2012135146 A2 | 10/2012 |
| WO | WO-2012154253 A1 | 11/2012 |
| WO | WO-2012161856 A1 | 11/2012 |
| WO | WO-2012174338 A2 | 12/2012 |
| WO | WO-2013012604 A1 | 1/2013 |
| WO | WO-2013059732 A1 | 4/2013 |
| WO | WO-2014106602 A1 | 7/2014 |
| WO | WO-2014160463 A1 | 10/2014 |
| WO | WO 2014160883 A1 | 10/2014 |
| WO | WO 2014186665 A2 | 11/2014 |
| WO | WO 2014186750 A2 | 11/2014 |
| WO | WO 2015010108 A1 | 1/2015 |
| WO | WO 2015035261 A1 | 3/2015 |
| WO | WO-2015168699 A1 | 11/2015 |
| WO | WO-2016149282 A1 | 9/2016 |
| WO | WO 2016186972 A1 | 11/2016 |
| WO | WO-2017077715 A1 | 5/2017 |
| WO | WO-2017106383 A1 | 6/2017 |
| WO | WO-2017161342 A1 | 9/2017 |
| WO | WO-2017196663 A1 | 11/2017 |
| WO | WO-2018081074 A1 | 5/2018 |

OTHER PUBLICATIONS

Rieder et al., Intestinal fibrosis in inflammatory bowel disease—current knowledge and future perspectives, J. Crohn's Colitis, 2:279-290, 2008.*

Meylan et al., The TNF-family cytokine TL1A drives IL-13-dependent small intestinal inflammation, Mucosal Immunol. 4(2):172-185, Mar. 2011.*

Fessler et al., A genomic and proteomic analysis of activation of the human neutrophil by lipopolysaccharide and its mediateion by p38 mitogen-activated protein kinase, J. Biol. Chem. 277(35): 31291-302, Aug. 2002.*

Bull et al., The death receptor 3-TNF-like protein 1A pathway drives adverse bone pathology in inflammatory arthritis, J. Exp. Med. 205(11):2457-24646, 2008.*

Chen et al., Discordant protein and mRNA expression in lugn adenocarcinomas, Mol. Cell Proteomics 1.4:304, 2002.*

Shih et al.,Inhibition of a novel fibrogenic factor Tl1a reverses established colonic fibrosis, Mucosal Immunol. 7(6):1492-1503, Nov. 2014.*

NCBI Gene Database, Gene ID: 133396, IL31RA interleukin 31 receptor A [*Homo sapiens* (human)], [Rtrieved online Aug. 31, 2018] Retrieved from <URL:https://www.ncbi.nlm.nih.gov/gene/133396#gene-expression>., Aug. 5, 2018.*

NCBI Gene Database, Gene ID: 3458, IFNG interferon gamma [*Homo sapiens* (human)], [Rtrieved online Aug. 31, 2018] Retrieved from <URL:https://www.ncbi.nlm.nih.gov/gene/3458#gene-expression>., Aug. 25, 2018.*

Camoglio et al., Altered expression of interfero-gamma and interleukin-4 in inflammatory bowel disease, Inflamm. Bowel Dis.,4(4): 285-290, Nov. 1998, Abstract only.*

UniprotKB Database, Q8NI17 (IL31R_Human), Retrieved online Sep. 5, 2019. Retrieved from <URL https://www.uniprot.org/uniprot/Q8NI17>. Jul. 31, 2919.*

EP 14773989.0 Extended European Search Report dated Dec. 19, 2016, 11 pages.

Takedatsu et al., TL1A (TNFSF15) Regulates the Development of Chronic Colitis by Modulating Both T-Helper 1 and T-Helper 17 Activation, Gastroenterology, 2008, vol. 135(2), pp. 552-567.

Barrett et al., Constitutive TL1A Expression under Colitogenic Condition Modulates the Severity and Location of Gut Mucosal Inflammation and Induces Fibrostenosis, American Journal of Pathology, 2012, vol. 180(2), pp. 636-649.

Shih et al., Constitutive TL1A (TNFSF15) Expression on Lymphoid or Myeloid Cells Leads to Mild Intestinal Inflammation and Fibrosis, PLOS ONE, 2011, vol. 6(1), p. e106090.

International Preliminary Report on Patentability for PCT/US2008/055020 dated Aug. 26, 2009; 6 pages.

International Preliminary Report on Patentability for PCT/US2008/080526 dated Apr. 20, 2010; 6 pages.

International Preliminary Report on Patentability for PCT/US2009/069531 dated Jun. 29, 2011; 6 pages.

International Preliminary Report on Patentability for PCT/US2014/038333 dated Nov. 26, 2015; 6 Pages.

International Preliminary Report on Patentability for PCT/US2014/038468 dated Nov. 18, 2014; 7 Pages.

Intl. Preliminary Report on Patentability for PCT/US2014/054425 dated Dec. 31, 2014, 10 pages.

Intl. Preliminary Report on Patentability for PCT/US2014/047326 dated Dec. 22, 2014, 7 pages.

International Search Report and Written Opinion for PCT/US2008/055020 dated Aug. 14, 2008; 8 pages.

International Search Report and Written Opinion for PCT/US2008/080526 dated Mar. 25, 2009; 11 pages.

International Search Report and Written Opinion for PCT/US2009/069531 dated Aug. 4, 2010; 11 pages.

International Search Report and Written Opinion for PCT/US2014/038333 dated Nov. 20, 2014; 9 Pages.

International Search Report and Written Opinion for PCT/US2014/038468 dated Nov. 18, 2014; 10 Pages.

International Search Report and Written Opinion for PCT/US2014/054425 dated Dec. 31, 2014, 3 pages.

International Search Report and Written Opinion for PCT/US2014/047326 dated Dec. 22, 2014, 3 pages.

International Search Report and Written Opinion for PCT/US2016/032180 dated Aug. 19, 2016, 8 pages.

Extended European Search Report in EP14798650 dated Oct. 21, 2016, 13 pages.

Partial Search Report for EP14797214 dated Oct. 28, 2016, 10 pages.

Extended European Search Report in EP14797214 dated Feb. 3, 2017, 15 pages.

Partial Search Report for EP14842590 dated Jan. 18, 2017, 8 pages.

Extended European Search Report in EP14826746 dated Feb. 1, 2017, 13 pages.

Aggarwal et al. The Role of TNF and its Family Members in Inflammation and Cancer: Lessons from Gene Deletion, Curr. Drug Targets Inflamm. Allergy, 2002, vol. 1(4), pp. 327-341.

Babbage, A., Human DNA Sequence from Clone RP11-428F18 on Chromosome 9, Complete Sequence, GenBank: AL390240, Dec. 13, 2012, pp. 1-31.

(56) References Cited

OTHER PUBLICATIONS

Bamias et al., Proinflammatory Effects of Th2 Cytokines in a Murine Model of Chronic Small Intestinal Inflammation, Gastroenterol, 2005, vol. 128, pp. 654-666.

Bamias et al., Role of TL1A and its Receptor DR3 in Two Models of Chronic Murine Ileitis, PNAS, 2006, vol. 103(22), pp. 8441-8446.

Biener-Ramanujan et al., Functional Signaling of Membrane-Bound TL1A induces IFN-Gamma Expression. FEBS Lett, 2010, vol. 11, pp. 2376-2380.

Bomprezzi et al., Gene Expression Profile in Multiple Sclerosis Patients and Healthy Controls: Identifying Pathways Relevant to Disease, Human Molecular Genetics, 2003, vol. 12(17), pp. 2191-2199.

Braasch et al., Novel Antisense and Peptide Nucleic Acid Strategies for Controlling Gene Expression, Biochemistry, 2002, vol. 41(14), pp. 4503-4509.

Brand, Crohn's Disease: Th1, Th17 or both? The Change of a Paradigm: New Immunological and Genetic Insights Implicate Th17 Cells in the Pathogenesis of Crohn's Disease, Gut, 2009, vol. 58(8), pp. 1152-1167.

Dubinsky et al., CARD8: A Novel Association with Childhood Onset Ulcerative Colitis (UC), AGA Institute, 2006, Abstract # T1983, p. A-587.

Ghosh et al., Anti-TNF Therapy in Crohn's Disease, *Novartis Foundation Symposium*, 2004, vol. 263, pp. 193-218.

Heresbach et al., NOD2/CARD15 Gene Polymorphisms in Crohn's Disease: A Genotype-Phenotype Analysis, *Eur J Gastroenterology and Hepatology*, 2004, vol. 16, pp. 55-62.

Hirano et al., Association Study of 71 European Crohn's Disease Susceptibility Loci in a Japanese Population, Inflammatory Bowel Diseases, 2013, vol. 19(3), pp. 526-533.

Hornquist et al., Gai2-Deficient Mice with Colitis Exhibit a Local Increase in Memory CD4+ T Cells and Proinflammatory TH1-Type Cytokines, J Immunol, 1997, vol. 158, pp. 1068-1077.

Houdebine, Louis Marie, Production of Pharmaceutical Proteins from Transgenic Animals, J Biotech, 1994, vol. 34, pp. 269-287.

Hsu et al., Attenuation of Th1 Response in Decoy Receptor 3 Transgenic Mice, J. Immunol, 2005, vol. 175, pp. 5135-5145.

Jikihara et al., Interferon-y Inhibits the Synthesis and Release of Renin from Human Decidual Cells, Biology of Reproduction, 1996, vol. 54, pp. 1311-1316.

Kasperkovitz et al., Activation of the STAT1 Pathway in Rheumatoid Arthritis, Ann Rheum Dis, 2004, vol. 63, pp. 233-239.

Lawrance et al., Ulcerative Colitis and Crohn's Disease: Distinctive Gene Expression Profiles and Novel Susceptibility Candidate Genes, Human Molecular Genetics, 2001, vol. 10(5), pp. 445-456.

Leong et al., NOD2/CARD15 Gene Polymorphisms and Crohn's Disease in the Chinese Population, *Aliment Pharmacol Thera*, 2003, vol. 17, pp. 1465-1470.

Levy-Coffman, Ellen, A Mosiac of People: The Jewish Story and a Reassessment of the DNA Evidence, Journal of Genetic Genealogy, 2005, vol. 1, pp. 12-33.

Low et al., High-Throughout Genomic Technology in Research and Clinical Management of Breast Cancer, Evolving Landscape of Genetic Epidemiological Studies, Breast Cancer Research, 2006, vol. 8(3), p. 209-214.

Martinez et al., Regulation and Function of Proinflammatory TH17 Cells, Animals of the New York Academy of Sciences, 2008, vol. 1143(1), pp. 188-211.

Mascheretti et al., Pharmacogenetic Investigation of the TNF/TNF-Receptor System in Patients with Chronic Active Crohn's Disease Treated with Infliximib, *The Pharmacogenomics Journal*, 2002, vol. 2 pp. 127-136.

Mei L., Association Between IL17A and IL17RA Genes and Inflammatory Bowel Disease (IBD), 2007, Abstract only, Journal unknown.

Migone et al., TL1A is a TNF-like Ligand for DR3 and TR6/DcR3 and Functions as a T cell Costimulator, Immunity, 2002, vol. 16, pp. 479-492.

Mullins et al., Perspective Series: Molecular Medicine in Genetically Engineered Animals, J Clin Invest, 1996, vol. 97, pp. 1557-1560.

Mummidi et al., Evolution of Human and Non-Human Primate CC Chemokine Receptor 5 Gene and mRNA, Journal of Biological Chemistry, 2000, vol. 275(25), pp. 18946-18961.

Naundorf et al., IL-10 Interferes Directly with TCR-Induced IFN-[gamma] but not IL-17 Production in Memory T cells, European Journal of Immunology, 2009, vol. 39(4), pp. 1066-1077.

Ogura et al., A Frameshift Mutation in NOD2 Associates with Susceotibility to Crohn's Disease, Nature, 2001, vol. 411, pp. 603-606.

Papadakis et al., TL1A synergizes with IL-12 and IL-18 to enhance IFN-y production in human T cells and NK cells, The Journal of Immunology, 2004, vol. 172, pp. 7002-7007.

Pappu et al., TL1A-DR3 Interaction Regulates Th17 Cell Function and TH17-Mediated Autoimmune Disease, Journal of External Medicine, 2008, vol. 205(5), pp. 1049-1062.

Plevy et al., A Role of TNF-Alpha and Mucosal T-helper-1 Cytokines in the Pathogenesis of Crohn's Disease, *The Journal of Immunology*, 1997, vol. 84, pp. 1397-1398.

Prehn et al., The T Cell Costimulator TL1A Is Induced by Fc R Signaling in Human Monocytes and Dendritic Cells, *J Immunol*, 2007, vol. 178, pp. 4033-4038.

Prideaux et al., Inflammatory Bowel Disease in Asia: A Systematic Review, Journal of Gastroenterology and Hepatology, 2012, vol. 27(8), pp. 1266-1280.

Satsangi et al., Contribution of Genes of the Major Histocompatibility Complex to Susceptibility and Disease Phenotype in Inflammatory Bowel Disease, The Lancet, 1996, vol. 347, pp. 1212-1217.

Seidelin et al., Upregulation of cIAP2 in Regenerating Coloncytes in Ulcerative Colitis, Virchows Arch, 2007, vol. 451, pp. 1031-1038.

Shetty et al., Pharmacogenomics of Response to Anti-Tumor Necrosis Factor Therapy in Patients with Crohn's Disease, *American Journal of Pharmacogenomics*, 2002, vol. 2, pp. 215-221.

Shih et al., Microbial Induction of Inflammatory Bowel Disease Associated Gene TL1A (TNFSF15) in Antigen Presenting Cells, Eur. J. Immunol., 2009, vol. 39, pp. 3239-3250.

Shih et al., Constitutive TL1A (TNFSF15) Expression on Lymphoid or Myeloid Cells Leads to Mild Intestinal Inflammation and Fibrosis, PLOS One, 2011, vol. 6(1), pp. 1-16.

Sobrino et al., SNP's in Forensic Genetics: A Review on SNP Typing Methodologies, Forensic Science International, 2005, vol. 154, pp. 181-194.

Syvanen, Ann-Christine, Accessing Genetic Variation: Genotyping Single Nucleotide Polymorphisms, Nature Reviews, 2001, vol. 2 p. 930.

Targan et al., TL1A (TNFSF15): A Master Regulator of Mucosal Inflammation, Advances in Experimental Medicine and Biology, 2011, vol. 691, pp. 681-683.

Thomas et al., The TNF Family Member TL1A induces IL-22 Secretion in Committed Human TH17 Cells Via IL-9 Induction, Journal of Leukocyte Biology, 2016, vol. 101, pp. 1-20.

Tremelling et al., Contribution of TNFSF15 Gene Variants to Crohn's Disease Susceptibility Confirmed in UK Population, Inflammatory Bowel Diseases, 2008, vol. 14(6), pp. 733-737.

Vermiere et al., Current Status of Genetics Research in Inflammatory Bowel Disease, *Genes and Immunity*, 2005, vol. 6, pp. 637-645.

Wall et al., Transgenic Dairy Cattle: Genetic Engineering on a Large Scale, J. Dairy Sci, 1997, vol. 80, pp. 2213-2224.

Wen et al., TL1A-Induced NF-kB Activation and c-IAP2 Production Prevent DR3-Mediated Apoptosis in TF-1 Cells, *J of Biological Chemistry*, 2003, vol. 278, pp. 39251-39258.

Yamazaki et al., Absence of Mutation in the NOD2/CARD15 Gene Among 483 Japanese Patients with Crohn's Disease, *Hum Mol Genet*, 2002, vol. 47, pp. 469-472.

Yamazaki et al., Single Nucleotide Polymorphisms in TNFSF15 Confers Susceptibility to Crohn's Disease, *Hum Mol Genet*, 2005, vol. 14, pp. 3499-3506.

Yamazaki et al., Association Analysis of Genetic Variants in IL23R, ATG16L1 and 5p13.1 Loci with Crohn's Disease in Japanese patients, *J Hum Genet*, 2007, vol. 52, pp. 575-582.

(56) References Cited

OTHER PUBLICATIONS

GeneCard DR3 found at http://www.genecards.org/cgi-bin/carddisp.pl?gene=TNFRSF25&search=DR3 Jan. 1, 2013.
Reference SNP Cluster report for rs2986754 retrieved from: http://www.ncbi.nlm.nih.gov/projects/SNP/snp_ref.cgi?rs=2986754 on Sep. 13, 2016; 3 pages.
Reference SNP Cluster report rs746503. NCBI: Single Nucleotide Polymorphism. May 6, 2006. Retrieved from the internet, http://www.ncbi.nlm.nih.gov/projects/SNP/snp_ref.cgi?rs+746503>, 2 pages.
PCT/US2014/032054 Intl. Search Report and Written Opinion dated Aug. 5, 2014, 14 pages.
PCT/US2014/032054 Intl. Preliminary Report on Patentability dated Sep. 29, 2015, 12 pages.
Spinelli et al., Intestinal Fibrosis in Crohn's Disease: Medical Treatment or Surgery?, Current Drug Targets, 2010, vol. 11(2), pp. 242-248, abstract only.
Koga et al., Transanal Delivery of Angiotensin Converting Enzyme Inhibitor Prevents Colonic Fibrosis in a Mouse Colitis Model: Development of a Unique Mode of Treatment, Surgery, 2008, vol. 144(2), pp. 259-268.
Parente et al., Bowel Ultrasound in Assessment of Crohn's Disease and Detection of Related Small Bowel Strictures: A Prospective Comparative Study Versus X Ray and Intraoperative Findings, Gut, 2002, vol. 50, pp. 490-495.
Strober et al., Pro-Inflammatory Cytokines in the Pathogenesis of IBD, Gastroenterology, 2011, vol. 140(6), pp. 1756-1767.
Fitzpatrick, LR, Novel Pharmacological Approaches for Inflammatory Bowel Disease: Targeting Key Intracellular Pathways and the IL-23/IL-17 Axis, International Journal of Inflammation, vol. 2012, pp. 1-8.
Puinchuk et al., Human Colonic Myofibroblast Promote Expansion of CD4+ CD25high Foxp3+ Regulatory T Cells, Gastroenterology, 2011, vol. 140(7), pp. 2019-2030, pp. 1-19, and p. 8.
Australian Patent Application No. 2014241162 Office Action dated Apr. 16, 2018.
Chinese Patent Application No. 2014800301280 Second Office Action dated Jan. 19, 2018.
Clarke et al. An anti-TL1A antibody for the treatment of asthma and inflammatory bowel disease. MAbs 10(4):664-677 (2018).
Erpenbeck et al. Segmental allergen challenge in patients with atopic asthma leads to increased IL-9 expression in bronchoalveolar lavage fluid lymphocytes. J Allergy Clin Immunol 111(6):1319-1327, 2003.
European Patent Application No. 14773989.0 Communication dated Nov. 17, 2017.
European Patent Application No. 14797214.5 Office Action dated Apr. 19, 2018.
Hsu et al. The tale of TL1A in inflammation. Mucosal Immunol 4(4):368-370, 2011.
Japanese Patent Application No. 2016-505570 Office Action dated Dec. 4, 2017.
Kakuta et al., Su1746 Rare Variants of TNFSF15 Are Significantly Associated With Crohn's Disease in Non-Jewish Caucasian Independent of the Known Common Susceptibility SNPs, Gastroenterology, 144(5):S-466, 2013.
Kim et al. Effects of IL-9 blockade on chronic airway inflammation of murine asthma models. Allergy: Eur J Allergy Clin Immunol Suppl 96(67):448, Nov. 2012.
Kim et al. Effects of interleukin-9 blockade on chronic airway inflammation in murine asthma models. Allergy Asthma Immunol Res 5(4):197-206, 2013.
Shin et al. Reversal of murine colitis and fibrosis by neutralizing TL1A antibody: potential novel therapy to alter natural history of Crohn's disease. Gastroenterol 142(5):S84, Abstract #357, 2012.
U.S. Appl. No. 14/900,024 Office Action dated Apr. 16, 2018.
U.S. Appl. No. 15/245,875 Office Action dated Jun. 12, 2018.
Yagi et al., Interleukin-31 stimulates production of inflammatory mediators from human colonic subepithelial myofibroblasts. International Journal of Molecular Medicine, 19:941-946, 2007.
Yang et al., Association of TNFSF15 with Crohn's Disease in Koreans, American Journal of Gastroenterology 2008;103:1437-1442.
Adler et al. Anti-tumor necrosis factor [alpha] prevents bowel fibrosis assessed by messenger RNA, histology, and magnetization transfer MRI in rats with Crohn's disease. Inflamm Bowel Dis 19(4):683-690 (2013).
Aggarwal et al. The Role of TNF and its Family Members in Inflammation and Cancer: Lessons from Gene Deletion, CLUT. Drug Targets Inflamm. Allergy, 1(4):327-341, 2002.
Ahmad et al., Clinical relevance of advances in genetics and pharmacogenetics of IBD. Gastroenterology, 126:1533-1549, 2004.
Ahn et al., The First Korean Genome Sequence and Analysis: Full Genome Sequencing for a Socio-Ethnic Group, Genome Res., 2009, vol. 19, pp. 1622-1629.
Aiba et al., The role of TL1A and DR3 in autoimmune and inflammatory diseases. Mediators Inflamm. 2013:#258164, 9 pages.
Akbas et al., Screening for Mutations of the HFE Gene in Parkinson's Disease Patients with Hyperechogenicity of the Substantia Nigra, Neuroscience Letters, 2006, vol. 407, pp. 16-19.
Al-lazikani et al., Standard conformations for the canonical structures of immunoglobulins. J. Molec. Biol. 273:927-948, 1997.
Alvarez-Lobos et al., Crohn's Disease patients carrying Nod2/CARD15 gene variants have an increased and early need for first surgery due to stricturing disease and higher rate of surgical recurrence. Ann Surg, 242:693-700, 2005.
Andus et al., Measurement of TNFalpha mRNA in lamina propia lymphocytes (LPL) isolated from mucosal biopsies by quantitative polymerase chain reaction (PCR). Cytokines and cytokine receptor in mucosal immunity Abstract# 2742 p. A1409 (1992).
Annese et al., Variants of CARD15 are Associated with an Aggressive Clinical Course of Crohn's Disease—An IG-IBD Study, American Journal of Gastroenterology, 2005, vol. 100, pp. 84-92.
Australia Patent Application No. 13576/1997 Office Action dated Jul. 7, 1999.
Australia Patent Application No. 13576/1997 Office Action dated Jul. 20, 2000.
Australia Patent Application No. 13576/1997 Office Action dated Sep. 7, 2000.
Australia Patent Application No. 2005314089 Office Action dated Jul. 8, 2010.
Australia Patent Application No. 2638495 Office Action dated Sep. 19, 1997.
Badger et al., Idoxifene, a novel selective estrogen receptor modulator is effective in a rat model of adjuvant-induced arthritis. J Pharmacology and Experimental Therapeutics vol. 291 pp. 1380-1386 1999.
Bamias et al., Circulating levels of TNF-like cytokine 1A (TL1A) and its decoy receptor 3 (DcR3) in rheumatoid arthritis. Clin. Immunol., 129:249-255, 2008.
Barrett et al., Genome-Wide Association Defines More than 30 Distinct Susceptibility Loci for Crohn's Disease, Nature Genetics, 2008, vol. 40(8), pp. 955-962.
Barrett et al., In Vivo constitutive expression of an IBD associated gene TNFSF15 causes severe inflammation and induces fibrostenotic disease in 2 marine models of chronic colitis. Gastroenterology, 140(5):Supplement 1, S-151, Abstract 925, 2011.
Bauer et al., A genetic enrichment for mutations constructed by oligodeoxynucleotide-directed mutagenesis. Gene, 37:73-81, 1985.
Benedict et al., Immunoglobulin Kappa light chain variable region, Partial (Mus musculus). GenBank: AAD39789.1, Jul. 26, 2016, 1 page.
Benner et al., Evolution, Language and Analogy in Functional Genomics, Trends in Genetics, 2001, vol. 17, pp. 414-418.
Biener-Ramanujan et al., Functional Signaling of Membrane-Bound TL1A Induces IFN-gamma Expression, Jun. 3, 2010, p. 2376-2380.
Bird et al., Single-chain antigen-binding proteins. Science, 242:423-42, 1988.
Birren et al., GeneBank Accession No. AC021483 retrieved from: http://www.ncbi.nlm.nih.gov/nuccore/AC021483 on Aug. 30, 2012.
Birren et al., GeneBank Accession No. AC026826 retrieved from: http://www.ncbi.nlm.nih.gov/nuccore/AC026826 on Aug. 30, 2012.

(56) References Cited

OTHER PUBLICATIONS

Birren et al., GeneBank Accession No. AC105243 retrieved from: http://www.ncbi.nlm.nih.gov/nuccore/AC105243 on Aug. 30, 2012.
Bomprezzi et al., Gene Expression Profile in Multiple Sclerosis Patients and Healthy Controls: Identifying Pathways Relevant to Disease, Human Molecular Genetics, 12 (17): 2191-2199, 2003.
Bossuyt et al., Serologic markers in inflammatory bowel disease. Clinical Chemistry, 52(2):171-181, 2006.
Brambs et al., Inflammatory Bowel Disease: Radiographical diagnostics. (reprints available at the Department of Radiography, Albert Ludwigs University Hospital, Freiburg, Federal Republic of Germany 3-49 (2009), 19th Ed. , Falk Foundation.
Brand, Crohn's Disease: Th1, Th17 or both? The Change of a Paradigm: New Immunological and Genetic Insights implicate Th17 Cells in the Pathogenesis of Crohn's Disease, GUT, 58(8):1152-1167, 2009.
Braun et al., Chapter 13: Multiparameter analysis of immunogenetic mechanisms in clinical diagnosis and management of inflammatory bowel disease. Immune mechanisms in inflammatory bowel disease edited by Richard S. Blumberg and Markus F. Neurath Mar. 10, 2006, Springer first edition: pp. 209-218.
Brennan et al. Preparation of bispecific antibodies by chemical recombination of monoclonal immunoglobulin G$_{1}$ fragments. Science 229:81-83, 1985.
Brinar et al., P217—Genetic Variants in Autophagy Related Genes and Granuloma Formation in Patients with Crohn's Disease, Journal of Crohn's and Colitis, 2009, vol. 3(1), p. S96.
Brummell et al. Probing the combining site of an anti-carbohydrate antibody by saturation-mutagenesis: Role of the heavy-chain CDR3 residues. Biochem. 32: 1180-1187, 1993.
Burks et al., In vitro scanning saturation mutagenesis of an antibody binding pocket. Proc. Natl. Acad. Sci. USA 94:412-417, 1997.
Canada Patent Application No. 2830365 first substantive Examiner's Report dated Feb. 8, 2018.
Canadian Patent Application No. 2,183,147 Office Action dated Apr. 1, 2005.
Canadian Patent Application No. 2,183,147 Office Action dated Mar. 20, 2006.
Canadian Patent Application No. 2,183,147 Office Action dated Jun. 20, 2007.
Canadian Patent Application No. 2,589,746 Office Action dated Aug. 3, 2010.
Canadian Patent Application No. 2,589,746 Office Action dated May 9, 2011.
Cardullo, et al. Detection of nucleic acid hybridization by nonradiative fluorescence resonance energy transfer. Proc Natl Acad Sci U S A. Dec. 1988;85(23):8790-4.
CBI SNP ID rs11209063, 2006, retrieved from: http://www.ncbi.nlm.nih.gov/projects/SNP/snp_ref.cgi?rs=11209063 (3 pgs.).
CBI SNP ID rs12495640, 2006, retrieved from: http://www.ncbi.nlm.nih.gov/projects/SNP/snp_ref.cgi?rs=12495640 (3 pgs.).
CBI SNP ID rs1495964, 2006, retrieved from: http://www.ncbi.nlm.nih.gov/projects/SNP/snp_ref.cgi?rs=1495964 (3 pgs.).
CBI SNP ID rs1908632, 2006, retrieved from: http://www.ncbi.nlm.nih.gov/projects/SNP/snp_ref.cgi?rs=1908632 (3 pgs.).
CBI SNP ID rs6788981, 2006, retrieved from: http://www.ncbi.nlm.nih.gov/projects/SNP/snp_ref.cgi?rs-6788981 (3 pgs.).
CBI SNP ID rs7374667, 2006, retrieved from: http://www.ncbi.nlm.nih.gov/projects/SNP/snp_ref.cgi?rs=7374667 (4 pgs).
Center for Disease Control and Prevention (CDC) "Inflammatory Bowel Disease (IBD)" retrieved from: http://www.cdc.gov/ibd/ on Sep. 3, 2013.
Chebli et al., Azathioprine Maintains Long-Term Steroid-Free Remission Through 3 Years in Patients with Steroid-Dependent Ulcerative Colitis, Inflammatory Bowel Disease, 2010, vol. 16(4), pp. 613-619.
Chen et al. Screening for genes associated with cardiac fibrosis induced by aldosterone. Xi Bao Yu Fen Zi Mian Yi Xue Za Zhi Journal of Cellular and Molecular Immuno 28(4):350-353 (English Abstract).
Chevillard et al. Two new polymorphisms in the human interferon gamma promoter. Eur J Immunogenetics vol. 29 pp. 52-56 2002.
Cho, The Genetics and Immunipathogenesis of Inflammatory Bowel Disease, Nature Reviews, 2008, vol. 8, pp. 158-466.
Cippitelli et al. Retinoic acid-induced transcriptional modulation of the human interferon gamma promoter. J Biol Chemistry vol. 271 pp. 26783-26793 1996.
Clunie et al., Relevance of Thiopurine Methyltransferase Status in Rheumatology Patients Receiving Azathioprine, Rheumatology, 2004, vol. 41(1), pp. 13-18.
CN Application No. 201480030128.0 Third Office Action dated Sep. 4, 2018.
Cooper et al., Systematic Assessment of Copy Number Variant Detection Via Genome-Wide SNP Genotyping, Nature Genetics, 2008, vol. 40, pp. 1199-1203.
Corominas et al., Allelic Variants of the Thiopurine S-Mehtyltransferase Deficiency in Patients with Ulcerative Colitis and in Healthy Controls, 2000, vol. 95(9), pp. 2313-2317.
Craik, Charles. Use of oligonucleotides for site-specific mutagenesis. BioTechniques 1985 :12-19, 1985.
DbSNP Short Genetic Variations. Reference SNP(refSNP) Cluster Report: rs4855535. Printed Sep. 10, 2013, 5 pages. www.ncbi.nlm.nih.gov.
DbSNP, Short Genetic Variations, Submitted SNP(ss) Details: ss70756257,, Apr. 27, 2007, 1 page. https://www.ncbi.nlm.nih.gov.
De Domenico et al., The Molecular Basis of Ferroportin Linked Hemochromatosis, Proc Natl Acad Sci USA, 2005, vol. 102(25), pp. 8955-8960.
Diaz-Gallo et al. Differential association of two PTPN22 coding variants with Crohn's disease and ulcerative colitis. Inflammatory Bowel Diseases, vol. 17, No. 11, pp. 2287-2294, 2011.
Drach et al., Interphase Fluorescence in Situ Hybridization Identifies Chromosomal Abnormalities in Plasma Cells from Patients with Monoclonal Gammopathy of Undetermined Significance, Blood, 1995, vol. 86, pp. 3915-3921.
Dubinsky et al. Synergism of NOD2 and ASCA (Anti-Saccharomyces Cerevisiac Antibodies) Contributes to Disease Behavior in Pediatric Crohn's Disease (CD) Patients. Gastroenterology (2003): 124 (Suppl): M1556.
Duerr et al., A Genome-Wide Associate Study Identifies IL23R as an Inflammatory Bowel Disease Gene, Science, 2006, vol. 314, pp. 1461-1463.
Eggena et al., Identification of Histone H1 as a Cognate Antigen of the Ulcerative Colitis-Associated Marker Antibody pANCA, Journal of Autoimmunity, 2000, vol. 14, pp. 83-97.
Elgert, K., Immunology: Understanding the immune system. Wiley-Liss: New York, 1996, p. 323.
EP 12762965.7 Extended European Search Report dated Mar. 24, 2015.
EP 12764214.8 Extended European Search Report dated Nov. 18, 2014.
EP 12765854 Extended European Search Report dated Mar. 18, 2015.
EP 12765854.0 Partial Supplementary Search Report dated Nov. 24, 2014.
EP 2762965.7 Partial Supplementary Search Report dated Nov. 26, 2014.
European Patent Application No. 05853294 Further Examination Report dated Apr. 30, 2009.
European Patent Application No. 95921264.8 Communication dated Feb. 29, 2000.
European Patent Application No. 95921264.8 Communication dated Feb. 24, 1999.
European Patent Application No. 05853294 European Search Report dated Apr. 29, 2008.
European Patent Application No. 05853294 Office Action dated May 15, 2008.
European Patent Application No. 06772657 ESR dated Dec. 2, 2008.
European Patent Application No. 10171757 European Search Report dated Nov. 10, 2010.
European Patent Application No. 14773989.0 Office Action dated Aug. 10, 2018.

(56) References Cited

OTHER PUBLICATIONS

European Patent Application No. 14798650.9 Communication dated Jan. 10, 2018.
European Patent Application No. 14826746.1 Communication dated Dec. 8, 2017.
European Patent Application No. 14842590 Extended European Search Report dated Apr. 4, 2017, 10 pages.
Evans et al., Pharmacogenomics: Translating Functional Genomics into Rational Therapeutics, Science, 1999, vol. 286(5439), pp. 487-491.
Fang et al., Essential role of TNF receptor superfamily 25 (TNFRS25) in the development of allergic lung inflammation. J.Exp. Med., 205(5):1037-1048, 2008.
Fawcett et al., Molecular cloning of ICAM-3, a third ligand for LFA-1, constitutively expressed on resting leukocytes. Nature 360:481-4. (1992).
Forcione, Anti-Saccharmyces Cerevisiae Antibody (ASCA) Positivity is Associated with Increased Risk for Early Surgery in Crohn's Disease, Gut, 2004, vol. 53(8), pp. 1117-1122.
Franke et al., Genome-Wide Meta-Analysis Increases to 71 the Number of Confirmed Crohn's Disease Susceptibility Loci, Nature Genetics, 2010, vol. 42(12), pp. 1118-1125.
Franke et al., Replication of Signals from Recent Studies of Crohn's Disease Identifies Previously Unknown Disease _oci for Ulcerative Colitis, Nature Genetics, 2008, vol. 40(6), pp. 713-715.
Garcia-Bates et al., GeneBank NM_001198.3, *Homo sapiens* PR Domain Containing 1, with ZNF Domain (PRDM1), Transcript Variant 1, mRNA, 2010 retrieved from: http://www.ncbi.nlm.nih.gov/nuccore/172072683? sat=13&satkey=10378402 on Jul. 7, 2011.
Garcia-Bates et al., Peroxisome Proliferator-Activated Receptor Gamma Ligands Enhance Human B Cell Antibody Production and Differentiation, J Immunology, 2009, vol. 183, pp. 6903-6912.
GenBank Accession No. AF134726 (72 pgs.) (Mar. 27, 1999).
GenBank Accession No. AC007728 (31 pgs.) (Jun. 1, 2001).
GenBank Accession No. AF129756.1 (70 pgs.) (revised Nov. 12, 1999).
GenBank Accession No. AF385089 (3 pgs.) (Jul. 4, 2001).
GenBank Accession No. AF513860 (12 pgs.) Jul. 9, 2002).
GenBank Accession No. AX259776 (21 pgs.) (Oct. 26, 2001).
GenBank Accession No. NM022162 (5 pgs.) (Sep. 11, 2011).
GenBank Accession No. U89335 (25 pgs.) (Oct. 22, 1999).
GenBank Accession No. U89336 (27 pgs.) (Feb. 14, 1997).
GenBank AF252829.4 (49 pgs.) (Nov. 8, 2002).
Gene Card for 1L12B(p40) (http://www.genecards.org/cgi-bin/carddisp.pl?gene=1L12B&keywords=i112b) accessed May 8, 2017.
Gene Card for IL17RD (http://www.genecards.org/cgi-bin/carddisp.pl?gene=1L17RD&search=il17rd) accessed May 14, 2013.
Gene Card for IL17RD retrieved from: http://www.genecards.org/cgi-bin/carddisp.pl?gene=1L17RD&dearch=i117rd (Accessed May 2013).
GeneBank Accession No. AF450133 (10 pgs.) (Dec. 27, 2001).
GeneCard DR3 found at http://www.genecards.org/cgi-bin/carddisp.pl?gene=TNFRSF25&search=DR3 on Jan. 1, 2013.
GeneCard NOD2 gene (16 pgs) (Last update Jul. 2, 2009).
GeneCards, BRWD1 Gene-GeneCards | BRWD1 Protein | BRWD1 Antibody. Printed Sep. 10, 2013, 11 pages. www.genecards.org.
GeneCards for JAK2 retrieved from: http://www.genecards.org/cgi-bin/carddisp.pl?gene=JAK2&search=jak2 on Jun. 8, 2013.
GeneCards for SMAD3 retrieved from: http://www.genecards.org/cgi-bin/carddisp.pl?gene=SMAD3&search=smad3 on Jun. 8, 2013.
GeneCards for TAGAP retrieved from: http://www.genecards.org/cgi-bin/carddisp.pl?gene=TAGAP&sup=236&earch=tagap on Aug. 22, 2013.
GeneCards for TPMT retrieved from: http://www.genecards.org/cgi-bin/carddisp.pl?gene=TPMT&search=tpmt on Aug. 30, 2013.
Ghosh et al., Natalizumab for active Crohn's disease. The New England Journal of Medicine, 348:24-32, 2003.
Gianfrancesco et al., Identification of a Novel Gene and a Common Variant Associated with Uric Acid Nephrolithiasis in a Sardinian Genetic Isolate, Am. J. Hum. Genet., 2003, vol. 72, pp. 1479-1491.
Gonsky et al., An IFNG SNP Within a Linkage Disequilibrium Block Associated with UC and Severity is Functionally Associated with Altered IFNG Methylation and IGN--v Protein Secretion, Gastroenterology, 2011, vol. 140(1) p. S-835.
Gonsky et al., Distinct Methylation of IFNG in the Gut, Journal of Interferon and Cytokine Research, 2009, vol. 29(7), pp. 407-414.
Gonsky et al., Gastroenterology; AGA Abstracts, vol. 140, Supplement 1, p. S-835; May 2011.
Gout et al., Death receptor-3, a new e-selectin counter-receptor that confers migration and survival advantages to colon carcinoma cells by triggering p38 and ERK MAPK activation. Cancer Research, 66(18):9117-9124, 2006.
Hampe et al., A Genome-Wide Association Scan of Nonsynonumous SNPs Identifies a Susceptibility Variant for Crohn Disease in ATG16L1, Nature Genetics, 2007, vol. 39, pp. 207-211.
Haritunians et al., Genetic Predictors of Medically Refractory Ulcerative Colitis, Inflamm Bowel Dis., 2010, vol. 16 ;11), pp. 1830-1840.
Hazra et al., Common Variants of FUT2 are Associated with Plasma Vitamin B12 Levels, Nature Genetics, 2008, vol. 40, pp. 1160-1162.
Hegele, R., SNP Judgments and Freedom of Association, Arteriosclerosis, Thrombosis, and Vascular Biology, 2002, vol. 22, pp. 1058-1061.
Heyman et al., Children with Early-Onset Inflammatory Bowel Diseas (1BD): Analysis of a Pediatric 1BD Consortium Registry, Journal of Pediatrics, 2005, vol. 146, pp. 35-40.
Hirschhorn et al., A Comprehensive Review of Genetic Association Studies, Genetics in Medicine, 2002, vol. 4(2) pp. 45-61.
Hodgson, John. Making monoclonals in microbes. Bio/Technology 9:421-425, 1991.
Hoh et al., Trimming, Weighting and Grouping SNPs in Human Case-Control Association Studies, Genome Research, 2001, vol. 1, pp. 2115-2119.
Holliger and Hudson. Engineered antibody fragments and the rise of single domains. Nat. Biotechnol. 23(9):1126-36, 2005.
Honkanen et al., Coxsackievirus up-regulates IL-17 immunity in human type 1 diabetes. Diabetologia, 54:Supp. 1, S1, Abstract S421, 2009.
Hugot et al., Association of NOD2 Leucine-Rich Repeat Variants with Susceptibility to Crohn's Disease, Nature, 2001, vol. 411, pp. 599-603.
Hunt et al., Newly Identified Genetic Risk Variants for Cellac Disease Related to the Immune Response, Nature Genetics, 2008, vol. 40(4), pp. 395-402.
Huse et al. Generation of a large combinatorial library of the immunoglobulin repertoire in phage lambda. Science 246:1275-1281, 1989.
Huston et al. Protein engineering of antibody binding sites: Recovery of specific activity in an anti-digoxin single-chain Fv analogue produced in *Escherichia coli*. Proc. Natl. Acad. Sci. USA 85:5879-5883, 1988.
Ilumina Press Release dated Jan. 12, 2006, retrieved from: http://investor.illumina.com/phoenix.zhtml?=121278<p=irol-newsArticle&ID=8033958thighlight=.
Ioannidis, J., Why Most Published Research Findings are False, PLoS Med, 2005, vol. 2(8):e124, pp. 0696-0701.
Ioannidis, Replication Validity of Genetic Association Studies, Nature Genetics, 2001, vol. 29, pp. 306-309.
Israel Patent Application No. 244427 Office Action dated Feb. 4, 2018.
Israeli et al., Anti-Saccharomyces Cerevisiar and Antineutrophil Cytoplasmic Antibodies as Predictors of Inflammatory Bowel Disease, Gut, 2005, vol. 54(9), pp. 1232-1236.
Japanese Patent Application No. 2016-514143 Office Action dated Apr. 2, 2018.
Jikihara et al., Interferon-y Inhibits the Synthesis and Release of Renin from Human Decidual Cells, Biology of Reproduction, 54:311-1316, 1996.
Johnson, GeneBank Accession No. AL357075 retrieved from: http://www.ncbi.nlm.nih.gov/nuccore/AL357075 on Aug. 30, 2012.
Johnson, GeneBank Accession No. AL357149 retrieved from: http://www.ncbi.nlm.nih.gov/nuccore/AL357149 on Aug. 30, 2012.

(56) References Cited

OTHER PUBLICATIONS

Jones et al. Replacing the complementarity-determining regions in a human antibody with those from a mouse. Nature 321:522-525, 1986.
Jung et al., Genotype/Phenotype analyses for 53 Crohn's disease associated genetic polymorphisms. PLOS/One, 7(12):e52223, 2012.
Juppner, H. Functional properties of the PTH/PTHrP receptor. Bone, 17(2):395-425, 1995.
Karpuzoglu-Sahin et al., Effects of long-term estrogen treatment on IFN-gamma, IL-2 and IL-4 gene expression and protein synthesis in spleen and thymus of normal C57BL/6 mice. Cytokine vol. 14 pp. 208-217(2001(.
Karpuzoglu-Sahin et al., Interferon-gamma levels are upregulated by 17-beta-estradiol and diethylstibestrol. J Reproductive Immunology 52:113-127 (2001).
Kasvosve et al., Effect of Ferroportlin Q248H Polymorphism on Iron Status in African Children, Am J Clin Nutr, 2005, vol. 82(5), pp. 1102-1106.
Kaul et al., GeneBank Accession No. AL107626 retrieved from: http://www.ncbi.nlm.nih.gov/nuccore/AL107626 on Aug. 30, 2012.
Kite et al., Use of in vivo-generated biofilms from hemodialysis catheters to test the efficacy of a novel antimicrobial catheter lock for biofilm eradication in vitro. J Clin Microbiol., 42.7 (2004): 3073-3076.
Kobayashi et al. Tryptophan H33 plays an important role in pyrimidine (6-4) pyrimidone photoproduct binding by a high-affinity antibody. Protein Eng. 12(10):879-884, 1999.
Kohler and Milstein, Derivation of specific antibody-producing tissue culture and tumor lines by cell fusion. Eur. J. Immunol. 6: 511-519, 1976.
Kumar et al., A Single Nucleotide Polymorphism (A-G) in Intron 3 of IFNi Gene is Associated with Asthma, Genes and Immunity, 2008, vol. 9, pp. 294-301.
Tromm et al., Inflammatory Bowel Disease: endoscopic diagnostics. (Reprints available at the Department of Gastroenterology and Hepatology "Bergmannshell" Hospital, University of Bochum, Federal Republic of Germany pp. 3-38 (2009), 19th Ed., Falk Foundation.
Lal et al., Antibiotic Therapy for Crohn's Disease: A Review, Canadian Journal of Gastroenterology, 2006, vol. 20(10), pp. 651-655.
Lambert, Missing Heritability and the Future of GWAS, Golden Helix, Retrieved from Goldenhelix.com, http://blog.goldenhelix.com/clambert/missing-heritability-and-the-future-of-gwas/, Aug. 2006.
Landegren et al. A Ligase-Mediated Gene Detection Technique. Science 241:1077-1080 (1988).
Lawrance et al., Ulcerative Colitis and Crohn's Disease: Distinctive Gene Expression Profiles and Novel Susceptibility Candidate Genes, Human Molecular Genetics, 10(5):445-456, 2001.
Lee et al., SLC40A1 c.1402G/A Results in Aberrant Splicing, Ferroportin Truncation after Glycine 330 and an Autosomal Dominant Hemochromatosis Phenotype, Acta Haematol, 2007, vol. 118(4), pp. 237-241.
Leong et al., NOD2/CARD15 Gene Polymorphisms and Crohn's Disease in the Chinese Population, Aliment Pharmacol Thera, 17:1465-1470, 2003.
Leppkes et al., RORy-expressing Th17 cells induce murine chronic intestinal inflammation via redundant effects of IL-17A and IL-17F. Gastroenterology, 136:257-267, 2009.
Li et al. TNFRSF1B Is Associated with ANCA in IBD. Inflammatory Bowel Diseases. 22(6):1346-1352 (2016).
Lipsky, P. Structure, function and regulation of molecules involved in leukocyte adhesion. New York: Springer-Verlag 1993 Book not included.
Liu et al., Mucosal Gene Expression Profiles Following the Colonization of Immunocompetent Defined-Flora C3H Mice wih Helicobacter Bilis: A Prelude to Typhlocolitis, Microbes and Infection, 2009, vol. 11, pp. 374-383.
Livak et al., Allelic Discrimination Using Fluorogenic Probes and the 5' Nuclease Assay, Genetic Analysis, 1999, vol. 14, pp. 143-149.
Lorenz-Meyer. Inflammatory Bowel Disease Laboratory Diagnostics. (Reprints available from the City Hospital, Friedrichshafen, 15th Ed., Falk Foundation, Federal Republic of Germany):3-29 (2008).
Lucentini, J. Gene association studies typically wrong. Scientist, 18(24):20, 2004.
Maggio-Price et al., Helicobacter Infection is Required for Inflammation and Colon Cancer in Smad3-Deficient Mice, Cancer Research, 2006, vol. 66, pp. 828-838.
Maniatis, et al. Molecular Cloning. Cold Spring Harbor Laboratory, Table of Contents only, 1982.
Marrakchi et al., Interleukin 10 promoter region polymorphisms in inflammatory bowel disease in Tunisian population. Inflamm. Res., 58:155-160, 2009.
Martinez et al., Regulation and Function of Proinflammatory TH17 Cells, Animals of the New York Academy of Sciences, 1143(1):188-211, 2008.
Martins et al., Transcriptional Repressor Blimp-1 Regulates T Cell Homeostasis and Function, Nature Immunol, 2006, vol. 7(5), pp. 457-465.
May, How Many Species are there on Earth?, Science, 1988, vol. 241, p. 1441.
Medrano et al. Role of TNFRSF1B polymorphisms in the response of Crohn's disease patients to infliximab. Human Immunology 75(1):71-75 (2014).
Migone et al., TL1A is a TNF-like Ligand for DR3 and TR6/DcR3 and Functions as a T cell Costimulator, Immunity, Mar. 16, 2002, pp. 479-492.
Modiano et al., Intestinal Granulomas in Crohn's Disease: Association with Patient Characteristics, Serologic Markers and Genetics, Gastroenterology 2011, vol. 140(5), pp. 5484.
Morimoto et al. Single-step purification of F(ab')2 fragments of mouse monoclonal antibodies (immunoglobulins G1) by hydrophobic interaction high performance liquid chromatography using TSKgel Phenyl-5PW. Journal of Biochemical and Biophysical Methods 24:107-117, 1993.
Morinaga et al., Database Uniprot (online), Mar. 8, 2011, Database Accession No. P02771.
Morinaga et al., Primary Structures of Human alpha.-fetoprotein and it mRNA, PNAS, 1983, vol. 80, pp. 4604-4608.
Morinaga et al., UniProt Accession No. P02771 retrieved from: http://www.uniprot.org/uniprot/P02771.txt?version=122 on Mar. 8, 2011.
Mummidi et al., Evolution of human and non-human primate CC chemokine receptor 5 gene and mRNA. Journal of Biological Chemistry, 275(5):18946-18961 (2000).
Mundwiler et al., Inflammatory Bowel Disease Serologies in Ankylosing Spondylitis Patients: A Pilot Study, Arthritis Research and Therapy, 2009, vol. 11(6), pp. 2-8.
NCBI Accession No. NM_001198.3 (5 pgs.) (Mar. 4, 2010).
NCBI Reference Sequence AC_000138.1 *Homo sapiens* Chromosome 6, Alternate Assembly (based on HuRef), Whole Genome Shotgun Sequence retrieved on Mar. 3, 2008.
NCBI Reference SNP Cluster Report ID rs2241880; Retrieved from: http://www.ncbi.nlm.nih.gov/projects/SNP/snp_ref. .1gi?rs=2241880 on Sep. 23, 2016; 5 pages.
"NCBI Reference SNP Cluster Report ID rs2836878; Retrieve from: http://www.ncbi.nlm.nih.gov/projects/SNP/snp_ref. .1gi?rs=2836878 on Sep. 23, 2016; 3 pages.".
NCBI Reference SNP Cluster Report ID rs3764147; Retrieved from: http://www.ncbi.nlm.nih.gov/projects/SNP/snp_ref. .1gi?rs=3764147 on Sep. 23, 2016; 4 pages.
NCBI Reference SNP Cluster Report ID rs762421; Retrieved from: http://www.ncbi.nlm.nih.gov/projects/SNP/snp_ref. .1gi?rs=762421 on Sep. 23, 2016; 4 pages.
NCBI Reference SNP Cluster Report ID rs9271568; Retrieved from: http://www.ncbi.nlm.nih.gov/projects/SNP/snp_ref. .1gi?rs=9271568 on Sep. 23, 2016; 3 pages.
NCBI Reference SNP Cluster Report: rs13148469 retrieved from: https://www.ncbi.nlm.nih.gov/projects/SNP/snp_ref.cgi?rs=13148469 on Aug. 28, 2012.

(56) References Cited

OTHER PUBLICATIONS

NCBI Reference SNP Cluster Report: rs1861493 obtained from: https://www.ncbi.nlm.nih.gov/projects/SNP/snp_ref.cgi?rs=1861493 on Aug. 28, 2012.
NCBI Reference SNP Cluster Report: rs1861494 retrieved from: http://www.ncbi.nlm.nih.gov/projects/SNP/snp_ss.cgi?subsnp_id=2735497 on Aug. 28, 2012.
NCBI Reference SNP Cluster Report: rs212388 retrieved from: http://www.ncbi.nlm.nih.gov/projects/SNP/snp_ref.cgi?searchType=adhoc_search&type=rs&rs=rs212388 on Sep. 4, 2013.
NCBI Reference SNP Cluster Report: rs282792 retrieved from: https://www.ncbi.nlm.nih.gov/projects/SNP/snp_ref.cgi?rs=282792 on Aug. 28, 2012.
NCBI Reference SNP Cluster Report: rs7071642 retrieved from: http://www.ncbi.nlm.nih.gov/projects/SNP/snp_ss.cgi?subsnp_id=106682238 on Apr. 20, 2011.
NCBI Reference SNP Cluster Report: rs7076156 retrieved from: https://www.ncbi.nlm.nih.gov/projects/SNP/snp_ref.cgi?rs=7076156 on Apr. 20, 2011.
NCBI Reference SNP Cluster Report: rs7596205 retrieved from http://www.ncbi.nlm.nih.gov/projects/SNP/snp_ref.cgi?rs=7596205 on Nov. 2, 2009.
NCBI SNP 10 rs12638201 (1 pg.) (Jan. 31, 2001).
NCBI SNP 10 rs2066844 (1 pg.) (created May 2, 1997).
NCBI SNP 10 rs2066845 (1 pg.) (created May 2, 1997).
NCBI SNP 10 rs2302600 (1 pg.) (Feb. 15, 1996).
NCBI SNP 10 rs746503 (1 pg.) (Dec. 7, 2000).
NCBI SNP 10 rs7613548 (1 pg.) (created Apr. 19, 2000).
NCBI SNP ID rs11209063.
NCBI SNP ID rs12495640.
NCBI SNP ID rs1495964.
NCBI SNP ID rs1908632.
NCBI SNP ID rs2066847 (1 pg.) (created May 2, 1997).
NCBI SNP ID rs6788981.
Onnie et al., Diverse Effects of the CARD15 and IBD5 Loci on Clinical Phenotype in 630 Patients with Crohn's Disease, European Journal of Gastroenterology and Hepatology, 2008, vol. 20(1), pp. 37-45.
Oshitani, et al., Cross-Reactivity of Yeast Antigens in Human Colon and Peripheral Leukocytes, The Journal of Pathology, 2003, vol. 199(3), pp. 361-367.
Pallone et al., Genetic and Pathogenetic Insights into Inflammatory Bowel Disease, Current Gastroenterology Reports, 2003, vol. 5, pp. 487-492.
Papadakis et al., TL1A Synergizes with IL-12 and IL-18 to Enhance IFN-gamma Production in Human T Cells and NIK Cells, J Immunol, 172(11):7002-7007, 2004.
Pappu et al., TL1A-DR3 interaction regulates Th17 cell function and Th17-Mediated autoimmune disease. Journal of Experimental Medicine, 205(5):1049-1062, 2008.
PCT/2011/028694 International Preliminary Report on Patentability dated Sep. 18, 2012.
PCT/2011/028694 International Search Report and Written Opinion dated Jul. 27, 2011.
PCT/2012/030614 International Preliminary Report on Patentability dated Nov. 19, 2013.
PCT/2012/030614 International Search Report and Written Opinion dated Sep. 28, 2012.
PCT/US2005/018161 International Preliminary Report on Patentability dated Apr. 15, 2009.
PCT/US2006/22427 International Search Report dated Sep. 5, 2006 EP Application 2006772657.
PCT/US2008/055020 International Preliminary Report on Patentability dated Aug. 26, 2009.
PCT/US2008/055020 International Search Report dated Aug. 14, 2008.
PCT/US2008/055020 Written Opinion dated Aug. 14, 2008.
PCT/US2008/055236 International Preliminary Examination Report dated Sep. 1, 2009.
PCT/US2008/055236 International Search Report and Written Opinion dated Nov. 14, 2008.
PCT/US2008/055236 Written Opinion dated Nov. 14, 2008.
PCT/US2008/057820 Written Opinion dated Sep. 11, 2008.
PCT/US2008/061652 International Preliminary Report on Patentability dated Dec. 1, 2008.
PCT/US2008/062531 International Preliminary Report on Patentability dated Nov. 10, 2009.
PCT/US2008/062531 International Search Report and Written Opinion dated Nov. 18, 2008.
PCT/US2008/062531 Written Opinion dated Nov. 18, 2008.
PCT/US2008/080526 International Preliminary Report on Patentability dated Apr. 20, 2010.
PCT/US2009/044720 International Preliminary Report on Patentability dated Nov. 23, 2010.
PCT/US2009/048319 International Preliminary Report on Patentability dated Jan. 5, 2011.
PCT/US2009/048319 International Search Report and Written Opinion dated Nov. 6, 2009.
PCT/US2009/059190 International Preliminary Report on Patentability dated Apr. 5, 2011.
PCT/US2009/059190 International Search Report and Written Opinion dated Mar. 16, 2010.
PCT/US2009/059190 Written Opinion dated Mar. 16, 2010.
PCT/US2009/061698 International Preliminary Report on Patentability dated Apr. 26, 2011.
PCT/US2009/061698 Written Opinion dated Mar. 16, 2010.
PCT/US2009/065928 International Preliminary Report on Patentability dated May 31, 2011.
"PCT/US2009/065928 International Search Report dated Aug. 3, 2010".
PCT/US2009/065928 Written Opinion dated Aug. 3, 2010.
PCT/US2009/069531 International Preliminary Report on Patentability dated Jun. 29, 2011.
PCT/US2009/069534 International Search Report dated Mar. 4, 2010.
PCT/US2009/069541 International Preliminary Report on Patentability dated Jun. 29, 2011.
PCT/US2009/069541 International Search Report dated Mar. 4, 2010.
PCT/US2010/020921 International Report on Patentability dated Jul. 19, 2011.
PCT/US2010/020921 International Search Report and Written Opinion dated May 5, 2010.
PCT/US2010/030359 International Preliminary Report on Patentability dated Oct. 11, 2011.
PCT/US2010/030359 International Search report and Written Opinion dated Aug. 11, 2010.
PCT/US2010/030359 International Search Report dated Aug. 11, 2010.
PCT/US2010/030359 Written Opinion dated Aug. 11, 2010.
PCT/US2011/021180 International Preliminary Report on Patentability dated Jun. 15, 2011.
PCT/US2011/021180 International Search Report and Written Opinion dated Jun. 15, 2011.
PCT/US2011/021382 International Preliminary Report on Patentability dated Jul. 17, 2012.
PCT/US2011/021382 International Search Report and Written Opinion dated Mar. 15, 2011.
PCT/US2011/028694 International Search Report dated Jul. 27, 2011.
PCT/US2012/030611 International Preliminary Report on Patentability dated Oct. 1, 2013.
PCT/US2012/030611 International Search Report dated Sep. 7, 2012.
PCT/US2012/030611 Written Opinion dated Sep. 7, 2012.
PCT/US2012/030616 International Preliminary Report on Patentability dated Nov. 19, 2013.
PCT/US2012/030616 International Search Report and Written Opinion dated Sep. 17, 2012.
PCT/US2014/038333 International Preliminary Report on Patentability dated Nov. 17, 2015.

(56) References Cited

OTHER PUBLICATIONS

PCT/US2014/038333 International Search Report dated Nov. 20, 2014.
PCT/US2014/038333 Written Opinion dated Nov. 20, 2014.
PCT/US2014/054425 International Preliminary Report on Patentability dated Mar. 8, 2016.
PCT/US2014/054425 International Search Report and Written Opinion dated Dec. 31, 2014.
PCT/US2016/022494 International Search Report and Written Opinion dated Jun. 3, 2016.
PCT/US2016/032180 International Preliminary Report on Patentability dated Nov. 30, 2017.
PCT/US2017/058019 International Search Report and Written Opinion dated Feb. 15, 2018.
PCT/US2018/028397 International Search Report and Written Opinion dated Jul. 9, 2018.
Peltekova et al., Functional Variants of OCTN Cation Transporter Genes are Associated with Crohn Disease, Nature Genetics, 2004, vol. 16(5), pp. 471-475.
Pennisi, E. A Closer look at SNPs suggests difficulties. Science, 281(5384):1787-1789, 1998.
Pericak-Vance et al., Approaches to gene mapping in complex human diseases. Wiley-Liss New York 1998.
Perkin Elmer Catalog 1992, p. 12.
Picornell et al., TNFSF15 is an ethnic specific IBD gene. Inflamm. Bowel Disease, 13(11):1333-1338, 2007.
Pierik et al. Tumour Necrosis Factor-a Receptor 1 and 2 Polymorphisms in Inflammatory Bowel Disease and their Association with Response to Infliximab. Alimentary Pharmacology & Therapeutics 20(3):303-310 (2004).
Prideaux et al., Inflammatory Bowel Disease in Asia: A Systematic Review, Journal of Gastroenterology and -lepatology, 27(8):1266-1280, 2012.
Queen et al. A humanized antibody that binds to the interleukin 2 receptor. Proc. Natl. Acad Sci USA 86:10029-10032, 1989.
Queiroz et al., Immune Response and Gene Polymorphism Profiles in Crohn's Disease and Ulcerative Colitis, Inflammatory Bowel Diseases, 2008, vol. 15, pp. 353-358.
Quinton et al., Anti-Saccharomyces Cerevisiae Mannan Antibodies Combined with Antineutrophil Cytoplasmic Autoantibodies in Inflammatory Bowel Disease, Prevalence and Diagnostic Role, Gut, 1998, vol. 42(6), pp. 788-791.
Raychaudhuri et al., Genetic Variants at CD28, PRDM1 and CD2/CD58 are Associated with Rheumatoid Arthritis Risk, Nature Genetics, 2009, vol. 41(12), pp. 1313-1318, and online methods, 2 pages.
R&D datasheet for human/mouse TL1A/TNFSF15 antibody, catalog No. MAB7441; clone #293327 (Feb. 7, 2018).
Reichwald et al. TL1A induces TCR independent IL-6 and TNF-alpha production and growth of PLZF leukocytes. PLOS ONE 9(1):e85793, 2013.
Relling et al., Mercaptopurine Therapy Intolerance and Heterozygosity at the Thiopurine S-Methyltransferase Gene Locus, Journal of the National Cancer Institute, 1999, vol. 91(23), pp. 2001-2008.
Richard et al. The TNF-family cytokine TL1A: from lymphocyte costimulator to disease co-conspirator. J Leukocyte Biol 98:333-345 2015.
Riechmann et al. Reshaping human antibodies for therapy. Nature, 332.6162 (1988): 323-7.
Rioux et al., Genetic Variation in the 5q31 Cytokine Gene Cluster Confers Susceptibility to Crohn Disease, Nature Genetics, 2001, vol. 29(2), pp. 223-228.
Rothe et al., The human combinatorial antibody library HuCAL GOLD combines diversification of all six CDRs according to the natural immune system with a novel display method for efficient selection of high-affinity antibodies. J. Mol. Bio. 376:1182-1200, 2008.
Roussomoustakaki et al., Genetic markers may predict disease behavior in patients with ulcerative colitis. Gastroenterology, 112:1845-1853, 1997.
Rueda et al., A Functional Variant of IFN Gamma Gene Associated with Coeliac Disease, Genes and Immunity, 2004, vol. 5, pp. 517-519.
Saruta et al., High frequency haplotypes in the X-chromosome locus TLR8 are associated with both CD and UC in females. Inflammatory Bowel Disease. 15(3):321-327 (2009).
Scientists Discover New Gene Associated with Crohn's Disease. BusinessWire https://www.businesswire.com/news/home/20070124005277/en/Scientists-Discover-New-Gene-Crohns-Disease (Jan. 24, 2017).
Seidelin et al., Upregulation of cIAP2 in Regenerating Coloncytes in Ulcerative Colitis, Virchows Arch, 151:1031-1038, 2007.
Shih et al., Reversal of murine colitis and fibrosis by neutralizing TL1A antibody potential novel therapy to alter natural history of Chron's Disease. AGA Abstracts, Abstract No. 357, PlosOne, Jan. 11, 2011, S-84, 1 page.
Sobrino et al., SNP's in Forensic Genetics: A Review on SNP Typing Methodologies, Forensic Science International, 154:181-194, 2005.
Abraham et al., Haplotypic polymorph isms of the TNFB gene. Immunogenetics 33:50-53 (1991).
Abreu et al., Mutations in NOD2 are associated with fibrostenosing disease in patients with Crohn's disease. Gastroenterology 123:679-688 (2002).
Adam et al., Immune response in cancer. Pharmacology & Therapeutics 99:113-132 (2003).
Adams et al., 3400 new expressed sequence tags identify diversity of transcripts in the human brain. Nature Genetics 4:256-267 (1993).
Ahmad et al. The molecular classification of the clinical manifestations of Crohn's disease. Gasterenterology 122:854-866 (2002).
Ajioka et al., Haplotype analysis of hemochromatosis: evaluation of linkage-disequilibrium approaches and evolution of disease chromosome. Am J Hum Genet 60:1439-1447 (1997).
Akolkar et al., The IBD1 locus for susceptibility to Crohn's disease has a greater impact on Ashkenazi Jews with early onset diabetes. Am J Gastroenterol 96:1127-1132 (2001).
Ames et al., Are vitamin and mineral deficiencies a major cancer risk? Nature 694-704 (2002).
An et al., A tumor necrosis factor a-inducible promoter variant of interferon-g accelerates C04+ T cell depletion in human immunodeficiency virus-1 infected individuals. J Infectious Diseases 188:228-213 (2003).
Ando et al. Triplet repeat polymorphism within the NOTCH4 gene located near the junction of the HLA class II and class III regions in narcolepsy. Tissue Antigens 50:646-649 (1997).
Andus et al., Measurement of TNFalpha mRNA in a small number of cells by quantitative polymerase chain reaction. (PCR) Regional Immunology 5:11-17 (1993).
Annese et al., Genetic analysis in Italian families with inflammatory bowel disease supports linkage to the IB01 locus—a GSIC study. Eur J Hum Genet 7:567-573 (1999).
Aron et al., Analysis of hsp70 gene polymorphism in allergic asthma Allergy 54:165-170 (1999).
Badger et al., Idoxifene, a novel selective estrogen receptor modulator is effective in a rat model of adjuvant-induced arthritis. J Pharmacology and Experimental Therapeutics 291:1380-1386 (1999).
Ballantyne et al., Short communication, assignment of the gene for intercellular adhesion molecule-1 (ICAM-1) to proximal mouse chromosome 9. Genomics 9:547-550 (1991).
Bao et al., Molecular mechanism for gender differences in susceptibility to T Cell mediated autoimmune diabetes in nonobese diabetic mice. J of Immunol 168:5269-5379 (2002).
Becker et al., Clustering of non-major histocompatibility complex susceptibility candidate loci in human autoimmune disease. PNAS USA 95:9979-9984 (1998).
Benoit et al., Presence of somatostatin-28-(1-12) in hypothalamus and pancreas. PNAS USA 79:917-921 (1982).
Beutler et al., Control of cachectin (tumor necrosis factor) synthesis: mechanisms of endotoxin resistance. Science 232:977-980 (1986).

(56) References Cited

OTHER PUBLICATIONS

Bioque et al., Further evidence for a genetic association of interleukin-1 receptor antagonist and ulcerative colitis in the Northern and Mediterranean population. Gastroenterology 108:a783 (1995) Abstract only.
Boirivant et al., Hypoproliferative human lamina propia T cells retain the capacity to secrete lymphokines when stimulated via CD2/CD28 pathways. Proceedings of the association of American physicians Abstract Only Proc Assoc Am Physicians 108:55-67 (1996).
Bourinbaiar et al., Pregnancy hormones, estrogen and progesteron prevent HIV-1 synthesis in monocytes but not in lymphocytes. FEBS Letters 302:206-208 (1992).
Brabin. Interactions of the female hormonal environment, susceptibility to viral infection and disease progression. A/OS Patient Care and STDs. 16:211-221 (2002).
Braegger et al., Tumor necrosis factor alpha in stool as a marker of intestinal inflammation. The Lancet 339:89-91 (1992).
Brant et al., American families with Crohn's disease have strong evidence for linkage to chromosomes 16 but not chromosome 12. Gastroentrol 115:1056-1061 (1998).
Bream et al., A single nucleotide polymorphism in the proximal IFN-gamma promoter alters control of gene transcription. Genes and Immunity 3:165-169 (2002).
Buning et al., Heterozygosity for IL23R, p.Arg318 Gin confers a protective effect not only against Crohn's disease but also ulcerative colitis. Aliment. Pharmacal Ther. 26:1025-1033 (2007).
Burks et al., GenBank Nucleic Acids Res (Suppl) 29:2065-2069 (1992).
Bush et al., Cancer chemoresistance: the relationship between p53 and multidrug transporters Int. J Cancer 98:323-330 (2002).
Calemine et al., Immunomodulation by diethylstillbestrol is dose and gender related: effects on thymocyte apoptosis and mitogen-induced proliferation. Toxicology 178:101-118 (2002).
Casini-Raggi et al., Mucosal imbalance of IL-1 and IL-1 receptor antagonist in inflammatory bowel disease. J Immunol 154:2434-2440 (1995).
Cavanaugh et al., Analysis of Australian Crohn's disease pedigrees refines the localization for susceptibility to inflammatory bowel disease on chromosome 16. Ann Hum Genet 62:291-298 (1998).
Cenci et al., Estrogen deficiency induces bone loss by increasing T cell proliferation and lifespan through IFN-gamma induced class II transactivator. PNAS USA 100:10405-10410 (2003).
Chaudhary et al., Prediction of response to infliximab in Crohn's disease. Digestive and Liver Disease 37:559-563 2005.
Chevillard et al. Two new polymorphisms in the human interferon gamma promoter. Eur J Immunogenetics 29:52-56 (2002).
Chiaretti et al., Gene expression profile of adult T-cell acute lymphocytic leukemia identifies distinct subsets of patients with different responses to therapy and survival. Blood 103:2771-2778 (2004).
Cho et al., Confirmation of a susceptibility locus for Crohn's disease on chromosome 16. Inflamm Bowel Dis. 3:186-190 (1997).
Cho et al., Identification of novel susceptibility loci for inflammatory bowel disease on chromosome 1p, 3q and 4q: evidence for epistasis between 1 p and IBD1. PNAS USA 95:7502-7507 (1998).
Cippitelli et al. Retinoic acid-induced transcriptional modulation of the human interferongamma promoter. J Biol Chemistry 271:26783-26793 (1996).
Cippitelli et al., Vitamin D3: a transcriptional modulator of the interferon-gamma gene. Eur J Immunol Abstract Only 28:3017-3030 (1998).
Costello et al., Dissection of the inflammatory bowel disease transcriptome using genome wide cDNA microarrays. PloS Medicine 2:0771-0787 (2005).
Curran et al., Genetic analysis of inflammatory bowel disease in a large European cohort supports linkage to chromosome 12 and 16. Gastroenterology 115:1066-1071 (1998).
Cushman et al., Effects of estrogen and selective estrogen receptor modulators in hemostasis and inflammation: potential differences among drugs. Annals of New York Academy of Sciences Abstract Only 949:175-180 (2001).
Cushman et al., Tamoxifen and cardiac risk factors in healthy women—suggestion of an anti-inflammatory effect, arteriosclerosis, thrombosis and vascular biology. Arterioscler Thromb Vasc Biol 21:251-266 (2001).
CUZZOCREA et al., 17 beta-estradiol anti-inflammatory activity in Carrageenan-induced pleurisy. Endocrinology 141:1455-1463 (2000).
Derrkx et al., Tumor-necrosis-factor antibody treatment in Crohn's disease. The Lancet 342:173-174 (1993).
Desilva et al., Pharmacogenetics of infliximab in Crohn's disease: the 5q31/IBD5 risk haplotype predict response. Gastroenterology 122:Abstract M1423 (2002).
Devlin et al., NOD2 variants and antibody response to microbial antigens in Crohn's disease patients and their unaffected relatives. Gastroenterology 132:576-586 (2007).
Devlin et al., NOD2 variants are significantly associated with sero-reactivity to microbial antigens in Crohn's disease. AGA Institute Digestive Disease Week, Abstract #442 Only (2006).
Diamond et al., Binding of the integrin Mac-1 (CD11 b/CD18) to the third immunoglobulin-like domain of ICAM01 (CD54) and its regulation by glycosylation. Cell 65:961-971 (1991).
Diamond et al., ICAM-1 (CD54): A counter receptor for Mac-1 (CD11b/CD18). J Cell Biol.111:3129-3139 (1990).
Dib et al., A comprehensive genetic map of the human based on 5,264 microsatellites. Nature 380:152-154 (1996).
Dubinsky et al., Familial expression of serological immune responses in pediatric IBD. J of Pediatric Gastroenterology and Nutrition Abstract #150 41:539 (2005).
Dubinsky et al., IL-23 receptor (IL-23R) gene protects against pediatric Crohn's disease. Inflamm Bowel Disease 13:511-515 (2007).
Dubinsky et al., Serum immune responses predict rapid disease progression among children with Crohn's disease: immune responses predict disease progression. Am J. Gastroenterology 101:360-367 (2006).
Duerr et al., A genome-wide association study identifies IL23R as an inflammatory bowel disease gene. Science 314:1461-1463 (2006).
Duerr et al., Association between ulcerative colitis and a polymorphism in intron 2 of the interleukin-2 receptor antagonist gene. Gastroenterology Abstract Only 108:a812 (1995).
Duerr et al., Homozygosity for an HLA class II group haplotype is associated with pANCA positive and familial ulcerative colitis. Abstract only Gastroenterology 108:a812 (1995).
Duerr et al., Linkage and association between inflammatory bowel disease and a locus on chromosome 12. Am J Hum Genet 63:95-100 (1998).
Erlandsson et al., Effects of raloxifene, a selective estrogen receptor modulator on thymus T cell reactivity and inflammation in mice. Cellular Immunology 205:103-109 (2000).
Erlich et al., Chapter 32: HLA DNA typing. PCR protocols. Edited by Innis et al. pp. 261-271.
Ewens et al., The transmission/disequilibrium test: history, subdivision, and admixture. Am J Hum Genetics 57:455-464 (1995).
Feder et al., A novel MHC class 1-like gene is mutated in patients with hereditary heaemochromatosis. Nature Genetics 13:399-408 (1996).
Ferrante et al., Predictors of early response to infliximab in patients with ulcerative colitis. Inflamm Bowel Disease 13:123-128 (2007).
Ferraris et al., Analysis of CARD15 gene variants in Italian pediatric patients with inflammatory bowel disease. J of Pediatrics 147:272-273 (2005).
Flores et al. In vitro evaluation of the effects of candidate immunosuppressive drugs: flow cytometry and quantitative real-time PCR as two independent and correlated read-outs. Journal of Immunological Methods 289:123-135 (2004).
Fox et al., Estrogen regulates the IFN-gamma promoter. J Immunol 146:4362-4367 (1991).
Franke et al. Replication of signals from recent studies of Crohn's disease identifies previously unknown disease loci for ulcerative colitis. Nature Genetics 40(6):713-715 (2008).

(56) References Cited

OTHER PUBLICATIONS

Fujikado et al., Identification of arthritis related gene clusters by microarray analysis analysis of two independent mouse models for rheumatoid arthritis. Arthritis Research and Therapy 8:1-13 (2006).
Fujino et al., Increased expression of interleukin 17 in inflammatory bowel disease gene. Gut 52:65-70 (2003).
Garcia-Bates et al., Peroxisome proliferator-activated receptor gamma ligands enhance human B cell antibody production and differentiation. J Immunology 183:6903-6912 (2009).
Gasche et al., A simple classification of Crohn's disease: report of the working party for the world congresses of gastroenterology, Vienna. Inflammatory Bowel Disease 6:8-15 (2000).
Gewirtz et al., Dominant-negative TLR5 polymorphism reduces adaptive immune response to flagellin and negatively associates with Crohn's disease. Am J Physiol Gastrointest Liver Physiol. 290:G1157-G1163 (2006).
Giacomelli et al., Combination therapy with cyclosporin and methotrexate in patients with early rheumatoid arthritis soon inhibits TNF production without decreasing TNF mRNA level: an in vivo and in vitro study. Clinical and Experimental Rheumatology 20:365-372 (2002).
Gilmore et al., Effect of estradiol on cytokine secretion by proteolipid protein-specific T cell clones isolated from multiple sclerosis patients and normal control subjects. Journal of Immunology. Abstract only.158:446-451 (1997).
Gonsky et al., CD2 mediates activation of the IFN-gamma intronic STAT binding region in mucosal T cells. Eur J Immunol 33:1152-1162 (2003).
Gonsky et al., Mucosa-specific targets for regulation of IFN-gamma expression: lamia propia cells use different cis-elements than peripheral blood T cells to regulate transactivation of IFN-gamma expression. J Immunol 164:1399-1407 2000.
Greenstein et al., Perforating and non-perforating indications for repeated operation in Crohn's disease: evidence of two clinical forms. Gut 29:588-592 (1988).
Haertel et al., Dose-dependent immunomodulatory effects of acetylsalicylic acid and indomethacin in human whole blood: potential role of cyclooxygenase-2 inhibition. Scandanavian Journal Immunology 60:412-420 (2004).
Hampe et al., A genomewide analysis provides evidence for novel linkage in inflammatory bowel disease in a large European cohort. Am J Hum Genet 64:808-816 (1999).
Hampe et al., A genome-wide association scan of nonsynonymous SNPs identifies a susceptibility variant for Crohn's disease in ATG16L1 Nature Genetics 39:207-211 (2007).
Hampe et al., Association between insertion mutation in NOD2 gene and Crohn's disease in German and British populations. Lancet 357:1925-1928 (2001).
Hampe et al., Association of NOD2 (CARD15) genotype with clinical course of Crohn's disease: a cohort study. Lancet 359:1661-1665 (2002).
Hanifi et al., Genetic structure of IDDM1: two separate regions in the major histocompatibility complex contribute to susceptibility or protection. Diabetes A Journal of the American Diabetes Association 47:1-7 (1999).
Harnish et al. Beneficial effects of estrogen treatment in the HLA-B27 transgenic rat model of inflammatory bowel disease. Am J Physiol Gastrointest Liver Physiology 286:G118-124 (2004).
Hartel et al., Delayed cytokine mRNA expression kinetics after T-lymphocyte costimulation: a quantitative measure of the efficacy of cyclosporin A-based immunosuppression. Clinical Chemistry 48:2225-2231 (2002).
Hazra et al., Common variant of FUT2 are associated with plasma vitamin B12levels. Nature Genetics 40:1160-1162 (2008).
Herbon et al. High-resolution SNP scan of chromosome 6p21 in pooled samples from patients with complex diseases. Genomics 81:510-518 (2003).
Hess et al., The hydroxylamine of sulfamethoxazole synergizes with FK506 and cyclosporin A inhibiting T-cell proliferation. Journal of Pharmacology and Experimental Techniques. 281:540-548 (1996).

Hlavaty et al., Polymorphisms in apoptosis genes predict response to infliximab therapy in luminal and fistulizing Crohn's disease. Aliment Pharmacol Ther 22:613-626 2005.
Hogg et al., Adhesion molecules in cell interactions. Curr Opin Immunol. 5:383-390 (1993).
Hugot et al., Association of Nod2 leucine-rich repeat variants with susceptibility to Crohn's disease. Nature 411:599-603 (2001).
Hugot et al., Linkage analyses of chromosome 6 loci, including HLA, in familial C255 aggregations of Crohn's disease GET AID. Am J Med Genet 52:207-213 (1994).
Hugot et al., Mapping of a susceptibility locus for Crohn's disease on chromosome 16. Nature 379:821-823 (1996).
Inohara et al., Human NOD1 confers responsiveness to bacterial lipopolysaccharides. J Biol Chem 276:2551-2554 (2001).
Ioannidis et al., Replication validity of genetic association studies Nature Genetics 29:306-309 (2001).
Ippoliti et al., Combination of innate and adaptive immune alterations increased the likelihood of fibrostenosis in Crohn's disease. Inflamm Bowel Disease 16:1279-1285 (2010).
Ippoliti et al., The relationship between abnormal innate and adaptive immune function and fibrostenosis in Crohn's disease patients. Abstract only. (2006) Journal unknown.
Iris et al., Dense Alu clustering and a potential new member of the NFkB family within a 90 kilo base HLA Class III segment. Nature Genetics 3:137-145 (1993).
Jacob et al., Definition of microsatellite size variants for Tnfa and Hsp70 in autoimmune and nonautoimmune mouse strains. Immunogenetics 36:182-188 (1992).
Jarjour et al., The 8.5 kb PstI allele of the stress protein gene Hsp70-2: An independent risk factor for systemic lupus erythematosus in African Americans. Hum Immunol 45:59-63 (1996).
Johnston et al. Present status and future prospects for HIV therapies. Science 260:1286-1293 (1993).
Jongeneel et al., Extensive genetic polymorphism in the human tumor necrosis factor region and relation to extended HLA haplotypes. PNAS USA 88:9717-9721 (1991).
Juhasz et al., Quantification of chemotherapeutic target gene mRNA expression in human breast cancer biopsies: comparison of real-time reverse transcription-PeR vs. relative quantification reverse transcription-PeR utilizing DNA sequence analysis of PCR product. Journal of Clinical Laboratory Analysis 17:184-194 (2003).
Karpuzoglu-Sahin et al., Effects of long-term estrogen treatment on IFN-gamma, IL-2 and IL 4 gene expression and protein synthesis in spleen and thymus of normal C57BL/6 mice. Cytokine 14:208-217 (2001).
Kim et al. DQCAR113and DQCAR115 in combination with HLA-DRB1 alleles are significant markers of susceptibility to rheumatoid arthritis in the Korean population. Tissue Antigens 54:552-559 (1999).
Kirchhausen et al., Location of the domains of ICAM-1 by immunolabeling and single-molecule electron microscopy. J. Leukocyte Biology 53:342-346 (1993).
Kita et al., Sequence and expression of rat ICAM-1. Biochim Biophys Acta 1131:108-111 (1992).
Klein et al., Ex-vivo assessment of candidate anti-inflammatory agents in the treatment of Gram-negative sepsis. Immunology and Infectious Disease 4:33-35 (1994).
Koutroubakis et al., Tumor necrosis factor-alpha polymorphism in inflammatory bowel disease. Hellenic J of Gastroenterology 8:132-135 (1995).
Kugathansan et al., L 1007FsinsC variant of CARD15/NOD2 is strongly associated with early onset and fibrostenosing behavior in pediatric Crohn's disease. Gasteroenterology 126(4 Supp 2):A68 524.
Kugathansan et al., Loci on 20q13 and 21q22 are associated with pediatric onset inflammatory bowel disease. Nature Genetics 40:1211-1215 (2008).
Kutyavin, et al. 3'-Minor groove binder-DNA probes increase sequence specificity at PCR extension temperatures. Nucleic Acids Research, 28(2):655-661 (2000).
Kutyavin et al., Oligonucleotides with conjugated dihyropyrroloindole tripeptides: base composition and backbone effects on hybridization. Nucleic Acid Res 25:3718-3723 (1997).

(56) References Cited

OTHER PUBLICATIONS

Lakatos et al., NOD2/CARD15 mutations and genotype-phenotype correlations in patients with Crohn's disease. Hungarian multicenter study. Orvosi Hetilap 145:1403-1411 (2004).
Lasky. Selectins: interpreters of cell-specific carbohydrate information during inflammation. Science 258:964-969 (1992).
Latham et al., Estradiol treatment redirects the isotype of the autoantibody response and prevents the development of autoimmune arthritis. J of Immunol 171:5820-5827 (2003).
Laurence et al. Effect of tamoxifen on regulation of viral replication and human immunodeficiency virus (HIV) long terminal repeat-directed transcription in cells chronically infected with HIV-1. Blood 75:696-703 (1990).
Lee et al., Estrogen-mediated protection against HIV Tat protein-induced inflammatory pathways in human vascular endothelial cells. Cardiovascular Research 63:139-148 (2004).
Lemna et al., Mutation analysis for heterozygote detection and the prenatal diagnosis of cystic fibrosis. N. Eng. J. Med. 322:291-296 (1990).
Lesage et al., CARD15/NOD2 mutational analysis and genotype-phenotype correlation in 612 patients with inflammatory bowel disease. Am J of Human Genetics 70:845-857 (2002).
Leung et al. Expression profiling identifies chemokine (C-C Motif) ligand 18 as an independent prognostic indicator of gastric cancer. Gasteroenterology 127:457-469 (2004).
Li et al., Cloning, characterization and the complete 56.8-kilobase DNA sequence of the human NOTCH4 gene. Genomics 51:45-58 (1998).
Li et al., New serological biomarkers of inflammatory bowel disease. World J of Gasteroenterology14:5115-5124 (2008).
Limbergen et al., IL23R Arg381 Gin is associated with childhood onset inflammatory bowel disease in Scotland. Gut 56:1173-1174 (2007).
Lindner et al. Tamoxifen enhances interferon regulated gene expression in breast cancer cells. Molecular and Cellular Biochemistry 167:169-177 (1997).
Liu et al., Mucosal gene expression profiles following the colonization of immunocompetent defined-flora C3H mice with Helicobacter bilis: a prelude to typhlocolitis. Microbes and Infection 11:374-383 (2009).
Livak. Allelic discrimination using fluorogenic probes and the 5' nuclease assay. Genetic Analysis 14:143-149 (1999).
Lodes et al., Bacterial flagellin is a dominant antigen in Crohn disease. Journal of Clinical Investigation 113:1296-1306 (2004).
Louis et al. Association between polymorphism in IgG Fc receptor lila coding gene and biological response to infliximab in Crohn's disease. Aliment Pharmacol Ther 19:511-519 (2004).
Macdonald et al., Tumor necrosis factor-alpha and interferon-gamma production measured at the single cell level in normal and inflamed human intestine Clin Exp Immunol 81:301-305 (1990).
Mansfield et al., Novel genetic association between ulcerative colitis and the antiinflammatory cytokine interleukin-1 receptor antagonist. Gastroenterology 106:637-642 (1994).
Martin et al., Recombination rates across the HLA complex: use of microsatellites as a rapid screen for recombinant chromosome. Human Molecular Genetics 4:423-428 (1995).
Martins et al., Transcriptional repressor Blimp-1 regulates T cell homeostasis and function. Nature Immunology 7:457-265 (2006).
Matalka. The effect of estradiol but not progesterone on the production of cytokines in stimulated whole blood is concentration-dependent. Neuro Endocrinology Letters. Abstract only. 24:185-191 (2003).
Matejuk et al., 17-beta-estradiol inhibits cytokine, chemokine and chemokine receptor mRNA expression in the central nervous system of female mice with experimental autoimmune encephalomyelitis. J of Neuroscience Research 65:529-542 (2001).
Matsunaga et al., Application of differential display to identify genes for lung cancer detection in peripheral blood. Int J of Cancer 100:592-599 (2002).

McCall et al., Constitutive expression of TNF-a and of an IL-8 gene is associated with genetic susceptibility to chronic granulomatous enterocolitis in inbred rats. AGA Abstracts p. A740 (1993).
McEver. Leukocyte—endothelial cell interactions. Curr Opin Cell Bioi 4:840-849 (1992).
McGovern et al., Genetic epistasis of IL23/IL 17 pathway genes in Crohn's disease. Inflamm Bowel Dis. 15:883-889 (2009).
Mehmut et al., Fas ligand and TNF-related apoptosis-inducing ligand induction on infiltrating lymphocytes in bladder carcinoma by Bacillus Calmette-Guerin treatment Urologica International 75:80-87 (2005).
Mei et al., Familial expression of anti-*Escherichia coli* outer membrane porin C in relatives of patients with Crohn's disease. Gasteroenterology 130:1078-1085 (2006).
Melmed et al., Patients with inflammatory bowel disease are at risk for vaccine-preventable illness. Am J Gasteroenterol 101:1834-1840 (2006).
Mesange et al., Ligands of the antiestrogen-binding site are able to inhibit virion production of human immunodeficiency virus 1-infected lymphocytes. Molecular Pharmacology 50:75-79 (1996) Abstract only.
Messer et al., Polymorphic structure of the tumor necrosis factor (TNF) locus: an Ncol polymorphism in the first intron of TNF-8 gene correlates with a variant in amino acid position 26 and a reduced level ofTNF-8 production. J Exp Med 173:209-219 (1991).
Michelsen et al., IBD-Associated TL 1A Gene (TNFSF15) Haplotypes Determine Increased Expression of TL 1A Protein. PLoS ONE. 4:e4719 (2009).
Milner et al. Polymorphic analysis of the three MHC-linked HSP70 genes. Immunogenetics 36:357-362 (1992).
Mingjia et al., How oestrogen or progesterone might change a woman's susceptibility to HIV 1 infections. The Australian and New Zealand Journal of Obstetrics and Gynecology Abstract only. 42:472-475 (2002).
Misiewicz et al., The estrogen antagonist tamoxifen inhibits carrageenan induced inflammation in LEWIN female rats. Life Sciences 58:PL281-286 (1996).
Moghaddam et al., Genetic structure of IDDM1: two separate regions in the major histocompatibility complex contribute to susceptibility or protection. Diabetes 47:263-269 (1998).
Mow et al., Association of antibody responses to microbial antigens and complications of small bowel Crohn's disease. Gastroenterology 126:414-424 (2004).
Murch et al., Location of tumor necrosis factor alpha by immunochemistry in chronic inflammatory bowel disease. Gut 34:1705-1709 (1993).
Murillo et al., CARD15 gene and the classification of Crohn's disease. Immunogenetics 54:59-61 (2002).
Murray et al., GenBank Accession No. G08322 (Feb. 5, 1997).
Nadal et al., Imbalance in the composition of the duodenal microbiata of children with coeliac disease. J Medical Microbiol. 56:1669-1674 (2007).
Nakamura et al., In situ expression of the cell adhesion molecules in Inflammatory Bowel Disease; evidence of immunologic activation of vascular endothelial cells. Lab Investig 69(1):77-85 (1993).
Nakaya et al., Estrogenic compounds suppressed interferon-gamma production in mouse splenocytes through direct cell-cell interaction. In Vitro Cell Dev Biol Anim 39:383-387 (2003).
Nedospasov et al., DNA sequence polymorphism at the human tumor necrosis factor (TNF) locus. Numerous TNF/lymphotoxin alleles tagged by two closely linked microsatellitesin the upstream region of the lymphotoxin (TNF-beta) gene. J. Immunol. 147:1053-1059 (1991).
Nedospasov et al., Genetic polymorphism of the human gene locus containing genes for tumor necrosis factors: ethnic differences in allele frequency distribution. Chemical Abstracts, 120(5):47183y (1994).
Ogura et al., NOD2, a Nod1/Apaf-1 family member that is restricted to monocytes and activates NF-kB. J Biol Chem 276:4812-4818 (2001).
Ohmen et al., Susceptibility locus for inflammatory bowel disease on chromosome 16 has a role in Crohn's disease, but not in ulcerative colitis. Hum Mol Genet 5:1679-1683 (1996).

(56) References Cited

OTHER PUBLICATIONS

Okazaki et al., Contributions of the IBD5, IL23R, ATG16L 1, and NOD2 to Crohn's disease risk in a population-based case-controlled study: evidence of gene-gene interaction. Inflamm Bowel Disease 14:1528-1541 (2008).
Orholm et al., Familial occurrence of inflammatory bowel disease. New England Journal of Medicine 324:84-88 (1991).
Over et al., Thromphilia and inflammatory bowel disease: does factor V mutation have a role? European Journal of Gastroenterology and Hepatology 10:827-829 (1998).
Owerbach et al. The HOXD8 locus (2q31) is linked to type I diabetes-interaction with chromosome 6 and 11 disease susceptibility genes. Diabetes 44:132-136 (1995).
Papadakis et al., Anti-Flagellin (Cbir1) phenotypic and genetic Crohn's Disease associations, Inflamm Bowel Dis 13(5):524-530 (2007).
Papp et al., Seroreactivity to microbial components in Crohn's disease is associated with Ileal involvement, noninflammatory disease behavior and NOD2/CARD15 genotype but not with risk for surgery in a Hungarian cohort of IBO patients. Inflamm Bowel Disease 13:984-992 (2007).
Parkes et al., Susceptibility loci in inflammatory bowel disease. Lancet 348:1588 (1996).
Parrello et al., Upregulation of the IL-12 receptor beta 2 chain in Crohn's disease. J Immunol 165:7234-7239 (2000).
Partanen et al., Low degree of DNA polymorphism in the HLA-linked lymphotoxin (tumor necrosis factor-B) gene. Scand J. Immunol. 28:313-316 (1988).
Paul. Chapter 19. Fundamental Immunology 4th edition pp. 663-665 (1998).
PCT/US1995/001434 International Preliminary Examination Report dated May 22, 1996.
PCT/US1995/001434 International Search Report dated Jul. 21, 1995.
PCT/US1995/001434 Written Opinion dated Nov. 17, 1995.
PCT/US1995/006107 International Preliminary Examination Report dated Jun. 5, 1996.
PCT/US1995/006107 International Search Report dated Oct. 6, 1995.
PCT/US1995/006107 Written Opinion dated Feb. 12, 1996.
PCT/US1997/000042 International Preliminary Examination Report dated Apr. 1, 1998.
PCT/US1997/000042 International Search Report dated Apr. 21, 1997, dated May 14, 1997.
PCT/US1997/000042 Written Opinion dated Oct. 29, 1997.
PCT/US2000/025112 International Preliminary Examination Report dated Dec. 20, 2001.
PCT/US2000/025112 International Search Report dated Aug. 6, 2001.
PCT/US2003/023926 International Preliminary Examination Report dated Aug. 19, 2004.
PCT/US2003/023926 International Search Report dated Jun. 23, 2004.
PCT/US2005/018161 International Search Report dated Jun. 4, 2008.
PCT/US2005/018161 Written Opinion dated Jun. 4, 2008.
PCT/US2005/044335 International Preliminary Examination Report dated Jun. 13, 2007.
PCT/US2005/044335 International Search Report dated Sep. 22, 2006.
PCT/US2005/044335 Written Opinion mailed Sep. 22, 2006; dated Aug. 26, 2006.
PCT/US2007/008597 International Preliminary Examination Report dated Oct. 8, 2008.
PCT/US2007/008597 International Search Report dated Jun. 4, 2008.
PCT/US2007/008597 Written Opinion dated Jun. 4, 2008.
PCT/US2008/054033 International Preliminary Examination Report dated Aug. 19, 2009.
PCT/US2008/054033 International Search Report dated Aug. 21, 2008.
PCT/US2008/054033 Written Opinion Aug. 21, 2008.
PCT/US2008/055020 International Preliminary Examination Report dated Aug. 26, 2009.
PCT/US2008/056103 International Preliminary Report on Patentability dated Nov. 24, 2009.
PCT/US2008/056103 International Search Report dated Sep. 3, 2008.
PCT/US2008/056103 Written Opinion dated Sep. 3, 2008.
PCT/US2008/057028 International Preliminary Report on Patentability dated Sep. 15, 2009.
PCT/US2008/057028 International Search Report dated Oct. 10, 2008.
PCT/US2008/057028 Written Opinion dated Oct. 10, 2008.
PCT/US2008/057820 International Preliminary Report on Patentability dated Sep. 22, 2009.
PCT/US2008/057820 International Search Report dated Sep. 11, 2008.
PCT/US2008/061652 International Preliminary Report on Patentability dated Oct. 27, 2009.
PCT/US2008/061652 International Search Report dated Dec. 1, 2008.
PCT/US2008/061652 Written Opinion dated Dec. 1, 2008.
PCT/US2008/063202 International Preliminary Examination Report dated Nov. 10, 2009.
PCT/US2008/063202 International Search Report dated Nov. 18, 2008.
PCT/US2008/063202 Written Opinion dated Nov. 18, 2008.
PCT/US2008/080526 International Search Report dated Mar. 25, 2009.
PCT/US2008/080526 Written Opinion dated Mar. 25, 2009.
PCT/US2009/044720 International Search Report dated Nov. 5, 2009.
PCT/US2009/044720 Written Opinion dated Nov. 5, 2009.
PCT/US2009/061698 International Search Report dated Mar. 16, 2010.
PCT/US2009/069531 International Search Report dated Aug. 4, 2010.
PCT/US2009/069531 Written Opinion dated Aug. 4, 2010.
PCT/US2009/069534 International Search Report dated Mar. 1, 2010.
PCT/US2009/069541 Written Opinion dated Mar. 4, 2010.
PCT/US2010/043427 International Search Report dated Dec. 3, 2010.
PCT/US2011/021180 International Search Report dated Jun. 15, 2011.
PCT/US2011/021382 International Search Report dated Mar. 15, 2011.
PCT/US2011/021382 Written Opinion dated Mar. 15, 2011.
PCT/US2011/028694 Written Opinion dated Jul. 27, 2011.
Plevy et al., Increased mucosal tnf-alpha mrna levels and numbers of tnf-alpha producing cells are unique to mucosal inflammation in crohn's disease, Faseb Journal, Abstract 58498:A1010 (Apr. 1994).
Plevy et al., The tumor necrosis factor (TNF) microsatellite haplotype A2B1C204E1 correlates with increased TNF production in Crohn's disease. Abstract only AASLD at Digestive disease week (1995).
Plevy et al. TNF-alpha MRNA levels differentiated mucosal inflammation in crohn's disease from ulcerative colitis. J. Immunology 150:10a (1993).
Plevy et al., Tumor necrosis factor microsatellites define Crohn's disease-associated haplotype on chromosome 6. Gasteroenterology 110:1053-1060 (1996).
Plevy et al, Tumor necrosis factor (TFN) microsatellite associations with HLA-DR2+ patients define Crohn's disease (cd) and ulcerative colitis (uc)-specific genotypes. Gastroenterology 106:A754 (1994).
Pociot et al., A tumor necrosis factor beta gene polymorphism in relation to monokine secretion and insulin dependent diabetes mellitus. Scand J. Immunol., 33:37-49 (1991).
Pociot et al., Association of tumor necrosis factor and class II major histocompatibility complex alles with secretion of tnf alfa and tnf

(56) References Cited

OTHER PUBLICATIONS beta by human mononuclear cells: a possible link to insulin-dependent diabetes mellitus. Abstract only. Eur. J. Immunology 23:224-231 (1993).
Poicot et al., Polymorphic analysis of the human MHC-linked heat shock protein 70 (HSP70- and HSP70-Hom genes in insulin-dependent diabetes mellitus (IOOM). Scand J Immunol 38:491-495 (1993).
Polanczyk et al., The protective effect of 17beta-estradiol on experimental autoimmune encephalomyelitis is mediated through estrogen receptor-a. American J of Pathology 163:1599-1605 (2003).
Potts et al., Using microbicides to fight the spread of HIV. Science 300:431 (2003).
Prehn et al., The T Cell Costimulator TL 1A Is Induced by Fe R Signaling in Human Monocytes and Dendritic Cells. J Immunol 178:4033-4038 (2007).
Radlmayr et al., The c-insertion mutation of the NOD2 gene is associated with fistulizing and fibrostenotic phenotypes in Crohn's diseases. Gasterenterology 122:2091-2095 (2002).
Rector et al., Mannan-binding lectin (MBL) gene polymorphisms in ulcerative colitis and Crohn's disease. Genes and Immunity 2:323-328 (2001).
Redon et al. Global variation in copy number in the human genome. Nature. 444(7118): 444-54 (2006).
Reinecker et al., Enhanced secretion of tumor necrosis factor-alpha, IL-6 and IL-1 beta by isolated lamina propia mononuclear cells from patients with ulcerative colitis and Crohn's disease Clin Exp Immunol 94:174-181 (1993).
Rioux et al., Genome-wide association study identifies new susceptibility loci for Crohn disease and implicates autophagy in disease pathogenesis. Nature Genetics 39(5):596-604 (2007).
Rodriguez-Caballero et al., A new simple whole blood flow cytometry-based method for simultaneous identification of activated cells and quantitative evaluation of cytokines released during activation Laboratory Investigation 84:1387-1398 (2004).
Roth et al., Familial empiric risk estimates of inflammatory bowel disease in Ashkenazi Jews. Gastroenterology 96:1016-1020 (1989).
Roth et al., Geographic origins of Jewish patients with inflammatory bowel disease. Gastroenterology 97:900-904 (1989).
Rozen et al., Crohn's disease in the Jewish population of Tei-Aviv-Yafo: epidemiologic and clinical aspects. Gastroenterology 76:25-30 (1979).
Salem. Estrogen, a double-edged sword: modulation of TH1- and THw- medicated inflammations by differential regulation of T J1/TH2 cytokine production. Inflammation and Allergy 3:97-104 (2004).
Salem et al., Mediation of the immunomodulatory effect of beta-estradiol on inflammatory response by inhibition of recruitment and activation of inflammatory cells and their gene expression of TNF-alpha and IFN-gamma. Inti Archives of Allergy and Immunology Abstract Only. 121:235-245 (2000).
Saruta et al., TLR8-mediated activation of human monocytes inhibits TL 1A expression. Eur J Immunol 39:2195-2202 (2009).
Sategna-Guidetti et al., Tumor necrosis factor cachectin in Crohn's disease—relation of C385 serum concentration to disease activity. Recenti Progressi 84:93-99 (1993).
Satsangi et al., The genetics of inflammatory bowel disease. Gut 40:572-574 (1997).
Saxon et al., A distinct subset of antineutrophil cytoplasmic antibodies is associated with inflammatory bowel disease. J Allergy Clin. Immunol. 86:202-210 (1990).
Schimanski et al., Effect of chemokine receptors CXCR4 and CCR7 on the metastatic behavior of human colorectal cancer Clinical Cancer Research 11:1743-1750 (2005).
See et al., Increased tumor necrosis factor alpha (TNF-alpha) and natural killer cell (NK) function using an integrative approach in late stage cancers. Immunological Investigations 31:137-153 (2002).
Shanahan et al., Inflammatory Bowel Disease. Textbook of Internal Medicine. W.N. Kelle et al. (editor) 2nd edition J. B. Lippincott Company, Philadelphia 81:489-502 (1992).

Shovam et al., Evaluation of the BioPiex 2200 ANA screen: Analysis of 510 healthy subjects: incidence of natural/predictive autoantibodies. Annals of the New York Academy of Science, 1050:380-388 (2005).
Silman et al., Epidemiology and genetics of rheumatoid arthritis. Arthritis Research 4 Supp 3:S265-S272 (2002).
Silverberg et al., Evidence for linkage between Crohn's disease (CD) and a locus near the major histocompatibility complex (MHC) on chromosome 6 in a Canadian inflammatory bowel disease (IBO) population. Gastroenterology 116:G3560 AGA Abstracts (1999).
Silverberg et al., The HLA DRBL 0103 allele is associated with Crohn's disease (CD) in a Toronto inflammatory bowel disease (IBO) population. Gastroenterology 116:G3559 AGA Abstracts (1999).
Singal et al., D6S273 microsatellite polymorphism and susceptibility to Rhematoid Arthritis. Tissue Antigens 52:353-358 (1998).
Singal et al., Genetics of rheumatoid arthritis (RA): two separate regions in the major histocompatibility complex contribute to susceptibility to RA. Immunol Lett 69:301-306, (1999).
Sitaraman et al., Elevated flagellin-specific immunoglobulins in Crohn's disease. Am J Physiol Gastrointest Liver Physiol 288:G403-G406 (2005).
Smith. Adherence of neutrophils to canine cardiac myocyyes in vitro is dependent on intercellular adhesion molecule-1. J Clin Invest 88:1216-1223 (1991).
Smith et al., Cooperative interactions of LFA-1 and Mac-1 with intercellular adhesion molecule-1 in facilitating adherence and transendothelial migration of human neurophils in vitro. J Clin Invest 83:2008-2017 (1989).
Smith et al., Estrogen protects against vaginal transmission of simian immunodeficiency virus. J Infectious Diseases 182:708-715 (2000).
Smith et al., Recognition of an endothelial determinant for CD18-dependent human neutrophil adherence and transendothelial migration. J Clin Invest 82:1746-1756 (1988).
Smith et al. Topical estrogen protects against SIV vaginal transmission without evidence of systemic effect. AIDS 18:1637-1643 (2004).
Smith. Transendothelial Migration, in Breakthroughs in Molecular Biology, vol. 4: Adhesion: Its Role in Inflammatory Disease. Harlan, J. and Liu D., eds., W. H. Freeman & Co. New York. pp. 83-115 (1992).
Springer et al., Adhesion receptors of the immune system. Nature 346:425-433 (1990).
Staunton et al., Primary Structure of ICAM-1 demonstrates interaction between member of the immunoglobulin and integrin supergene families. Cell 52:925-933 (1988).
Staunton et al. The arrangement of the immunoglobulin-like domains of ICAM-1 and binding sites for LFA-1 and rhinovirus. Cell 61:243-254 (1990).
Steer et al., Development of rheumatoid arthritis is not associated with two polymorphisms in the Crohn's disease gene CARD15 Rheumatology 42:304-307 (2003).
Stites et al., Chapter 22 of the 4th edition of Basic and Clinical Immunology, Lange Medical Publications, Los Altos, California, p. 325-365 (1982).
Strater et al., Expression of TRAIL and TRAIL receptors in colon carcinoma: TRAIL-R1 is an independent prognostic parameter. Clinical Cancer Research 8:3734-3740 (2002).
Stulik et al., The different expression of proteins recognized by monoclonal anti-heat shock protein 70 (hsp70) antibody in human colonic diseases. Electrophoresis 18:625-628 (1997).
Sugaya et al., Gene organization of human NOTCH4 and (CTG)n polymorphism in this human counterpart gene of mouse proto-oncogene Int3. Gene 189:235-244 (1997).
Sugaya et al., Three genes in the human MHC class III region near the junction with the class II: gene for receptor of advanced glycosylation end products, PBX2 homeobox gene and a notch homolog, human counterpart of mouse mammary tumor gene int-3. Genomics 23:408-419 (1994).
Sullivan et al., Prevalence of a mutation causing C2 deficiency in systemic lupus erythematosus. J of Rheumatology 21:1128-1133 (1994).

(56) References Cited

OTHER PUBLICATIONS

Takedatsu et al., Linkage of CD-related serological phenotypes: NFKB1 haplotypes are associated with anti-CBir1 & ASCA, and show reduced NF-KB activation. Gut. 58:60-67 (2009).
Targan et al., Antibodies to a novel flagellin (CBir1) define a unique serologic response in Crohn's disease (CD). Gastroenterology Abstract only 126(4), Suppl 2:A113 (2004).
Targan et al., Antibodies to CBir1 flagellin define a unique response that is associated independently with complicated Crohn's disease. Gastroenterology 128:2020-20289 (2005).
Targan et al., Definition of a lamina propia T cells responsive state enhanced cytokine responsiveness of T cells stimulated through the CD2 pathway. J Immunol 154:664-675 (1995).
Tarlow et al., Polymorphism in human IL-1 receptor antagonist gene intron 2 is caused by variable numbers of an 86-bp tandem repeat. Hum Genet 91:403-404 (1993).
Taylor et al., Analysis of IBD5-related polymorphisms: IRF1 but not SLC22A4 or SLC22A5 is associated with 18D in Puerto Rican populations. Digestive Disease Week Abstract only (2006). Journal unknown, AGA Institute, Am. Gastroent. Assoc. Inst., Annual Meeting, CA, May 20-25, 2006, Abst #444.
Taylor et al., Genes regulating the expression of antibody to C8ir1 flagellin in humans are located within a syntenic region to the major mouse colitogenic locus Cdcs1. AGA Institute Abstract #444 p. A-64 (2006).
Taylor et al., IL23R haplotypes provide a large population attributable risk for Crohn's disease. Inflammatory Bowel 14:1185-1191 (2008).
Taylor et al., Linkage disequilibrium mapping identifies a Class III major histocompatibility complex (MHC) susceptibility haplotypes to Crohn's disease in Ashkenazi Jews. American Journal of Human Genetics. 65(4): A102, abstract 534 (1999).
Thomas et al., Estrogen and raloxifen activities on amyloid-beta-induced inflammatory reaction. Microvascular Research 61:28-39 (2001).
Tomassini. et al., cDNA cloning reveals that the major group rhinovirus receptor on Hela cells in intercellular adhesion molecule-1. PNAS USA 86:4907-4911 (1989).
Torok et al., Crohn's disease is associated with a Toll-like receptor-9 polymorphism. Gastroenterology 127:365-368 (2004).
Torres et al., Newborn screening for Hermansky-pudlak syndrome Type 3 in Puerto Rico. Blood 108:3290 (2006).
Tountas et al., Genetic association between allele 2 of IL-1 receptor antagonist (IL-1 ra) and ulcerative colitis in Los Angeles based hispanic population. Abstract XP000673112 only. Gastroenterology 108:806-813 (1995).
Tountas et al. Heterogenous association between allele 2 of IL-2 receptor antagonist (ILC4371 RA) and ulcerative colitis in Jewish and non-Jewish populations. Abstract XP000673114 only. J. Investigative Medicine 44(1) (1996).
Tountas et al., Increased carriage of allele 2 of IL-1 receptor antagonist (IL-1ra) in Jewish population: the strongest known genetic association in ulcerative colitis. American Gastroenterology Association Abstract Only (1996).
Trachtenberg et al., Rare HLA DR-DQ haplotypes associated with inflammatory bowel disease. Human Immunol 55 (supp. 1):59 Abstract #42 (1997).
Trowsdale et al., Map of the human MHC. Immunol. Today 12:443-446 (1991).
Turchan et al., Estrogen protects against the synergistic toxicity by HIV proteins, methamphetamine and cocaine. BMC Neuroscience 2:3 (2001).
Udalova et al., Highly informative typing of the human TNF locus using six adjacent polymorphic markers Genomics 16:180-186 (1993).
U.S. Appl. No. 08/196,003 Office Action dated Dec. 12, 1995.
U.S. Appl. No. 08/196,003 Office Action dated Oct. 2, 1996.
U.S. Appl. No. 08/245,297 Office Action dated Dec. 9, 1996.
U.S. Appl. No. 08/245,297 Office Action dated Jan. 22, 1996.
U.S. Appl. No. 08/245,297 Office Action dated Jul. 11, 1996.
U.S. Appl. No. 08/245,297 Office Action dated Mar. 15, 1995.
U.S. Appl. No. 08/587,911 Office Action dated Apr. 15, 1997.
U.S. Appl. No. 08/587,911 Office Action dated Jan. 5, 1998.
U.S. Appl. No. 08/587,911 Office Action dated Jul. 6, 1998.
U.S. Appl. No. 08/798,668 Notice of Allowance dated Apr. 29, 1999.
U.S. Appl. No. 08/798,668 Office Action dated Apr. 29, 1999.
U.S. Appl. No. 08/798,668 Office Action dated Aug. 10, 1997.
U.S. Appl. No. 08/798,668 Office Action dated Jan. 29, 1998.
U.S. Appl. No. 08/798,668 Office Action dated Jun. 6, 1997.
U.S. Appl. No. 08/933,824 Office Action dated Apr. 14, 1998.
U.S. Appl. No. 08/933,824 Office Action dated Jan. 5, 1999.
U.S. Appl. No. 09/395,345 Office Action dated May 3, 2000.
U.S. Appl. No. 09/395,345 Office Action dated Nov. 21, 2000.
U.S. Appl. No. 09/419,406 Notice of Allowance dated Mar. 19, 2002.
U.S. Appl. No. 09/419,406 Office Action dated Apr. 24, 2000.
U.S. Appl. No. 09/419,406 Office Action dated Dec. 28, 2000.
U.S. Appl. No. 09/419,406 Office Action dated Jul. 17, 2001.
U.S. Appl. No. 09/419,408 Office Action dated Feb. 1, 2000.
U.S. Appl. No. 10/075,425 Office Action dated Jun. 17, 2005.
U.S. Appl. No. 10/075,425 Office Action dated Oct. 1, 2004.
U.S. Appl. No. 10/356,736 Office Action dated Apr. 10, 2006.
U.S. Appl. No. 10/356,736 Office Action dated Apr. 26, 2007.
U.S. Appl. No. 10/356,736 Office Action dated Aug. 14, 2008.
U.S. Appl. No. 10/356,736 Office Action dated Jul. 7, 2005.
U.S. Appl. No. 10/356,736 Office Action dated Nov. 30, 2007.
U.S. Appl. No. 10/526,256 Office Action dated Aug. 25, 2009.
U.S. Appl. No. 10/526,256 Office Action dated Dec. 29, 2008.
U.S. Appl. No. 10/526,256 Office Action dated May 9, 2008.
U.S. Appl. No. 11/720,785 Office Action dated Dec. 23, 2010.
U.S. Appl. No. 11/720,785 Office Action dated Jul. 19, 2010.
U.S. Appl. No. 12/528,055 Office Action dated Jun. 27, 2011.
U.S. Appl. No. 12/530,390 Office Action dated Mar. 25, 2011.
U.S. Appl. No. 12/599,549 Office Action dated Apr. 26, 2011.
Vaidya et al., The cytotoxic T lymphocyte antigen-4 is a major Graves' disease locus. Human Molecular Genetics 8:1195-1199 (1999).
Vasiliauskas et al., Marker antibody expression stratifies Crohn's disease into immunilogically homogenous subgroups with distinct clinical characteristics. Gut 47:487-496 (2000).
Vasiliauskas et al., Perinuclear antineutrophil cytoplasmic antibodies in patients with Crohn's disease define a clinical subgroups. Gastroenterology 110:1810-1819 (1996).
Vavassori et al., CARD15 mutation analysis in an Italian population: Leu1007fsinsC but neither Arg702Trp nor Gly908Arg mutations are associated with Crohn's disease. Inflamm Bowel Dis 10:116-121 (2004).
Verdu et al., Modulatory effects of estrogen in two murine models of experimental colitis. American J Physiology 283:G27-G36 (2002).
Vermiere et al., CARD15 genetic variation in a Quebec population: prevalence, genotype-phenotype relationship and haplotype structure. Am J Hum Genet 71:74-83 (2002).
Verthelyi et al. Sex hormone levels correlate with the activity of cytokine-secreting cells in vivo. Immunology 100:384-390 (2000).
Voraberger et al., Cloning on the human gene for intercellular adhesion molecule-1 and analysis of its 5'-regulatory region. J Immunol 147:2777-2786 (1991).
Warzocha et al., Tumor necrosis factor ligand receptor system can predict treatment outcome of lymphoma patients. Journal of Clinical Oncology 15:499-508 (1997).
Webb et al., Genetic variability at the human tumor necrosis factor loci. J. Immunol 145:1278-1285 (1993).
Weber et al. Abundant class of human DNA polymorphisms which can be typed using the polymerase chain reaction. Am J Hum Genet 44:388-396 (1989).
Williams et al., Optimization strategies for the polymerase chain reaction. Biotechniques 7:762-768 (1989).
Wouters et al., Inter- and intra-individual variation of endotoxin- and beta (1-3)-glucan-induced cytokine responses in a whole blood assay. Toxicology and Industrial Health 18:15-27 (2002).

(56) References Cited

OTHER PUBLICATIONS

Wu et al. Tamoxifen alleviates disease severity and decreases double negative T cells in autoimmune MRL-lpr/lpr mice. Immunology 100:110-118 (2000).
Wu et al., Tamoxifen decreases renal inflammation and alleviates disease severity in autoimmune NZBIW F1 mice. Scandinavian Journal of Immunology 52:393-400 (2000).
Xiao et al., Interaction of Cocksackievirus A21 with its cellular receptor ICAM-1. J Viral 75:2444-2451 (2001).
Yamamoto-Furusho et al., Complotype SC30 is associated with susceptibility to develop severe C462 ulcerative colitis in Mexicans. J Clin Gasterol 27:178-180 (1998).
Yamazaki et al., Single nucleotide polymorphisms in TNFSF15 confers susceptibility to Crohn's disease. Hum Mol Genet 14:3499-3506 (2005).
Yang et al., Association of intercellular adhesion molecule-1 (ICAM-1) gene with subsets of Inflammatory Bowel Disease (IBO) stratified by anti-neutrophil cytoplasmic antibodies I (AN CAs). Clinical Research Abstract only 42(1):76A (1994).
Yang et al., Familial empirical risks for inflammatory bowel disease: differences between Jews and non-Jews. Gut 34:517-524 (1993).
Yang et al., Genetic Heterogeneity within UC and Crohn's defined by anti-neutrophil cytoplasmic antibodies (AN CAs) and intercellular adhesion molecule-1 (ICAM-1) polymorph isms. Gastroenterology 106(4):A794 AGA Abstract (1994).
Yang et al., Intercellular adhesion molecule 1 gene association with immunologic subsets of inflammatory bowel disease. Gastroenterology 109:440-448 (1995).
Yang et al., Linkage of Crohn's disease to the major histocompatibility complex region is detected by multiple non-parametric analyses. Gut. 44 p. 519-526 (1999).
Yang et al. The R241 allele if ICAM-1 is associated with a distinct clinical subgroup of Crohn's disease (CD) characterized by perinuclear ANCA (pANCA) production. Abstract only. American Gastroenterological Association and American Association for the study of Liver disease. May 19-22, 1996.
Yang et al., Ulcerative colitis: a genetically heterogenous disorder defined by genetic (HLA class II) and subclinical (antineutrophil cytoplasmic antibodies) markers J. Clin. Invest., 92:1080-1084 (1993).
Yoon et al., Decreased potency of the Vibrio cholerae sheathed flagellum to trigger host innate immunity. Infection and Immunity 76:1282-1288 (2008).
Younes et al., Clinical implication of the tumor necrosis factor family in benign and malignant hematologic disorders. Cancer 98:458-467 (2003).
Younes et al., Emerging applications of the tumor necrosis factor family if ligands and receptors in cancer therapy. J Clin Oncol 21:3526-3534, (2003).
Zaahl et al., Analysis of the three common mutations in the CARD15 gene (R702W, G908R and 1007fs) in South African colored patients with inflammatory bowel disease. Molecular and Cellular Probes 19:278-281 (2005).
Zhang et al., Critical role of IL-17 receptor signaling in acute TNBS-induced colitis. Inflamm Bowel Dis 12:382-388 (2006).
Zhang et al. Estrogen affects the differentiation and function of splenic monocyte-derived dendritic cells from normal rats. Abstract Only. 20:129-134 (2004).
Ziegler et al., Detectable serum flagellin and liposaccharide and upregulated anti-flagellin and liposaccharide immunoglobulins in human short bowel syndrome. Am J Physiol Regul IntegrComp Physiol. 294:R402-R410 (2008).
Springer, T. A. et al., Leukocyte adhesion molecules structure function and regulation. New York, Springer-Verlag 1990 Book—Table of Contents Book not included.
Stratagene Catalog. 1988; p. 39. Gene Characterization Kits. Table of Contents.
Strong, S. Surgical management of Crohn's disease. in: Surgical Treatment: Evidence Based and Problem Oriented. Holzheimer and Mannick, editors. Munich: Zuckschwerdt, 7 pages, 2001.
Sulston et al., GeneBank Accession No. AC093601 retrieved from: http://www.ncbi.nlm.nih.gov/nuccore/AC093601 on Aug. 30, 2012.
Syvanen, Ann-Christine. Assessing genetic variation: Genotyping single nucleotide polymorphisms. Nature Reviews, 2:930, 2001.
Takedatsu et al., TL1A (TNFSF15) regulates the development of chronic colitis by modulating both T-helper 1 and T-helper 17 activation. Gastrornterology, 135(2):552-567, 2008.
Targan et al., TL1A (TNFSFI5): A Master Regulator of Mucosal Inflammation, Advances in Experimental Medicine and Biology, 691:681-683, 2011.
Taylor et al., ANCA pattern and LTA haplotype relationship to clinical responses to anti-TNF antibody treatment in Crohn's disease. Gastroenterology, 120:1347-1355, 2001.
Taylor et al., Specific clinical and immunological features in Crohn's disease patients are associated with the MHC class III marker Notch4. Gastroenterology. 118(Supp 2):A869, Abstract 4830 (2000).
The Wellcome Trust Case Control Consortium, Genome-Wide Association Study of 14,000 Cases of Seven Common Diseases and 3,000 Shared Controls, Nature, 2007, vol. 447, pp. 661-683.
Thomas et al., The TNF Family Member TL1A induces IL-22 Secretion in Committed Human TH17 Cells Via IL-9 nduction, Journal of Leukocyte Biology, 101:1-20, 2016.
Tomlinson I. and Holliger P. Methods for generating multivalent and bispecific antibody fragments. Methods Enzymol 326:461-479, 2000.
Toomajian et al., Sequence Variation and Haplotype Structure at the Human HFE Locus, Genetic Society of America, 2002, vol. 161(19), pp. 1609-1625.
Udenfriend et al., Fluorescence Characteristics of Purines, Pyrimidines and Their Derivatives: Measurement of Guanine in Nucleic Acid Hydrolzates, Analytical Biochemistry, 1962, vol. 3, pp. 49-59.
U.S. Appl. No. 09/395,345 Office Action dated May 9, 2001.
U.S. Appl. No. 09/419,408 Office Action dated May 30, 2002.
U.S. Appl. No. 09/419,408 Office Action dated Nov. 14, 2002.
U.S. Appl. No. 12/032,442 Restriction Requirement dated May 11, 2010.
U.S. Appl. No. 12/196,505 Final Office Action dated Dec. 7, 2012.
U.S. Appl. No. 12/196,505 Final Office Action dated Nov. 4, 2011.
U.S. Appl. No. 12/196,505 Final Office Action dated Nov. 9, 2010.
U.S. Appl. No. 12/196,505 Non-Final Office Action dated Apr. 12, 2010.
U.S. Appl. No. 12/196,505 Non-Final Office Action dated Jun. 14, 2013.
U.S. Appl. No. 12/196,505 Non-Final Office Action dated Mar. 25, 2011.
U.S. Appl. No. 12/196,505 Non-Final Office Action dated May 15, 2012.
U.S. Appl. No. 12/196,505 Restriction Requirement dated Apr. 23, 2009.
U.S. Appl. No. 12/527,376 Final Office Action dated May 25, 2012.
U.S. Appl. No. 12/527,376 Office Action dated Oct. 19, 2011.
U.S. Appl. No. 12/527,376 Restriction Requirement dated Sep. 1, 2011.
U.S. Appl. No. 12/528,055 Office Action dated Jul. 21, 2014.
U.S. Appl. No. 12/528,055 Office Action dated Apr. 30, 2015.
U.S. Appl. No. 12/528,055 Office Action dated Mar. 1, 2016.
U.S. Appl. No. 12/528,055 Office Action dated Mar. 27, 2012.
U.S. Appl. No. 12/528,055 Restriction Requirement dated Apr. 6, 2011.
U.S. Appl. No. 12/528,668 Final Office Action dated Mar. 21, 2012.
U.S. Appl. No. 12/528,668 Non-Final Office Action dated Sep. 25, 2013.
U.S. Appl. No. 12/528,668 Office Action dated Sep. 2, 2011.
U.S. Appl. No. 12/528,668 Restriction Requirement dated May 18, 2011.
U.S. Appl. No. 12/529,106 Office Action dated Oct. 14, 2011.
U.S. Appl. No. 12/675,718 Office Action dated Feb. 6, 2013.
U.S. Appl. No. 12/675,718 Restriction Requirement dated Aug. 7, 2012.
U.S. Appl. No. 13/130,998 Office Action dated Apr. 29, 2015.
U.S. Appl. No. 13/130,998 Office Action dated Aug. 14, 2015.
U.S. Appl. No. 13/130,998 Office Action dated Feb. 21, 2017.
U.S. Appl. No. 13/130,998 Office Action dated Feb. 4, 2014.

(56) References Cited

OTHER PUBLICATIONS

U.S. Appl. No. 13/130,998 Office Action dated Jun. 13, 2016.
U.S. Appl. No. 13/130,998 Office Action dated Oct. 4, 2017.
U.S. Appl. No. 13/130,998 Office Action dated Sep. 16, 2013.
U.S. Appl. No. 13/140,874 Restriction Requirement dated Feb. 22, 2013.
U.S. Appl. No. 13/263,707 Office Action dated Apr. 6, 2015.
U.S. Appl. No. 13/263,707 Office Action dated Aug. 1, 2014.
U.S. Appl. No. 13/263,707 Office Action dated Dec. 22, 2015.
U.S. Appl. No. 13/263,707 Office Action dated Feb. 26, 2014.
U.S. Appl. No. 13/263,707 Office Action dated Jul. 6, 2017.
U.S. Appl. No. 13/263,707 Office Action dated Jun. 19, 2013.
U.S. Appl. No. 13/263,707 Office Action dated Jun. 27, 2016.
U.S. Appl. No. 13/263,707 Office Action dated Nov. 28, 2016.
U.S. Appl. No. 13/263,707 Office Action dated Sep. 17, 2018.
U.S. Appl. No. 13/372,359 Office Action dated Jan. 12, 2016.
U.S. Appl. No. 13/372,359 Office Action dated Jan. 23, 2015.
U.S. Appl. No. 13/372,359 Office Action dated Jul. 21, 2016.
U.S. Appl. No. 13/372,359 Office Action dated Jul. 27, 2015.
U.S. Appl. No. 13/372,359 Office Action dated Jun. 23, 2014.
U.S. Appl. No. 13/372,359 Office Action dated Jun. 8, 2017.
U.S. Appl. No. 13/372,359 Office Action dated Nov. 17, 2016.
U.S. Appl. No. 14/722,018 Office Action dated May 12, 2017.
U.S. Appl. No. 14/722,018 Office Action dated Nov. 14, 2017.
U.S. Appl. No. 14/847,705 Office Action dated Sep. 8, 2017.
U.S. Appl. No. 14/890,699 Office Action dated Mar. 7, 2018.
U.S. Appl. No. 14/890,699 Office Action dated May 19, 2017.
U.S. Appl. No. 14/890,712 Office Action dated Dec. 6, 2017.
U.S. Appl. No. 14/915,544 Office Action dated Mar. 22, 2018.
U.S. Appl. No. 15/245,875 Office Action dated Jan. 18, 2018.
U.S. Appl. No. 15/792,266 Office Action dated Aug. 6, 2018.
U.S. Appl. No. 13/130,998 Office Action dated Apr. 2, 2018.
Verhoeyen et al. Reshaping human antibodies: Grafting an antilysozyme activity. Science 239:1534-1536, 1988.
Vermeire et al., Current Status of Genetics Research in Inflammatory Bowel Disease, Genes and Immunity, 2005, vol. 6, pp. 637-645.
Walder et al. Oligodeoxynucleotide-directed mutagenesis using the yeast transformation system. Gene 42:133-139, 1986.
Wall et al., Haplotype Blocks and Linkage Disequilibrium in the Human Genome, Nature Reviews Genetics, 2003, vol. 4, pp. 587-597.
Wang et al., Diverse Genome-Wide Association Studies Associate the IL12/IL23 pathway with Crohn Disease, Am J. Hum. Genet., 2009, vol. 84(3), pp. 399-405.
Ward et al. Binding activities of a repertoire of single immunoglobulin variable domains secreted from *Escherichia coli*. Nature 334:544-54, 1989.
Whisnant et al., Rheumatoid Arthritis: Treatment with Azathiorprine (IMURAN (R)), Clinical Side-Effects and Laboratory Abnormalities, Ann Rheum Dis., 1982, vol. 41, pp. 44-47.
Wu et al., Genome-wide gene expression differences in Crohn's disease and ulcerative colitis from endoscopic pinch biopsies: Insights into distinctive pathogenesis. Inflammatory Bowel Disease, 13:807-821, 2007.
Yamazaki et al., Positive Association of Genetic Variants in the Upstream Region of NKX2-3 with Crohn's Disease in Japanese Patients, Gut, 2009, vol. 58, pp. 228-232.
Yang et al. Genetic aspects of idiopathic inflammatory bowel disease. Kirschner and Shorter (Eds.), Inflammatory Bowel Disease Baltimore: Williams and Wilkins pp. 301-331 (1995).
Yang et al. The R241 allele of ICAM-1 is associated with a distinct clinical subgroup of Crohn's disease (CD) characterized by perinuclear ANCA (pANCA) production. Abstract only. American Gastroenterological Association and American Association for the study of Liver disease. May 19-22, 1996.
Yeager et al., Genome-wide association study of prostate cancer identifies a second risk locus at 8q24. Nature Genetics, 39(5):645-649, 2007.
Yoon et al. Colonic Phenotypes Are Associated with Poorer Response to Anti-TNF Therapies in Patients with IBD. Inflammatory Bowel Diseases. 23(8):1382-1393 (2017).
Zill et al., SNP and Haplotype Analysis of a Novel Tryptophan Hydroxylase Isoform (TPH2) Gene Provide Evidence for Association with Major Depression, Molecular Psychiatry, 2004, vol. 9, pp. 1030-1036.
Adams et al., Two-stage genome-wide methylation profiling in childhood-onset Crohn's Disease implicates epigenetic alterations at the VMP1/MIR21 and HLA loci. lnflamm Bowel Dis. 20(10):1784-1793 (2014).
Bamias et a., Expression, localization, and functional activity of TL1A, a novel Th1-polarizing cytokine in inflammatory bowel disease. Journal of Immunology 171(9):4868-4874 (2003).
Co-pending U.S. Appl. No. 15/795,185, filed Oct. 26, 2017.
Co-pending U.S. Appl. No. 16/084,858, filed Sep. 13, 2018.
European Patent Application No. 18201967.9 European Search Report dated Mar. 6, 2019.
European Patent Application No. 14826746.1 Examination Report dated Mar. 13, 2019.
Fransen et al., Inflammatory bowel disease: the genetic background and beyond. University of Groningen PhD Dissertation http://www.rug.nl/research/portal/files/12805965/Complete_dissertation.pdf (2014).
Heusch et al., IL-9 exacerbates colitis induced by CD4+ CD45RBhigh T cells transfer, via directed activation of in vivo antigen-experienced T cells. Cytokine 56:PS1-056, p. 31 (2011).
Hundorean et al., Functional relevance of T helper 17 (Th17) cells and the IL-17 cytokine family in inflammatory bowel disease. Inflammatory Bowel Disease 18:180-186 (2012).
Japanese Patent Application No. 2016-505570 Office Action dated Oct. 24, 2018.
Japanese Patent Application No. 2016-514143 Notice of Allowance dated Jan. 30, 2019.
Japanese Patent Application No. 2016-514143 Office Action dated Oct. 23, 2018.
Funke et al.: Functional characterisation of decoy receptor 3 in Crohn's disease; Gut 58(40): 483-491 (2009).
Goswami et al.: A Brief History of IL-9; The Journal of Immunology; 186; 3283-3288 (2019).
McGovern et al., Genetics of inflammatory bowel diseases. Gastroenterology 149(5):1163-1173 (2015).
Nalleweg et al., Inflammatory bowel disease patients failing anti-TNF therapy show activation of the Th9/TH17 pathway. Gastroenterol 142(5)(Suppl1):S867-868; Abstract No. Tu1878 (2012).
NCBI Blast sequence search for SEQ ID No. 7; retrieved from: https://blast.ncbi.nlm.nih.gov/Blast.cgi on Sep. 12, 2018 (3 pgs.).
Nowak et al., IL-9 as a mediator of Th17-driven inflammatory disease. Journal of Experimental Medicine 206(8):1653-1660 (2009).
Oh et al., A randomized, controlled trial to evaluate the effect of an anti-interleukin-9 monoclonal antibody in adults with uncontrolled asthma. Respiratory Research 14:93 (2013).
PCT/US2017/023082 International Search Report and Written Opinion dated Aug. 15, 2017.
Chinese Patent Application No. 201480038133.6 Second Office Action dated Jan. 21, 2019.
NCBI SNP ID rs7374667 (2011).
Papadakis et al., An interaction between IL-23R and IL-17A and between IL-23R and IL 17RA haplotypes is necessary for susceptibility to Crohn's disease. Abstract only. (2007) AGA Institute.
Papadakis et al., Phenotypic and functional characterization of CCR9+ T lymphocytes in small intestinal Crohn's disease. Abstract only. (2006). www.crohnscolitisfoundation.org/assets/.../111-2005_investigator_meeting-papadakis.
UCSC Genome Browser Assembly-SNP Genotyping Arrays retrieved from: http://genome.com.csdb.cn/cgi-bin on Mar. 21, 2014 (original document can be found in related U.S. Appl. No. 13/144,376).
U.S. Appl. No. 15/557,213 Restriction Requirement dated May 21, 2019.
U.S. Appl. No. 15/868,763 Office Action dated Feb. 21, 2019.
U.S. Appl. No. 15/868,763 Restriction Requirement dated Dec. 6, 2108.

(56) References Cited

OTHER PUBLICATIONS

US13130998_52388-707-831_Notice of Abandonment_Dec. 17, 2018.
Chu et al.: A genome-wide association study identifies two new risk loci for Graves' disease. Nature Genetics; 43/9:897-901 (2011).
European Patent Application No. 17767679.8 Supplementary European Search Report dated Jul. 22, 2019.
Jostins et al.: Host-microbe interactions have shaped the genetic architecture of inflammatory bowel disease. Nature; 491/7422:119-124 (2012).
U.S. Appl. No. 15/868,763 Final Office Action dated Oct. 1, 2019.

* cited by examiner e f

TREATMENT AND REVERSAL OF FIBROSIS AND INFLAMMATION BY INHIBITION OF THE TL1A-DR3 SIGNALING PATHWAY

CROSS-REFERENCE TO RELATED APPLICATIONS

This application is a National Phase of International Application No. PCT/US2014/032054, filed Mar. 27, 2014, currently pending, which designated the U.S. and that International Application was published under PCT Article 21(2) in English. This application also includes a claim of priority under 35 U.S.C. § 119(e) to U.S. provisional patent application No. 61/805,806, filed Mar. 27, 2013, now expired, and U.S. provisional patent application No. 61/872,020, filed Aug. 30, 2013, now expired, the entirety of which are hereby incorporated by reference.

FIELD OF INVENTION

The invention provides methods and compositions for the treatment and diagnosis of conditions related to TL1A function and fibrosis.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Crohn's disease (CD) is a chronic inflammatory condition with pathological features such as patchy transmural inflammation and fibrostenosis. Despite potent anti-inflammatory therapies, up to 20% of CD patients still develop structuring complications that require surgical intervention. Pathways that regulate fibrosis may be distinct from those mediating inflammation. TL1A, a member of the TNF superfamily, binds to death domain receptor 3 (DR3) and modulates the adaptive immune response. TL1A may be associated with CD, intestinal fibrostenosis, and greater need for surgery. There is a need for novel and effective therapeutics for the treatment of diseases associated with the TL1A/DR3 signaling pathway, CD, as well as associated complications including therapeutics for reversal of established fibrosis.

SUMMARY OF THE INVENTION

Various embodiments herein include a method of treating fibrosis in a subject, comprising providing a composition comprising one or more inhibitors of TL1A function, and administering a therapeutically effective dosage of the composition to the subject. In other embodiments, the composition comprises one or more TL1A blocking antibodies. In another embodiment, the composition comprises one or more Dr3 blocking antibodies. In another embodiment, the composition comprises one or more compounds that inhibit TL1A function by directly binding to TL1A. In another embodiment, the composition comprises one or more inhibitors of Ifngamma, IL17, Ctgf and IL31Ra. In another embodiment, the composition comprises one or more inhibitors of Tgfbeta1 and Igf1. In another embodiment, the composition comprises one or more inhibitors of IL31 signaling. In another embodiment, administering a therapeutically effective dosage of the composition results in reversal of the fibrosis to pre-inflamed levels. In another embodiment, the fibrosis is colonic fibrosis. In another embodiment, administering a therapeutically effective dosage of the composition further results in inhibition of gut inflammation in the subject.

Other embodiments include a method of treating a disease in a subject, comprising providing a composition comprising an inhibitor of IL31Ra signaling, and administering an effective dosage of the composition to the subject. In another embodiment, the disease is a TL1A associated disease. In another embodiment, the disease is Inflammatory Bowel Disease (IBD). In another embodiment, the disease is associated with strictures developed in the small intestine and/or gut inflammation. In another embodiment, the disease is small and large intestinal fibrostenosis. In another embodiment, the disease is fibrosis. In another embodiment, the composition comprises one or more TL1A antibody. In another embodiment, the composition comprises one or more inhibitors of IL31RA, IFNgamma, IL17, Ctgf, TgfB1 and/or Igf1 signaling.

Other embodiments include a method of diagnosing susceptibility to a TL1A associated disease in a subject, comprising obtaining a sample from the subject, assaying the sample to determine the presence or absence of a high level of IL31Ra expression relative to a normal individual, and diagnosing susceptibility to the TL1A associated disease based on the presence of the high level of IL31 expression relative to a normal individual. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the method further comprises determining the presence of a high level of expression relative to a normal individual of IL31RA, IFNgamma, IL17, Ctgf, TgfB1 and/or Igf1.

Various embodiments include a method of diagnosing a TL1A associated disease in a subject, comprising obtaining a sample from the subject, assaying the sample to determine the presence or absence of one or more risk variants and/or markers associated with the TL1A associated disease, and diagnosing the TL1A associated disease based on the presence of one or more risk variants and/or markers associated with the TL1A associated disease. In another embodiment, the one or more risk variants and/or markers include a high expression of IL31RA. Other embodiments include one or more risk variants and/or markers that include a high expression of IFNgamma, IL17, Ctgf, TgfB1 and/or Igf1. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the method further comprises treating the TL1A associated disease by administering one or more TL1A inhibitors. In another embodiment, the method further comprises treating the TL1A associated disease by administering a TL1A inhibitor. In another embodiment, the subject is human. In another embodiment, the method further comprises treating the TL1A associated disease by administering a Dr3 inhibitor.

Other embodiments include a method of treating fibrosis in a subject, comprising providing a composition comprising a TL1A inhibitor and DR3 inhibitor, and administering a therapeutically effective dosage of the composition to the subject. In another embodiment, the TL1A inhibitor is a TL1A antibody.

Other embodiments include a method of reversing fibrosis in a subject, comprising providing a composition comprising a TL1A inhibitor and DR3 inhibitor, and administering a therapeutically effective dosage of the composition to the subject. In another embodiment, the composition further comprises an inhibitor of IFNgamma, IL17, Ctgf and/or IL31RA signaling function.

Various embodiments include a method of treating inflammation, comprising providing a composition comprising a TL1A inhibitor and/or DR3 inhibitor, and administering a therapeutically effective dosage of the composition to the subject. In another embodiment, the composition further comprises an inhibitor of IFNgamma, IL17, Ctgf and/or IL31RA signaling function.

Other embodiments include a method of treating a disease in a subject, comprising inhibiting Ifnγ and Il-17 expression, down-regulating Tgfβ signaling, and/or reducing fibroblast/myofibroblast, and treating the subject. In another embodiment, the disease is inflammatory bowel disease. In another embodiment, the disease is fibrosis. In another embodiment, the disease gut inflammation. In another embodiment, the disease is complications associated with inflammatory bowel disease.

Other embodiments include a composition comprising one or more inhibitors of TL1A, DR3 and IL31RA signaling function, and a pharmaceutically acceptable carrier. In another embodiment, the one or more TL1A inhibitors is a TL1A antibody. In another embodiment, the one or more DR3 inhibitors is a DR3 antibody.

Various embodiments herein include a method of treating complications associated with IBD, comprising providing a composition comprising an inhibitor of TL1A, DR3 and IL31RA signaling function, and administering a therapeutically effective dosage of the composition to the subject. In another embodiment, the composition is administered intravenously to the subject.

BRIEF DESCRIPTION OF THE FIGURES

Exemplary embodiments are illustrated in referenced figures. It is intended that the embodiments and figures disclosed herein are to be considered illustrative rather than restrictive.

FIG. 13(a) shows that there is a direct correlation between Dr3 expression and alphaSMA expression. This is important to show that fibroblasts with higher alpha SMA expression (more active fibroblasts) has higher (Dr3 expression), indicating that these more active fibroblasts are more receptive to Tl1a signaling. For this experiment, the inventors have gated on the alpha SMA low, intermediate and high expressing myofibroblasts separately and then displayed the proportion of cells expressing Dr3 (FIG. 13a). The figure illustrates that Dr3 is expressed in αSMA high>αSMA intermediate>αSMA low fibroblasts. (b) Data are representative of 3 independent sorted αSMA positive myofibroblasts at 200× magnification. There was co-staining of Dr3 in WT, but not in Dr3 deficient αSMA positive myofibroblasts. Specifically, FIG. 13(b) shows directly that Dr3, the receptor for Tl1a, is expressed on myofibroblasts. This is important to show that myofibroblasts which mediates fibrosis can receive signaling from Tl1a. To do this experiment, the inventors sorted for αSMA positive cells that were stained with anti-alpha SMA and DR3 antibody. They then showed that Dr3 is expressed on αSMA positive WT but not DR3 KO myofibroblasts using immunofluorescence microscopy (FIG. 13b). (c) Expression of Col1a2 and Il31Ra mRNA in WT primary intestinal fibroblasts with increasing Tl1a stimulation (0-200 ng/mL) and represented as mean±SD are shown (n=3). (d) Induction of Col1a2 and Il31Ra mRNA by Tl1a, Tgfβ/Igf1, and Tnfα in WT and Dr3−/− intestinal are shown and represented as mean±SD (n=3). *P<0.05, **P<0.01. Specifically, FIG. 13(d) shows additional experiments to enhance the in vitro experiments (FIG. 13d). The inventors used Tgfβ and Igf1 as prototypical fibroblast growth factors and showed that there is no difference in the induction of Col1a2 and Il31Ra expression between WT and Dr3 deficient primary intestinal fibroblasts (FIG. 13d). They used Tnfα as the prototypical proinflammatory stimuli and showed that there is no difference in the induction of Col1a2 and Il31Ra comparing WT and Dr3 deficient primary intestinal fibroblasts. This is in contrast to stimulation with Tl1a where there is significant induction of Col1a2 and Il31Ra expression in the WT as compared to Dr3 deficient primary intestinal fibroblasts.

DESCRIPTION OF THE INVENTION

Figure 1:
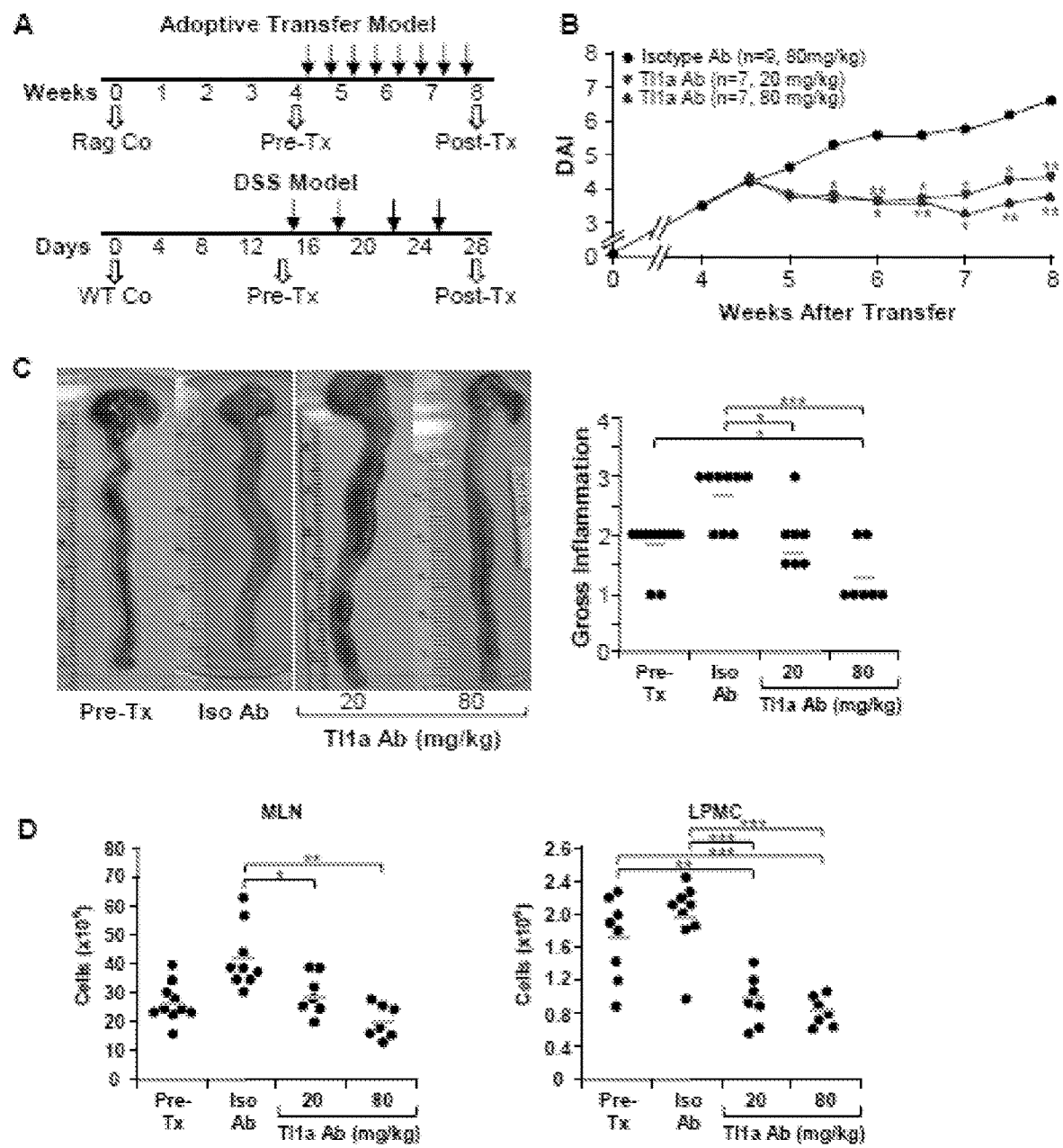
FIG. 1 depicts, in accordance with an embodiment herein, Tl1a Ab reduced colonic disease features. (A) Tl1a Ab treatment schematics for adoptive transfer model; baseline Rag−/− control mice (Rag Co), baseline wildtype control mice (WT Co), pre-treatment group (Pre-Tx), isotype antibody group (Iso Ab), post treatment group (Post-Tx). (B) DAI is compared between Iso and Tl1a Ab treated groups. (C) Representative gross appearance of colon (left panels) with the quantitative inflammatory scores (right panel) are shown. Data are expressed as mean±SD. (D) Total numbers of mononuclear cells were isolated from MLN and LPMC. Each filled circle represents an independent mouse. Tl1a Ab treated groups are compared to Pre-Tx and Iso Ab group. $*p<0.05$, $p<0.01$, $*p<0.001$.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 4th ed., J. Wiley & Sons (New York, N.Y. 2012); March, Advanced Organic Chemistry Reactions, Mechanisms and Structure 5th ed., J. Wiley & Sons (New York, N.Y. 2001); and Sambrook and Russel, Molecular Cloning: A Laboratory Manual 4th ed., Cold Spring Harbor Laboratory Press (Cold Spring Harbor, N. Y. 2012); provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As disclosed herein, intestinal fibrostenosis is among the hallmarks of severe Crohn's disease. Patients with certain TNFSF15 variants over-express TL1A and have a higher risk of developing strictures in the small intestine. Additionally, mice with sustained Tl1a expression led to small and large intestinal fibrostenosis under colitogenic conditions. The inventors investigated whether neutralizing Tl1a function can reverse established murine colitis and colonic fibrosis.

As further disclosed herein, Tl1a blocking antibody (12F6A) or isotype control Ig was administered to mice with established chronic murine colitis and colonic fibrosis. Mice with Dr3 deficiency (Dr3−/−) were generated. Primary murine intestinal fibroblasts were isolated. Histological and immunofluorescent staining, flow cytometry, ELISA, and mRNA level were used to compare the degree of inflammation and fibrosis. CellTrace and Annexin V stains were used to determine cell proliferation and apoptosis, respectively. The inventors found that treatment with Tl1a antibody mitigated murine colitis and reversed colonic fibrosis back to the original pre-inflamed levels. This could be due to lowered Ifnγ, Il17, Ctgf, Il31Ra expression and down-regulation of Tgfβ1 and Igf1 signaling. Additionally, blocking Tl1a function led to reduced number of fibroblast and myofibroblast. Primary intestinal myofibroblasts express Dr3 and can functionally respond to direct Tl1a signaling by increasing collagen and Il31Ra expression. In conclusion, modulation of TL1A signaling inhibits both gut inflammation and fibrosis.

In one embodiment, the present invention provides a method of treating a disease in a subject, comprising providing a composition comprising an inhibitor of IL31 signaling, and administering an effective dosage of the composition to the subject. In another embodiment, the disease is a TL1A associated disease. In another embodiment, the disease is Inflammatory Bowel Disease (IBD). In another embodiment, the disease is associated with strictures developed in the small intestine and/or gut inflammation. In another embodiment, the disease is small and large intestinal fibrostenosis. In another embodiment, the disease is fibrosis. In another embodiment, the composition comprises one or more TL1A antibody. In another embodiment, the composition comprises one or more inhibitors of IL31RA, IFNgamma, IL17, Ctgf, TgfB1 and/or Igf1 signaling.

In another embodiment, the present invention provides a method of treating a disease in a subject, comprising providing a composition comprising an inhibitor of IL31Ra signaling, and administering an effective dosage of the composition to the subject. In another embodiment, the disease is a TL1A associated disease. In another embodiment, the disease is Inflammatory Bowel Disease (IBD). In another embodiment, the disease is associated with strictures developed in the small intestine and/or gut inflammation. In another embodiment, the disease is small and large intestinal fibrostenosis. In another embodiment, the disease is fibrosis. In another embodiment, the composition comprises one or more TL1A antibody. In another embodiment, the composition comprises one or more inhibitors of IL31RA, IFNgamma, IL17, Ctgf, TgfB1 and/or Igf1 signaling. In another embodiment, administering a therapeutically effective dosage of the composition decreases the number of fibroblasts and/or myofibroblasts in the subject.

In one embodiment, the present invention provides a method of diagnosing susceptibility to a TL1A associated disease in a subject, comprising obtaining a sample from the subject, assaying the sample to determine the presence or absence of a high level of IL31 expression relative to a normal individual, and diagnosing susceptibility to the TL1A associated disease based on the presence of the high level of IL31 expression relative to a normal individual. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the method further comprises determining the presence of a high level of expression relative to a normal individual of IL31RA, IFNgamma, IL17, Ctgf, TgfB1 and/or Igf1.

A method of diagnosing susceptibility to a TL1A associated disease in a subject, comprising obtaining a sample from the subject, assaying the sample to determine the presence or absence of a high level of IL31Ra expression relative to a normal individual, and diagnosing susceptibility to the TL1A associated disease based on the presence of the high level of IL31RA expression relative to a normal individual. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the present invention further comprises determining the presence of a high level of expression relative to a normal individual of collagen, IL31RA, IFNgamma, IL17, Ctgf, TgfB1 and/or Igf1.

In another embodiment, the present invention provides a method of diagnosing a TL1A associated disease in a subject, comprising obtaining a sample from the subject, assaying the sample to determine the presence or absence of one or more risk variants and/or markers associated with the TL1A associated disease, and diagnosing the TL1A associated disease based on the presence of one or more risk variants and/or markers associated with the TL1A associated disease. In another embodiment, the one or more risk variants and/or markers include a high expression of IL31RA. In another embodiment, the one or more risk variants and/or markers include a high expression of IFNgamma, IL17, Ctgf, TgfB1 and/or Igf1. In another embodiment, the TL1A associated disease is Inflammatory Bowel Disease (IBD). In another embodiment, the TL1A associated disease is associated with strictures developed in the small intestine and/or gut inflammation. In another embodiment, the TL1A associated disease is small and large intestinal fibrostenosis. In another embodiment, the TL1A associated disease is fibrosis. In another embodiment, the method further comprises treating the TL1A associated disease by administering one or more TL1A inhibitors. In another embodiment, the method further comprises treating the TL1A associated disease by administering a TL1A inhibitor. In another embodiment, the subject is human. In another embodiment, the method further comprises treating the TL1A associated disease by administering a Dr3 inhibitor.

As disclosed herein, in two distinct chronic colitis models, it was shown that Tl1a Ab ameliorated colitic disease and reversed intestinal fibrosis. Modulation of TL1A signaling can alter the natural history of Crohn's disease by treating both gut inflammation and fibrosis. Blocking the TL1A/DR3 signaling pathway provides a therapeutic approach for the treatment of Crohn's disease and its associated complications including reversal of established fibrosis.

In one embodiment, the present invention provides a method of treating fibrosis associated with inflammatory bowel disease (IBD) in a subject by diagnosing fibrosis in the subject, and then administering one or more inhibitor of TL1A-DR3 signaling function, such as by administering a therapeutically effective TL1A antibody, or deleting DR3 expression, or dsRNA or siRNA coding for TL1A expression (expression of TNFSF15). Or, in other embodiments, by inhibiting one or more molecules downstream of TL1A-DR3.

In one embodiment, the present invention provides a method of treating a disease by administering a composition comprising a therapeutically effective dosage of TL1A inhibitor and/or DR3 inhibitor to the subject. In another embodiment, the disease is fibrosis. In another embodiment, the disease is inflammatory bowel disease. In another embodiment, the disease is Crohn's disease. In another embodiment, the disease is colitis. In another embodiment, the subject is a human. In another embodiment, the TL1A inhibitor is a TL1A antibody. In another embodiment, the DR3 inhibitor is a DR3 antibody.

In another embodiment, the present invention provides a method of reversing fibrosis in an individual by administering a composition comprising a therapeutically effective dosage of TL1A inhibitor and/or DR3 inhibitor to the subject.

In another embodiment, the present invention provides a method of treating fibrosis in a subject, comprising providing a composition comprising one or more inhibitors of TL1A-DR3 signaling function, and administering a therapeutically effective dosage of the composition to the subject. In another embodiment, the composition comprises one or more TL1A blocking antibodies. In another embodiment, the composition comprises one or more Dr3 blocking antibodies. In another embodiment, the composition comprises one or more compounds that inhibit TL1A function by directly binding to TL1A. In another embodiment, the composition comprises one or more inhibitors of Ifngamma, IL17, Ctgf and IL31Ra. In another embodiment, the composition comprises one or more inhibitors of Tgfbeta1 and Igf1. In another embodiment, the composition comprises one or more inhibitors of IL31 signaling. In another embodiment, administering a therapeutically effective dosage of the composition results in reversal of the fibrosis to pre-inflamed levels. In another embodiment, the fibrosis is colonic fibrosis. In another embodiment, administering a therapeutically effective dosage of the composition further results in inhibition of gut inflammation in the subject. In another embodiment, administering a therapeutically effective dosage of the composition decreases the number of fibroblasts and/or myofibroblasts in the subject. In another embodiment, administering a therapeutically effective dosage of the composition decreases the number of primary intestinal myofibroblasts in the subject.

In one embodiment, the present invention provides a method of treating fibrosis in a subject, comprising providing a composition comprising a TL1A inhibitor and a DR3 inhibitor; and administering a therapeutically effective dosage of the composition to the subject. In another embodiment, the TL1A inhibitor is a TL1A antibody. In another embodiment, the DR3 inhibitor deletes expression of DR3. In another embodiment, the fibrosis is decreased. In another embodiment, the composition inhibits TL1A-DR3 signaling function.

In one embodiment, the present invention provides a method of reversing fibrosis in a subject, comprising providing a composition comprising a TL1A inhibitor and a DR3 inhibitor, and administering a therapeutically effective dosage of the composition to the subject. In another embodiment, the composition further comprises an inhibitor of IFNgamma, IL17, Tgfbeta1, Ctgf and/or IL31RA signaling function. In another embodiment, the composition inhibits TL1A-DR3 signaling function.

In one embodiment, the present invention provides a method of treating inflammation, comprising providing a composition comprising a TL1A inhibitor and/or DR3 inhibitor, and administering a therapeutically effective dosage of the composition to the subject. In another embodiment, the composition further comprises an inhibitor of IFNgamma, IL17, Ctgf and/or IL31RA signaling function. In another embodiment, the composition inhibits TL1A-DR3 signaling function.

In one embodiment, the present invention provides a method of treating a disease in a subject, comprising inhibiting Ifnγ and Il-17 expression, down-regulating Tgfβ signaling, and/or reducing fibroblast/myofibroblast, and treating the subject. In another embodiment, the disease is inflammatory bowel disease. In another embodiment, the disease is fibrosis. In another embodiment, the disease gut inflammation. In another embodiment, the disease is complications associated with inflammatory bowel disease.

In one embodiment, the present invention provides a method of treating complications associated with IBD, comprising providing a composition comprising an inhibitor of TL1A, DR3 and IL31RA signaling function, and administering a therapeutically effective dosage of the composition to the subject. In another embodiment, the composition is administered intravenously to the subject.

In one embodiment, the present invention provides a composition comprising one or more TL1A inhibitors and/or one or more DR3 inhibitors, and a pharmaceutically acceptable carrier. In another embodiment, the one or more TL1A inhibitors are TL1A antibodies. In another embodiment, the one or more DR3 inhibitors are DR3 antibodies.

In another embodiment, the present invention provides a method of lowering inflammation in a subject by administering a composition comprising a therapeutically effective dosage of TL1A inhibitor and/or DR3 inhibitor to the subject.

In another embodiment, the present invention provides a method of inhibiting conditions associated with fibrosis by inhibiting Ifnγ and Il-17 expression, down-regulation of Tgfβ signaling, and/or reducing fibroblast/myofibroblast.

In one embodiment the present invention provides a composition comprising one or more inhibitors of TL1A, DR3 and IL31RA signaling function, and a pharmaceutically acceptable carrier. In another embodiment, the one or more TL1A inhibitors is a TL1A antibody. In another embodiment, the one or more DR3 inhibitors is a DR3 antibody.

There are many techniques readily available in the field for detecting the presence or absence of polypeptides or other markers/biomarkers, including protein microarrays. For example, some of the detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are any number of techniques that may be employed to isolate and/or fractionate biomarkers. For example, a biomarker may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as polypeptides maybe detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Induction of Chronic Colitis and Treatment

C57BL/6J mice were purchased from the Jackson Laboratory. Chronic dextran sodium sulfate (DSS) colitis was induced as described. 10 In the adoptive-transfer model, colitis was induced by intraperitoneal injection of 500,000 CD4+CD45RBhi naïve T-cells isolated from WT mice to Rag1−/− mice. Hamster anti-mouse Tl1a Ab (12F6A, TEVA, North Wales, Pa.) blocked the function of Tl1a and were administered at 20-, or 80-mg/kg or control immunoglobulin (Ig)G (Leinco Technologies, St. Louis, Mo.) at 80-mg/kg dose were injected intraperitoneally into mice twice per week beginning on day 15 for the chronic DSS and day 29 for the adoptive-transfer models (FIG. 1A). Baseline controls (Rag Co or WT Co) were mice analyzed prior to DSS treatment or adoptive transfer of naïve T-cells. Pretreatment (Pre-Tx) controls were mice analyzed at day 14 for the chronic DSS model and day 28 for the adoptive-transfer model. Treatment groups were mice analyzed at day 28 for the chronic DSS model and day 56 for the adoptive transfer model (FIG. 1A). All mice were maintained under specific pathogen-free conditions in the Animal Facility at Cedars-Sinai Medical Center (CSMC). This study was carried out in strict accordance with the Guide for the Care and Use of Laboratory Animals of the National Institutes of Health. Animal studies were approved by the CSMC Animal Care and Use Committee (protocol 3813).

Example 2

Disease Activity Index, Myeloperoxidase, Macroscopic and Histopathological Analyses Disease activity index (DAI) score was determined every other day for the DSS model and twice a week for the adoptive-transfer model as described. Myeloperoxidase activity was assessed using the Myeloperoxidase Fluorometric Detecton Kit according to the manufacturer's protocol (Enzo Life Sciences, Plymouth Meeting, Pa.). Macroscopic evidence of inflammation was scored blinded using the established classification. Tissue samples were processed and stained with hematoxylin and eosin (H&E) by the CSMC Histology-Core. Sirius red staining was performed using the NovaUltra Sirius Red Stain Kit according to manufacturer's protocol (IHC World, Woodstock, Md.). Immunofluorescent stain was performed on 4 μM frozen sections fixed with 10% formalin and stained with α-SMA Ab (Abcam) at 1:100 dilution and α-Vimentin Ab (Covance, San Diego, Calif.) at 1:2000 dilution with donkey α-rabbit IgG and goat α-chicken IgY (Abcam, Cambridge, Mass.) secondary Ab. Histopathological scores were assigned in a blinded manner by two trained animal pathologists (DQS and JC) as described. Observation of ≥5 different fields per gut region per mouse was used to determine histologic score and collagen deposition at 200× magnification and to count fibroblast/myofibroblast numbers at 630× magnification using a Leica TCS SP spectral confocal microscope.

Example 3

Generation of Dr3−/− Mice

Figure 5:
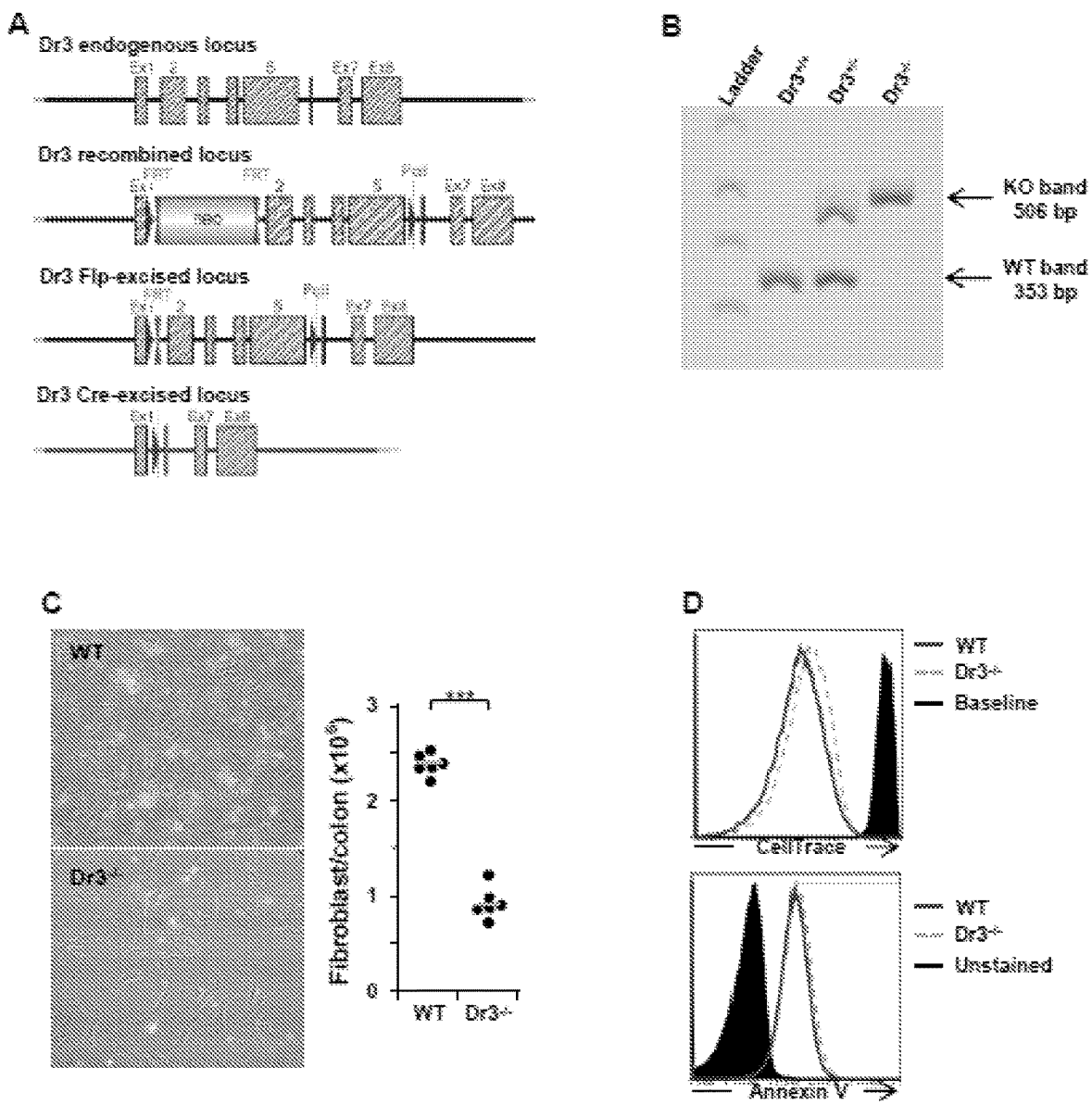
FIG. 5 depicts, in accordance with an embodiment herein, reduced proliferation of intestinal fibroblasts with Dr3 deficiency. (A) Schematic representation of mouse Dr3 endogenous locus and strategy for gene targeting. (B) Representative polymerase chain reaction for Dr3 genotype is shown with targeted (Dr3 KO) band running at 506 by and endogenous Dr3 locus running at 353 bp. (C) Representative of 6 photographs of intestinal fibroblasts recovered from littermate WT and Dr3−/− colon (left panels) and individual total fibroblasts per colon is plotted (right panel). (D) Representative flow cytometric histograms showing the quantification of proliferating fibroblasts (top panel) and fibroblasts undergoing apoptosis (bottom panel) from WT and Dr3−/− mice. Decreased CellTrace violet fluorescence intensity indicates proliferation. Increased Annexin V staining indicates apoptosis. Shown are representative flow cytometric histograms of at least 6 independent experiments with similar results. $***p<0.001$.

Cloning of Dr3 targeting vector and generation of Dr3+/− founder mice were performed in collaboration with genOway (genOway, Lyon, France). Briefly, Dr3 endogenous locus containing 1.5 kb upstream of exon 1 and 3 kb downstream of exon 8 were generated by PCR amplification using genomic DNA from C57BL/6J mice and cloned into the pCR4-TOPO vector (Invitrogen, Carlsbad, Calif.). Subsequently, two loxP sites were inserted flanking Dr3 exons 2 to 5 (FIG. 5A). Positive selection neomycin gene flanked by FRT sites was inserted to the intron between exon 1 and 2 to generate the targeting vector (FIG. 5A). Every step of the cloning process was validated through restriction analysis and sequencing. The Dr3 gene targeting construct was linearized and transfected into genOway proprietary embryonic stem (ES) cells with C57BL/6J background by electroporation. Homologous recombinants were selected by G418 and confirmed by Southern blot analysis. ES clones with correct 5' and 3' recombination were microinjected into C57BL/6J blastocysts and introduced into pseudopregnant C57BL/6J mice. Male chimeric offspring were bred to obtain germ line mutant mice which were then bred to Flpe delete mouse strain to remove the neomycin cassette, then bred to Cre delete mice to excise the loxP flanked sequences (FIG. 5A), confirmed by Southern blot, and maintained on the C57BL/6J genetic background.

Example 4

Expression Analysis

Total RNA was isolated using RNeasy Microarray Tissue Mini Kit (Qiagen, Valencia, Calif.), and reverse-transcription polymerase chain reaction (RT-PCR) was performed using RT2 HT First Strand and gene expression was measured using the RT2 Custom Fibrosis Array CAPM11248 (Qiagen, Valencia, Calif.) kits per manufacturer's protocols. Cytokine concentration was assayed using a multi-plex immunoassay, Mouse Th1/Th2/Th17/Th22 13plex Kit FlowCytomix (eBioscience, San Diego, Calif.) per manufacturer's protocol. Validated Dr3 qPCR assay Mm.PT.51.17321439, Il31Ra qPCR assay Mm.PT.56a.32787326 and β-actin qPCR assay Mm.PT.39a.22214843 were purchased from IDT Technologies (Skokie, Ill.).

Example 5

Cell Isolation, Culture, Intracellular Cytokine Expression, and Flow Cytometry

Isolation and culture of lamina propria mononuclear cells (LPMC), mesenteric lymph node (MLN), and splenic cells and their subsequent stimulation by anti-CD28 and anti-CD3ε were carried out. The inventors used the whole colon and the distal 10 cm of the ileum for LPMC isolation. Mouse primary colonic fibroblasts were isolated from colon that were incubated in 1 mM DTT (Fisher Scientific, Tustin, Calif.), 37° C., 15 min, and then 1 mM DTT with 5 mM EDTA (Promega, Madison, Wis.), 37° C., 30 min. The remaining colonic tissues were rinsed by 1×HBSS (Corning Cellgro, Swedesboro, N.J.), minced and then digested for 30 min at 37° C. with 1.5 mg/mL Collagenase II (Worthington, Lakewood, N.J.), 0.3 mg/mL DNase I and 3 mg/mL Hyaluronidase (Sigma, St. Louis, Mo.) in DMEM (Corning Cellgro, Swedesboro, N.J.). The isolated cells were cultured in DMEM supplemented with 10% FCS, Penicillin/Streptomycin (100 IU/mL), Fungizone (0.5 μg/mL). Primary intestinal fibroblasts were used at passage 2. Cells were acquired on a LSR II flow-cytometer (BD Biosciences, San Jose, Calif.) and analyzed using FlowJo analysis software.

Example 6

Ex Vivo Intestinal Fibroblast Proliferation and Apoptosis Assay

Primary intestinal fibroblasts were isolated and stained with CellTrace Violet (Invitrogen, Carlsbad, Calif.) per manufacturer's instructions. Stained cells were then incubated with 100 ng/mL of Tl1a in DMEM supplemented with 10% FCS, Penicillin/Streptomycin (100 IU/mL), and Fungizone (0.5 μg/mL). After 48 hours, cultured intestinal fibroblasts were stained using Annexin V Apoptosis Detection Kit (eBioscience, San Diego, Calif.) per manufacturer's instructions. After Annexin V stain, fibroblasts were harvested, washed and fixed with 2% paraformaldehyde and subjected to flow cytometric analysis with BD LSR II flow-cytometer and analyzed by FlowJo software.

Example 7

Statistical Analysis

Data are presented as the mean±standard deviation (SD). Comparison between two groups was performed by a two-tailed Fisher's Exact Test for categorical variables and Student's t-test for continuous variables. Parametric and non-parametric tests were used depending on the fulfillment of the test assumptions. Comparison between three groups was done using ANOVA, followed by pair wise post-hoc analysis with Turkey's HSD and Behrens-fisher-Test correction for the multiple comparisons. $p<0.05$ was considered significant.

Example 8

Tl1a Ab Administration Attenuated Disease Activity and Gross Inflammation of Established Chronic Colitis The effect of neutralizing Tl1a function in chronic murine colitis was evaluated using Tl1a Ab in immune-deficient Rag1−/− mice that were adoptively transferred with nave CD4+CD45RBhi T-cells. Tl1a Ab at 20-, and 80-mg/kg or isotype control Ab (Iso Ab) at 80-mg/kg was administered two times per week beginning on day 29 posttransfer when colitis was established (FIG. 1A). By week 6 and continuing through the end of the study at week 8, the disease activity index (DAI) of mice treated with Tl1a Ab was significantly lower than mice receiving the Iso Ab (FIG. 1B). Compared to the Iso Ab group, gross colonic inflammation was significantly reduced in mice that received Tl1a Ab at both doses (FIG. 1C). The number of mononuclear cells recovered from mesenteric lymph nodes (MLN) and the lamina propria (LP) was also reduced with Tl1a Ab treatment as compared to the iso Ab group (FIG. 1D). In the Tl1a 80-mg/kg Ab treated mice, amelioration of established colitis and cellular infiltrates was demonstrated by less severe gross colonic inflammation and significantly reduced numbers of LP mononuclear cells (LPMC) than the Pre-Tx group (FIGS. 1C and D).

Figure 7:
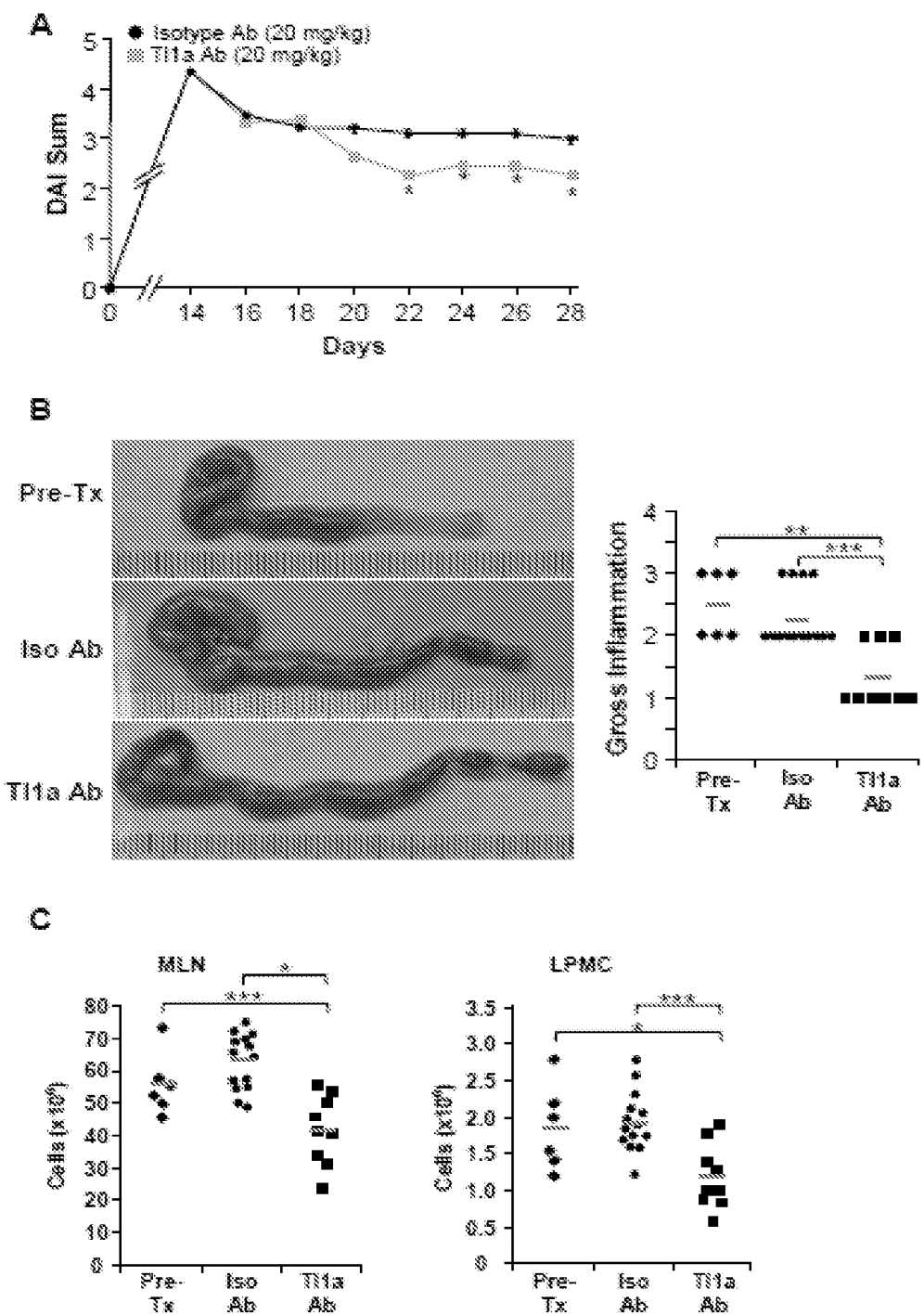
FIG. 7 depicts, in accordance with an embodiment herein, Tl1a Ab reduced inflammatory disease activity due to chronic DSS administration. (A) DAI is compared between isotype Ab (n=14) and Tl1a Ab (n=9) treated groups. (B) Representative gross appearance of colon (left panels) with the quantative inflammatory score (right panel) are shown. Data are expressed as mean+/−SD. (C) Total numbers of mononuclear cells were isolated from MLN and LP. Each filled symbol represents an independent mouse. Tl1a Ab treated groups are compared to Pre-Tx and Iso Ab group. *P<0.05, P<0.01, *P<0.001.

Similar findings were obtained using the chronic DSS colitis model. In this model, Tl1a Ab (20-mg/kg) was administered twice a week beginning at day 15 when colitis was established (FIG. 1A). Compared to the Iso Ab group, we observed lower DAI (FIG. 7A), reduced gross inflammation (FIG. 7B), and fewer recovered mononuclear cells from MLN and LP (FIG. 7C). The reduction of DAI and mononuclear cells was also less than the Pre-Tx group. These data showed that treatment with Tl1a Ab resulted in decreased gross indicators of inflammation and reduced accumulation of inflammatory cells in the intestine.

Example 9

Figure 2:
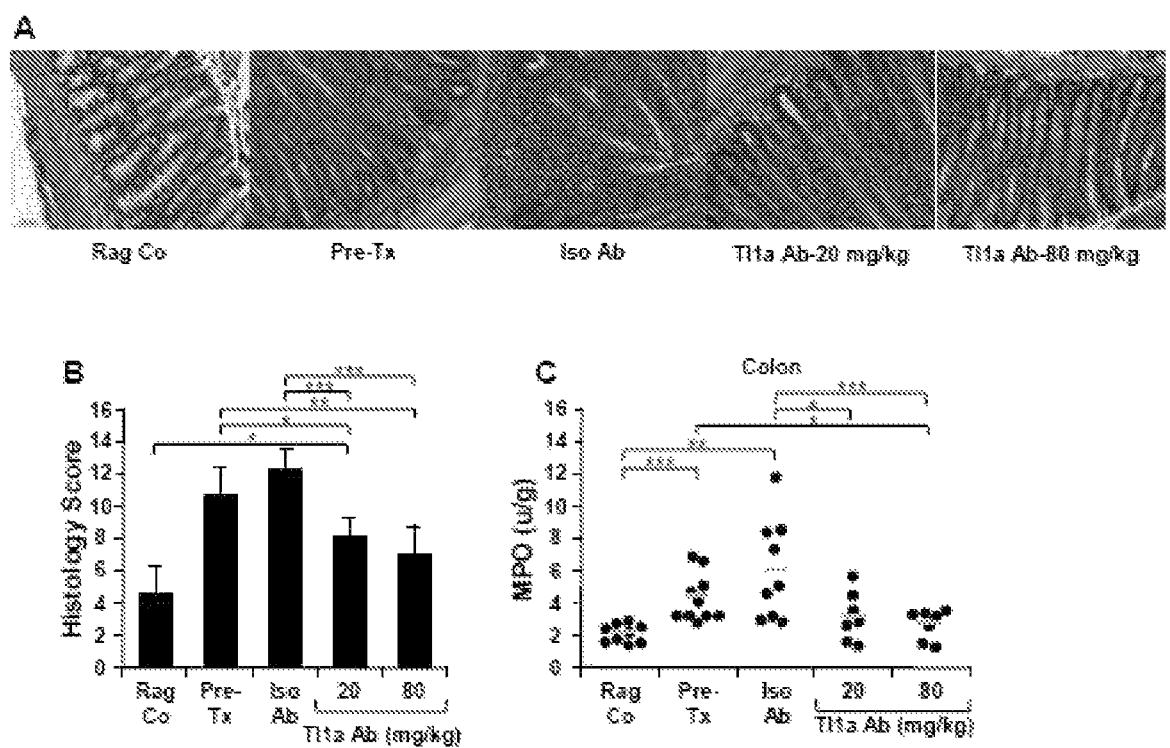
FIG. 2 depicts, in accordance with an embodiment herein, Tl1a Ab treatment reversed established colonic inflammation. (A) Representative H&E stained mid-colon sections at 200× magnification. (B) Quantitative histology scores for the adoptive transfer model. At least 20 independent fields are scored and data are expressed as mean±SD. (C) Myeloperoxidase activity was measured and represented as unite of activity (u) per gram (g) of colonic protein extract. Each filled circle represents an independent mouse. Tl1a Ab treated groups are compared to baseline Rag Co, Pre-Tx, and Iso Ab experimental groups. $*p<0.05$, $p<0.01$, $*p<0.001$.

Tl1a Ab Administration Mitigated Histopathologic Features of Established Murine Colitis Histologic examination of the colon revealed reduced inflammation characterized by reduced cellular infiltrate, mucin depletion, crypt abscess, and architectural changes with Tl1a Ab therapy compared to Iso Ab group in the adoptive transfer model (FIGS. 2A and B). The reduction in histological inflammation was also significantly reduced compared to the 4 week Pre-Tx group (FIGS. 2A and B), indicating partially resolved inflammation. Consistently, colonic myeloperoxidase (MPO) activity was significantly reduced with both doses of Tl1a Ab administration as compared to the Iso Ab group and with 80-mg/kg of Tl1a Ab as compared to the Pre-Tx group (FIG. 2C). Mucosal resolution of colitis was suggested when the reduction in colonic MPO activity with Tl1a Ab dose reached a level not significantly different than the Rag baseline control (Rag Co) group (FIG. 2C).

Figure 8:
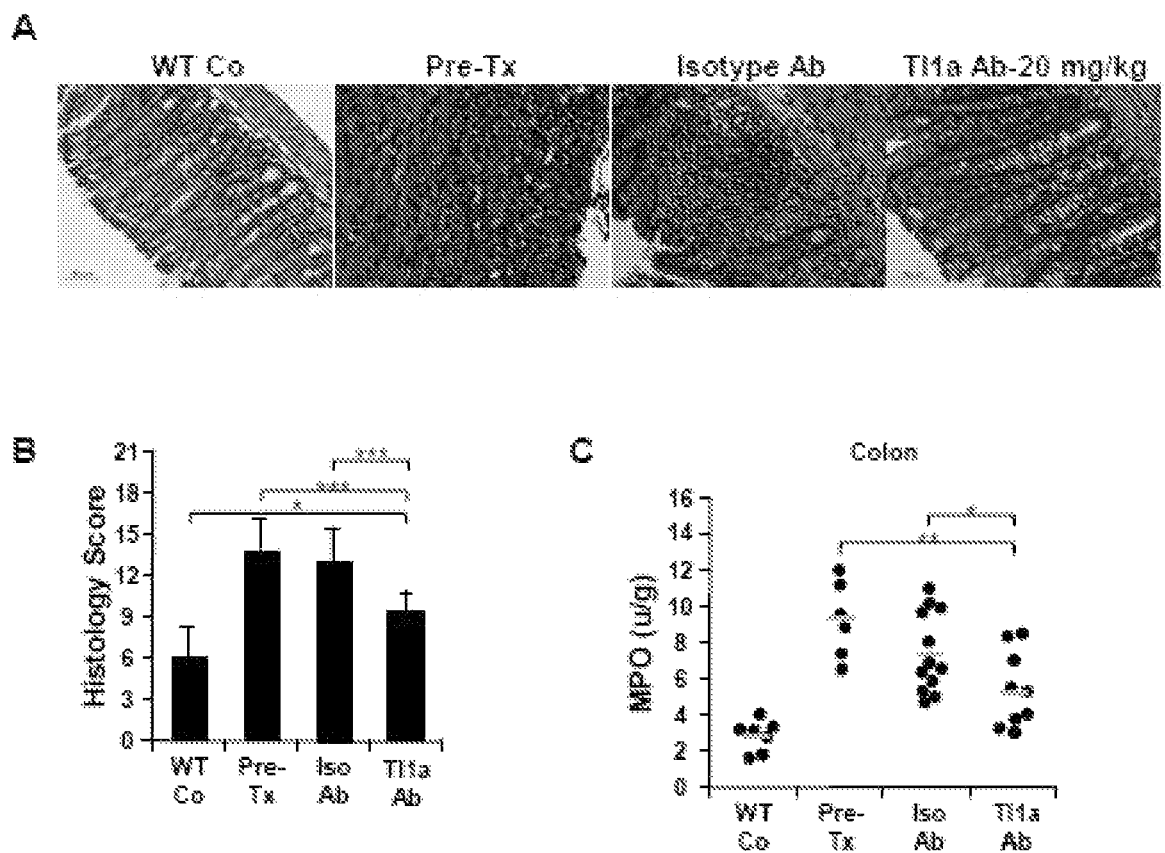
FIG. 8 depicts, in accordance with an embodiment herein, Tl1a Ab reversed established colonic inflammation in the chronic DSS model. (A) Representative H&E stained mid-colon sections at 200× magnification are shown. (B) Quantitation of histologic inflammation from at least 20 independent mid-colon fields are scored and data are expressed as mean+/−SD. (C) Myeloperoxidase activity was measured and represented as unit of activity (u) per gram (g) of colonic protein extract. Tl1a Ab treated groups are compared to baseline WT Co, Pre-Tx, and Iso Ab experimental groups. Each filled circle represent MPO activity from an independent colon. *P<0.05, P<0.01, *P<0.001.

Similarly, there was improved colon histopathology with Tl1a Ab as compared to both the Iso Ab and Pre-Tx group in the chronic DSS model (FIGS. 8A and B). Although there were reduction in histologic inflammation with Tl1a Ab treatment, colonic inflammation is still significantly higher as compared to baseline WT Co group (FIG. 8B). In addition, colonic MPO activity was significantly lower with Tl1a Ab treatment as compared to both the Iso Ab and the Pre-Tx group (FIG. 8C). These results showed that administration of Tl1a Ab resulted in normalization of colonic histopathology.

Example 10

Tl1a Ab Inhibited Th-1 and -17 Immune Responses

Figure 3:
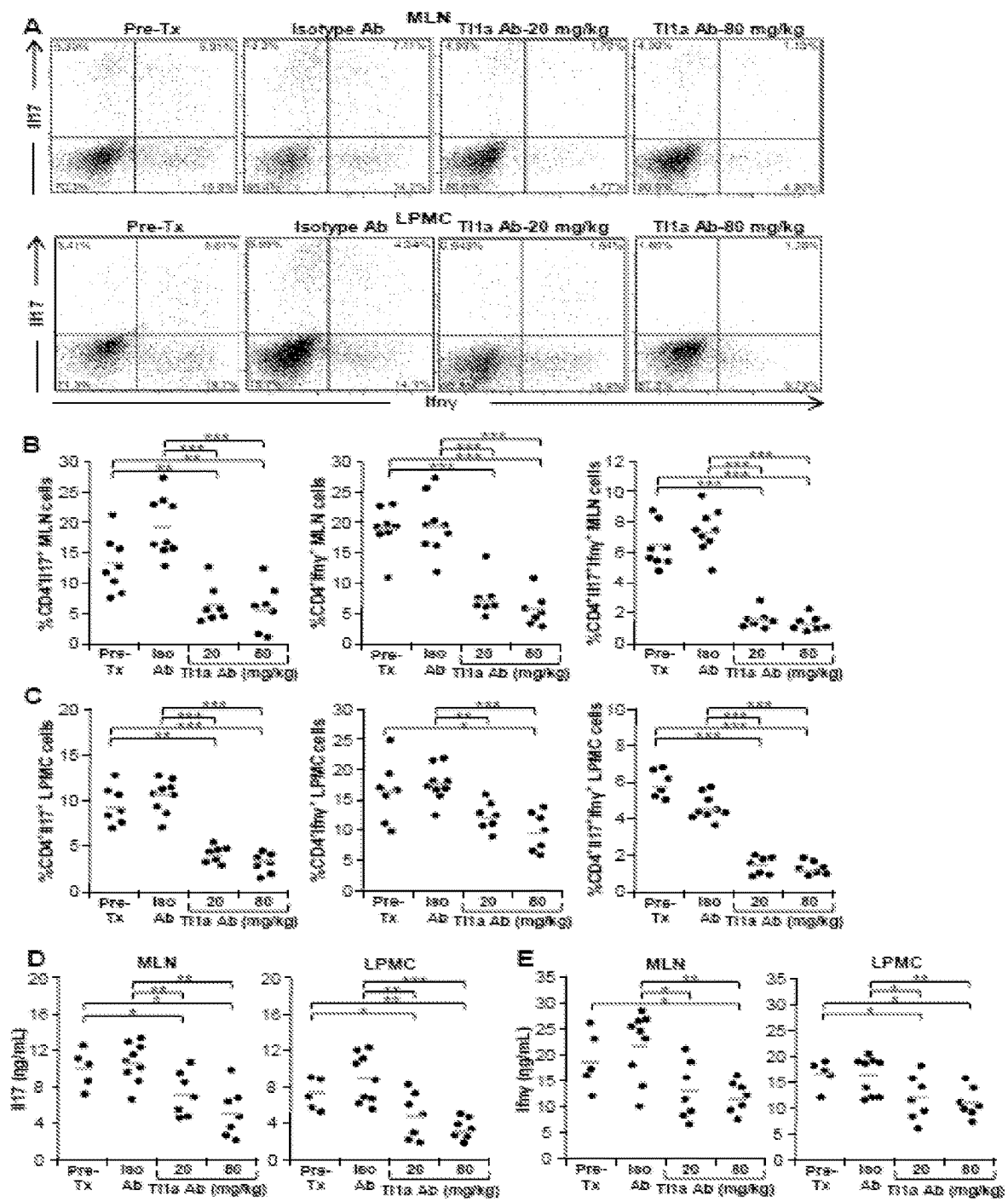
FIG. 3 depicts, in accordance with an embodiment herein, Tl1a Ab reduced Th-1 and -17 immune responses. (A) Representative flow cytometry plots of gated CD4+ cells that were stained for intracellular Ifnγ and Il17 expression are shown for MLN (top panels) and LPMC (bottom panels). The percentages of CD4+Il17+, CD4+Ifnγ+, and CD4+Il17+Ifnγ+ T-cells were quantitated for MLN (B) and LPMC (C). Isolated mononuclear cells from MLN and LPMC were stimulated with anti-CD3 and anti-CD28 and the levels of secreted Il17 (D) and Ifnγ (E) were assessed by ELISA. Each filled circle represents value obtained from an independent mouse. Tl1a Ab treated groups are compared to Pre-Tx and Iso Ab experimental groups. $*p<0.05$, $p<0.01$, $*p<0.001$.
Figure 9:
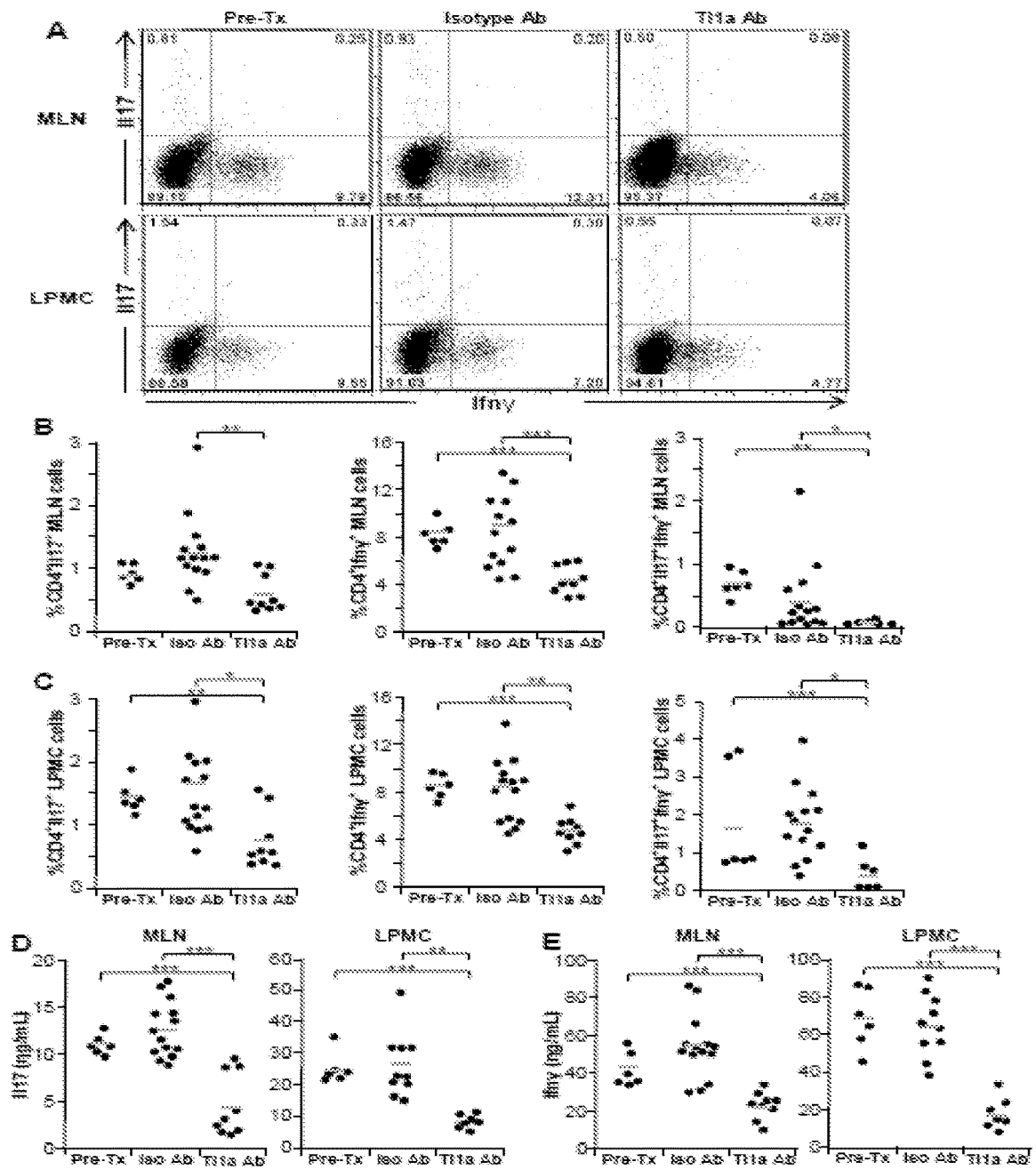
FIG. 9 depicts, in accordance with an embodiment herein, Tl1a Ab reduced Th-1 and -17 immune responses in the chronic DSS colitis model. (A) Representative flow cytometry plots of gated CD4+ cells from (top panels) and LPMC (bottom panels) that were stained for intracellular Ifnγ and Il-17. The percentages of CD4+Il17+, CD4+Ifnγ+, and CD4+Il17+Ifnγ+ T-cells were quantitated for MLN (B) and LPMC (C). Isolated mononuclear cells from MLN and LPMC were stimulated with anti-CD3ε and anti-CD28 and the levels of secreted Il17 (D) and Ifnγ (E) were assessed by ELISA. Each filled circle represents value obtained from an independent mouse. *p<0.05, p<0.01, *p<0.001.

To assess the potential immune mechanisms of reduced established murine colitis in the two colitogenic models, the expression of Ifnγ, Il13, and Il17 was measured. Tl1a Ab reduced the frequency of CD4+Il17+ T-cells in MLN and LPMC compared to both the Iso Ab group and Pre-Tx group in the adoptive transfer model (FIGS. 3A and B). CD4+Ifnγ+ T-cells were similarly reduced with both doses of Tl1a Ab treatment except in LPMC where Tl1a Ab at 20-mg/kg did not result in a significant reduction as compared to the Pre-Tx group (FIGS. 3A and C). Additionally, the inventors also found significantly reduced Ifnγ+ and Il17+ double positive CD4+ T-cells with Tl1a Ab treatment as compared to Pre-Tx and Iso Ab groups in both MLN and LPMC (FIGS. 3B and C, right panel). Using MLN and LPMC cells that were stimulated with CD3/CD28, lower Il17 production was seen in mice treated with Tl1a Ab as compared to mice that received Iso Ab and the pre-treatment group (FIG. 3D). Except in the MLN, Tl1a Ab treatment at both doses led to lower Ifnγ secretion as compared to Iso Ab and the Pre-Tx group (FIG. 3E). The percentage of CD4+Il13+ T-cells and Il13 production was not significantly different among the groups. In the chronic DSS colitis model, reduction of CD4+Il17+, CD4+Ifnγ+ and CD4+Il17+Ifnγ+ T-cells was similarly observed in MLN and LPMC with Tl1a Ab treatment (FIG. 9A-C). Consistently, Tl1a Ab treatment resulted in lower production of Il17 and Ifnγ in isolated MLN and LPMC cells that were stimulated with CD3/CD28 (FIGS. 9D and E). The percentages of CD4+Il13+ T-cells and Il13 production were not different among the groups in the chronic DSS colitis model. These data suggested that Tl1a Ab reduced Th-1 and -17 proinflammatory immune responses.

Example 11

Tl1a Ab Reversed Established Colonic Fibrosis

Figure 4:
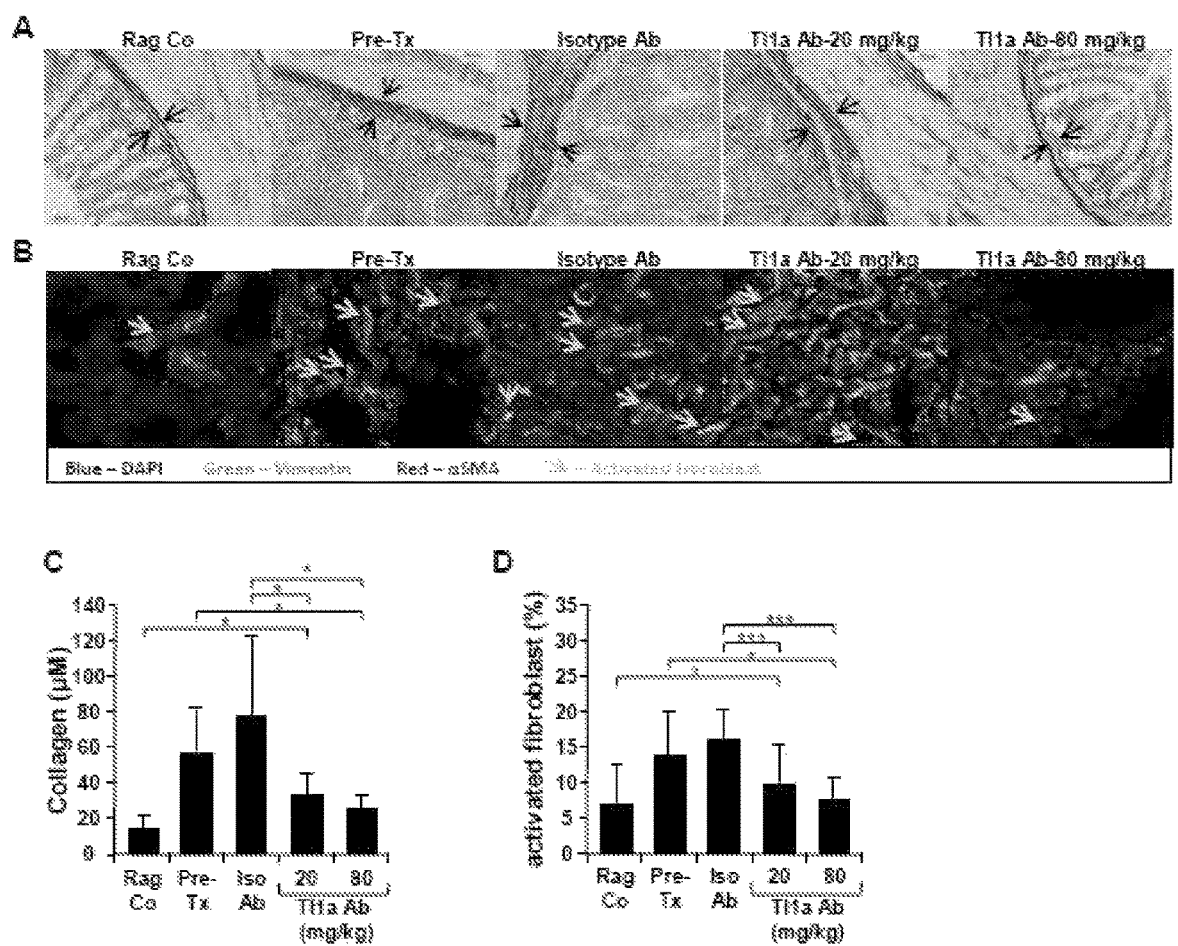
FIG. 4 depicts, in accordance with an embodiment herein, reversal of established fibrosis with Tl1a Ab therapy in the adoptive transfer model. (A) Representative Sirius red staining of collagen deposition in mid-colon tissue sections at 200× magnification. Black arrows denote thickness of collagen deposition. (B) Representative immunofluorescent staining of vimentin (green) and αSMA (red) from mid-colon sections are shown. Orange arrows denote myofibroblast that coexpresses vimentin and αSMA. Quantitation of the collagen thickness (C) and percentages of activated fibroblasts (D) from the mid-colon sections are shown and expressed as mean±SD. At least 20 independent fields were scored per group. Tl1a Ab treated groups are compared to baseline Rag Co, Pre-Tx, and Iso Ab experimental groups. $*p<0.05$, $p<0.01$, $*p<0.001$.

Mice with constitutive Tl1a expression were previously shown to develop increased gut fibrosis. To assess whether blocking Tl1a signaling can reduce colonic fibrosis, we performed Sirius red stain to measure the degree of collagen deposition. The inventors found increased collagen deposition by the 4th week after naïve T cell transfer in the Pre-Tx group compared to baseline Rag Co group (FIGS. 4A and C). The degree of collagen deposition became greater by the 8th week in mice receiving control Iso Ab. However, treatment with Tl1a Ab led to significant reduction in collagen deposition when compared to mice that received the Iso Ab or the Pre-Tx group (FIGS. 4A and C). Notably, collagen deposition was not significantly different when 80 mg/kg of Tl1a treatment was compared to normal Rag Co mice (FIG. 4C). In the chronic DSS model, similar reduction in collagen deposition with Tl1a Ab treatment as compared to Iso Ab or the Pre-Tx group was observed (FIGS. 4A and C). In addition, Tl1a treatment led to a reduction in collagen deposition to a level that was not statistically different than WT baseline control (FIGS. 4A and C). Together, these data suggested that blocking Tl1a signaling reversed collagen deposition to similar levels prior to the onset of inflammation.

Example 12

Blocking Tl1a-Dr3 Signaling Reduced Intestinal Fibroblast and Myofibroblast Number To begin to study the mechanism of collagen deposition reduction with Tl1a Ab, the frequency of intestinal fibroblasts and myofibroblasts was measured. Intestinal myofibroblasts are a cell population involved in gut fibrogenesis. Vimentin positive cells are fibroblasts, which in the context of co-expression of alpha smooth muscle actin (αSMA), represent myofibroblasts. The data showed that 4 weeks after naïve T-cell transfer (Pre-Tx group), the number of fibroblasts and myofibroblasts increased (FIGS. 4B and D). The number of fibroblasts and myofibroblasts further increased by 8th week in mice receiving Iso Ab. However, treatment with Tl1a Ab led to a reduction in the number of fibroblasts and myofibroblasts to levels similar to normal Rag Co (FIGS. 4B and D). Interestingly, the reduction in myofibroblasts in the mice that received 80-mg/kg of Tl1a Ab reached a level that was not statistically different than Rag Co mice (FIGS. 4B and D), suggesting reversal of fibrogenesis.

Figure 10:
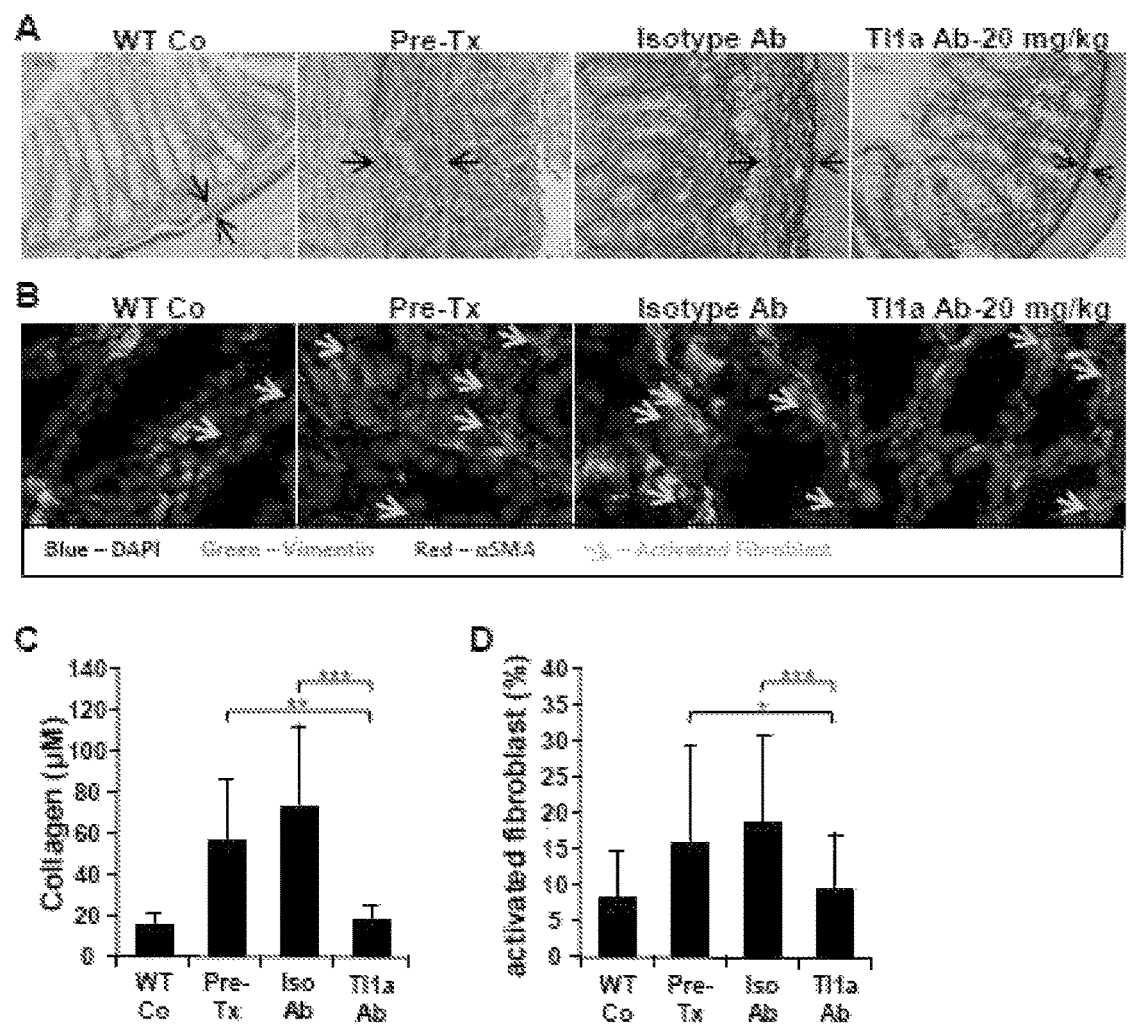
FIG. 10 depicts, in accordance with an embodiment herein, reversal of established fibrosis with Tl1a Ab in the chronic DSS colitis model. (A) Representative Sirius red staining of collagen deposition in mid-colon tissue sections at 200× magnification are shown. Black arrows denote thickness of collagen deposition. (B) Representative immunofluorescent staining of vimentin (green) and αSMA (red) from mid-colon sections are shown. Orange arrows denote myofibroblast that co-expresses vimentin and αSMA. Quantitation of the collagen thickness (C) and percentages of activated fibroblasts (D) from the mid-colon sections are shown and expressed as mean±SD. At least 20 independent fields were scored per group. *p<0.05, p<0.01, *p<0.001.

In the chronic DSS model, similar reduction in the number of fibroblasts and myofibroblasts with Ab treatment when compared to isotype or the Pre-Tx group was observed (Supplementary FIGS. 4B and D). Consistent with the adoptive transfer model, the reduction in the number of gut fibroblasts and myofibroblasts with Tl1a Ab treatment reached a level that was not statistically different from WT baseline control (FIGS. 10B and D).

The inventors generated Dr3 deficient (Dr3−/−) mice (FIGS. 5A and B) to delineate whether the reduction in the number of intestinal fibroblasts and myofibroblasts is due to direct Tl1a-Dr3 signaling. There were significantly fewer intestinal fibroblasts in Dr3−/− as compared to wildtype littermate baseline (non-colitic) mice (FIG. 5C). Next, the inventors performed ex vivo CellTrace Violet assay and Annexin V stain to determine whether the difference in intestinal fibroblasts between WT and Dr3−/− mice is due to proliferation and/or apoptosis, respectively. Flow cytometric analysis showed similar rates of proliferation as evident by the overlapping CellTrace Violet intensity between WT and Dr3−/− intestinal fibroblasts (FIG. 5D, top panel). No differences were observed in the rate of apoptosis between wildtype and Dr3−/− intestinal fibroblasts (FIG. 5D, bottom panel).

Example 13

Reversal of Fibrogenesis with Tl1a Ab Therapy

To study the molecular mechanisms of reversal of established intestinal fibrosis with Tl1a Ab, the expression of collagen, fibrogenic program mediators (Tgfβ1, Ctgf, Igf1, Pten, and Il31Ra), and factors (Mmp and Timp) involved in extracellular matrix (ECM) remodeling were measured. Lower levels of collagen expression were found in both the adoptive transfer and chronic DSS models (Table 1 and Table 2 herein). Normalization in the fibrogenic program with Tl1a Ab was observed with lower expression of pro-fibrotic mediators including Tgfβ31 and Il31Ra in both the adoptive transfer and chronic DSS models and Igf1 in the adoptive transfer model (Table 1 and Table 2). The expression of connective tissue growth factor (Ctgf), a downstream mediator of Tgfβ signaling, was reduced with Tl1a Ab administration as compared to Pre-Tx and Iso Ab groups in the adoptive transfer model. ECM remodeling was assessed by measuring the expression of metalloproteases (Mmp) and tissue inhibitors of metalloproteases (Timp). Compared to the isotype Ab group, the expression of genes involved in ECM degradation was reduced in mice treated with Tl1a Ab in the adoptive transfer model (Mmp2, Mmp3; Table 1) and in the chronic DSS model (Mmp2, Mmp3, Mmp13; Table 2). Notably, the expression of Timp was lower with Tl1a treatment in the adoptive transfer model (Timp2, Table 1) and in the chronic DSS model (Timp1, Timp2; Table 2). These results demonstrate that there is a reduction in the fibrogenic program with Tl1a Ab, which leads to decreased collagen synthesis. The lower expression of both Mmp and Timp may contribute to the enhanced removal of established ECM components rather than inducing tissue damage. Thus, the data suggest that reversal of established fibrosis by Tl1a Ab might be the net result of the reduced fibrogenic program and possibly the reduction of both Mmp and Timp.

Example 14

Intestinal Fibroblasts Express Dr3 and Respond to Tl1a Stimulation

Figure 6:
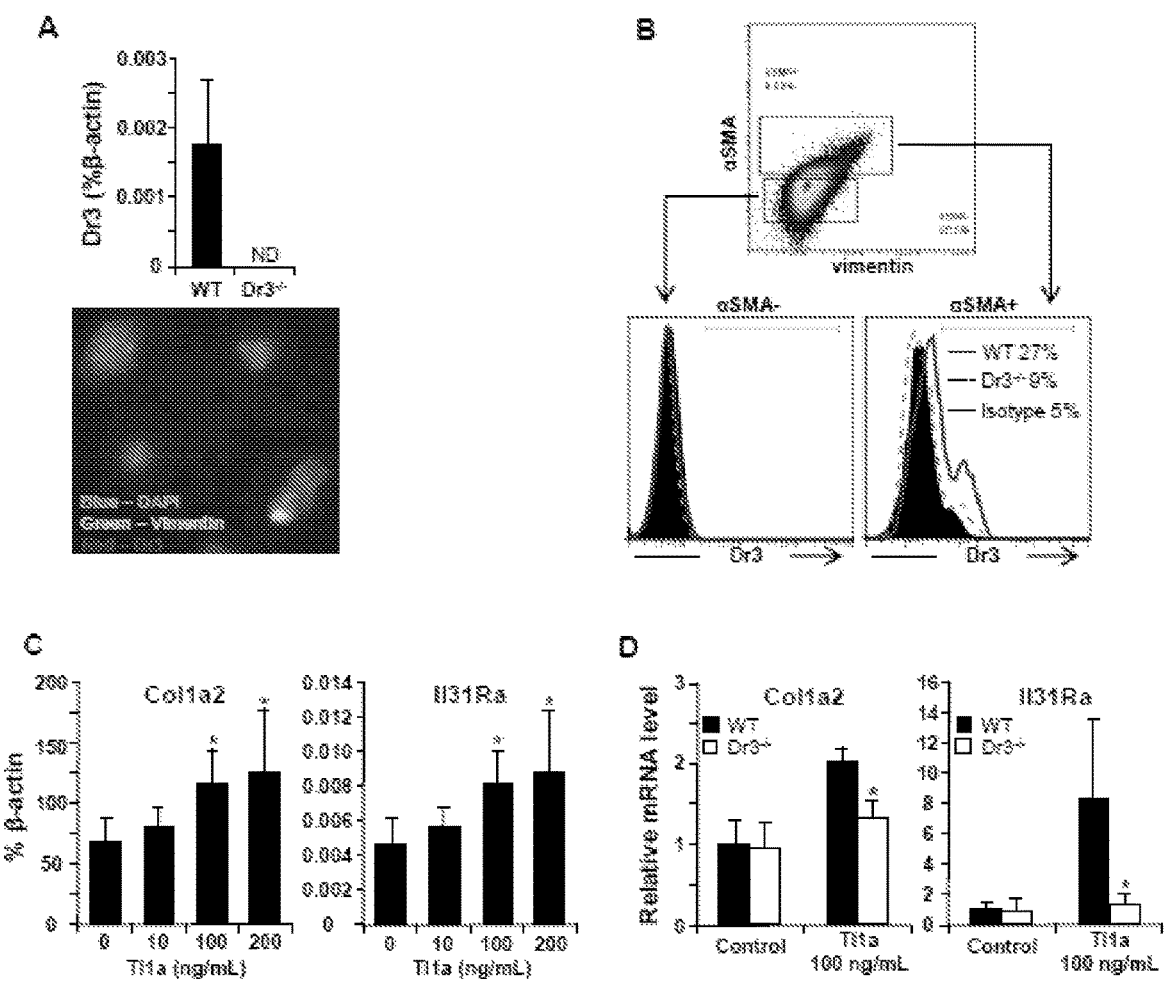
FIG. 6 depicts, in accordance with an embodiment herein, intestinal fibroblasts express Dr3 and responds to Tl1a stimulation. (A) Dr3 mRNA is detected in WT but not Dr3−/− fibroblasts (top). ND=not detected. Immunofluorescent staining of WT fibroblasts showed positive Dr3 staining in red (bottom). (B) Primary intestinal fibroblasts were stained with Dr3, αSMA and vimentin. αSMA positive and negative fibroblasts were gated as shown and Dr3 staining is found in αSMA+WT but not Dr3−/− and αSMA negative cells. Data shown are representative of at least 3 independent experiments with similar results. (C) Expression of Col1a2 and Il31Ra mRNA in WT primary intestinal fibroblasts with increasing Tl1a stimulation (0-200 ng/mL) and represented as mean±SD. (D) Relative induction of Col1a2 and Il31Ra mRNA by Tl1a in WT and Dr3−/− intestinal and represented as mean±SD. *p<0.05.

The inventors investigated whether intestinal fibroblasts can functionally respond to direct Tl1a signaling. mRNA levels of Dr3, the only known receptor for Tl1a, were measured and found to be expressed at low levels in WT but not in Dr3 deficient primary intestinal fibroblasts (FIG. 6A, top panel). Consistently, immunofluorescent staining showed that Dr3 is expressed on WT primary intestinal fibroblasts (FIG. 6A, bottom panel). Using flow cytometry, the inventors found that Dr3 is expressed preferentially on fibroblasts that co-express αSMA as compared to fibroblasts without αSMA expression (FIG. 6B). The inventors next checked whether intestinal fibroblasts can respond to Tl1a stimulation and used collagen (Col1a2) and Il31 receptor (Il31Ra) as markers of fibroblast activation. The inventors showed that Tl1a can dose dependently increase the expression of Col1a2 and Il31Ra in murine primary intestinal fibroblasts ex vivo (FIG. 6C). The specificity of Tl1a stimulation is demonstrated by the blunted Tl1a induction of Col1a2 and Il31Ra in Dr3−/− murine intestinal fibroblasts ex vivo (FIG. 6D). These data indicate that intestinal fibroblasts express Dr3 and can functionally respond to direct Tl1a signaling.

Example 15

Results for Expression Analysis of Fibrosis Mediators

TABLE 1

Expression analysis of fibrosis mediators in the adoptive transfer colitis model.

| | baseline | Pre-Tx | Iso Ab | Tl1a Ab - 80 mg/kg | | | |
|---|---|---|---|---|---|---|---|
| | % β-actin | % β-actin | % β-actin | % β-Actin | | p vs. | |
| | n = 6 | n = 6 | n = 7 | n = 6 | Rag | Pre-Tx | Iso Ab |
| col1a1 | 0.19 ± 0.12 | 0.19 ± 0.12 | 0.21 ± 0.10 | 0.11 ± 0.03 | ns | 0.024 | 0.03 |
| col1a2 | 0.49 ± 0.29 | 0.76 ± 0.32 | 1.23 ± 0.78 | 0.39 ± 0.12 | ns | 0.024 | 0.026 |
| col3a1 | 12.69 ± 3.61 | 16.45 ± 3.93 | 16.08 ± 4.04 | 9.66 ± 3.44 | ns | 0.0073 | 0.014 |
| col4a1 | 1.54 ± 0.32 | 1.95 ± 0.32 | 1.88 ± 0.84 | 1.19 ± 0.33 | ns | 0.00055 | ns |
| Tgfβ1 | 0.16 ± 0.06 | 0.40 ± 0.16 | 0.50 ± 0.17 | 0.25 ± 0.06 | 0.018 | 0.046 | 0.003 |
| Ctgf | 0.66 ± 0.13 | 1.04 ± 0.40 | 1.04 ± 0.32 | 0.54 ± 0.08 | ns | 0.021 | 0.007 |
| Igf1 | 0.32 ± 0.06 | 0.53 ± 0.18 | 0.73 ± 0.36 | 0.41 ± 0.15 | ns | ns | 0.047 |
| Pten | 3.80 ± 0.75 | 2.28 ± 0.53 | 1.86 ± 0.25 | 2.03 ± 0.67 | 0.0015 | ns | ns |
| Il31Ra | 0.003 ± 0.001 | 0.005 ± 0.002 | 0.007 ± 0.003 | 0.004 ± 0.001 | ns | ns | 0.034 |
| Mmp2 | 0.32 ± 0.072 | 0.43 ± 0.12 | 0.44 ± 0.13 | 0.28 ± 0.07 | ns | 0.015 | 0.015 |
| Mmp3 | 0.046 ± 0.022 | 1.15 ± 1.15 | 1.18 ± 0.70 | 0.34 ± 0.37 | 0.043 | ns | 0.036 |
| Mmp13 | 0.047 ± 0.015 | 0.20 ± 0.17 | 0.18 ± 0.08 | 0.10 ± 0.06 | ns | ns | ns |
| Timp1 | 0.038 ± 0.014 | 0.19 ± 0.24 | 0.18 ± 0.12 | 0.14 ± 0.07 | 0.016 | ns | ns |
| Timp2 | 1.11 ± 0.27 | 0.86 ± 0.15 | 0.79 ± 0.12 | 0.59 ± 0.18 | 0.001 | 0.001 | 0.048 | ns = not significant

TABLE 2

Expression analysis of fibrosis mediators in the DSS model.

| | WT | Pre-Tx Co | Isotype Co | Tl1a Ab - 20 mg/kg | | | |
|---|---|---|---|---|---|---|---|
| | % β-actin | % β-actin | % β-actin | % β-actin | | p vs. | |
| | n = 6 | n = 5 | n = 5 | n = 5 | WT | Pre-Tx | Isotype |
| col1a1 | 0.54 ± 0.45 | 0.55 ± 0.36 | 0.67 ± 0.45 | 0.30 ± 0.17 | ns | ns | ns |
| col1a2 | 0.67 ± 0.26 | 1.20 ± 0.94 | 1.19 ± 0.93 | 0.63 ± 0.31 | ns | ns | ns |
| col3a1 | 35.79 ± 10.95 | 38.64 ± 18.02 | 35.18 ± 9.74 | 23.28 ± 3.47 | 0.044 | ns | 0.036 |
| col4a1 | 2.60 ± 1.08 | 2.62 ± 1.37 | 2.70 ± 0.54 | 1.83 ± 0.10 | ns | ns | 0.010 |
| Tgfβ1 | 0.21 ± .06 | 0.38 ± 0.15 | 0.43 ± 0.03 | 0.22 ± 0.04 | ns | 0.041 | 6.943E−05 |
| Ctgf | 0.97 ± .27 | 1.1 ± .32 | 1.14 ± .36 | 0.84 ± .21 | ns | ns | ns |
| Igf1 | 0.48 ± 0.18 | 0.85 ± 0.63 | 1.09 ± 0.52 | 0.65 ± 0.28 | ns | ns | ns |
| Pten | 0.004 ± 0.003 | 0.008 ± 0.004 | 0.012 ± 0.003 | 0.008 ± 0.002 | ns | ns | ns |
| Il31Ra | 3.13 ± 0.65 | 2.56 ± 0.61 | 2.67 ± 0.97 | 2.69 ± 0.31 | 0.020 | ns | 0.046 |
| Mmp2 | 0.52 ± 016 | 0.60 ± 0.29 | 1.21 ± 0.38 | 0.52 ± 0.25 | ns | ns | 0.007 |
| Mmp3 | 0.03 ± 0.015 | 2.07 ± 3.70 | 1.91 ± 0.10 | 0.42 ± 0.27 | 0.003 | ns | 1.48E−05 |
| Mmp13 | 0.05 ± 0.011 | 0.61 ± 1.07 | 1.02 ± 0.21 | 0.21 ± 0.15 | 0.014 | ns | 0.0003 |
| Timp1 | 0.04 ± 0.024 | 0.32 ± 0.37 | 0.33 ± 0.06 | 0.15 ± 0.07 | 0.003 | ns | 0.004 |
| Timp2 | 1.02 ± 0.32 | 0.88 ± 0.17 | 1.12 ± 0.11 | 0.74 ± 0.14 | ns | ns | 0.005 | ns = not significant

Example 16

Figure 11:
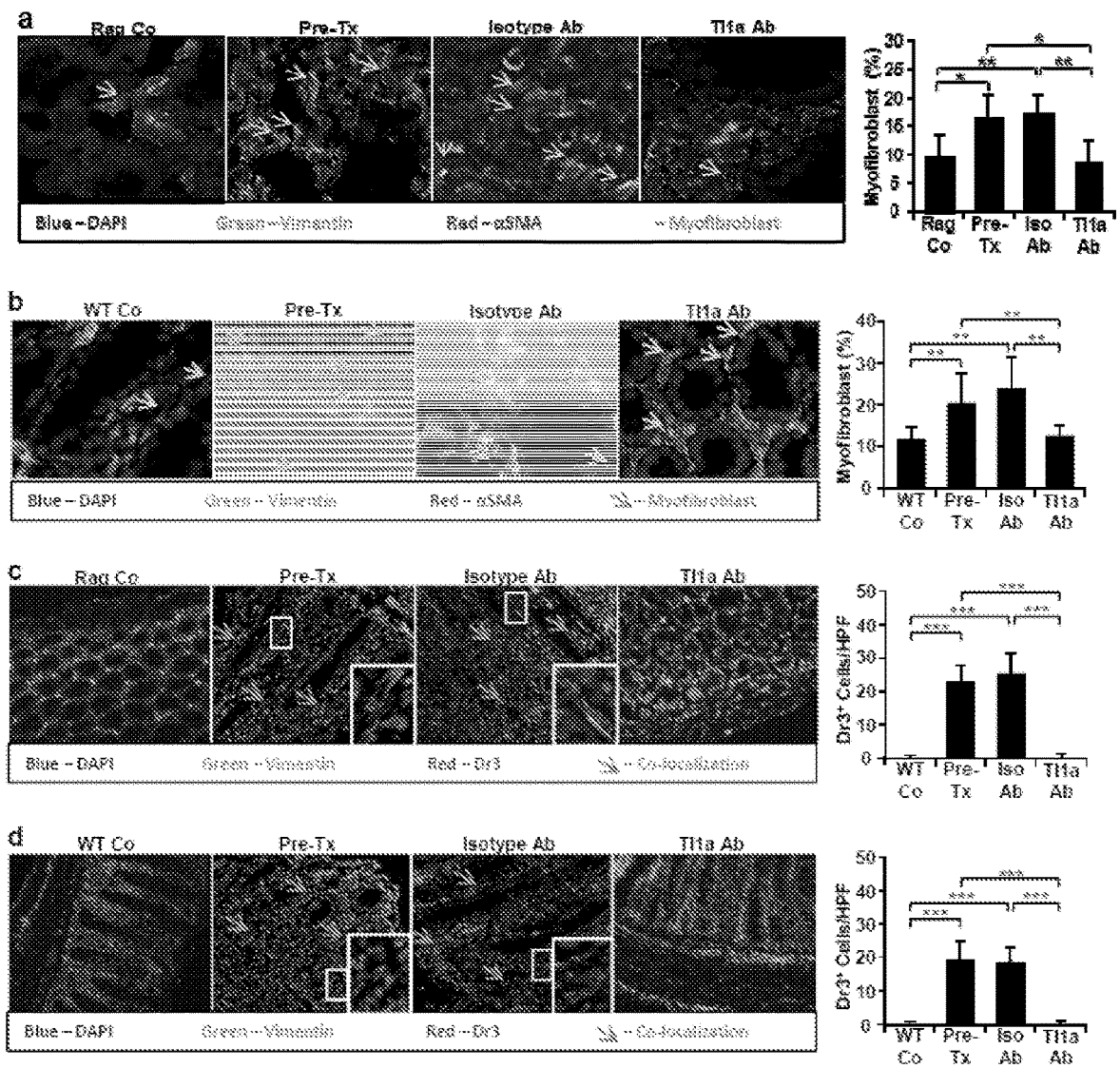
FIG. 11 depicts, in accordance with an embodiment herein, Tl1a Ab reduced myofibroblast number and expression of Dr3 and Tl1a. Representative immunofluorescent staining of vimentin (green) and αSMA (red) from mid-colon sections from the adoptive transfer model (a) and chronic DSS model (b) at 630× magnification are shown. Orange arrows denote myofibroblasts that co-express vimentin and αSMA. Percentages of myofibroblasts from the mid-colon sections were quantitated and expressed as mean+SD for the adoptive transfer model (a, right panel) and chronic DSS model (b, right panel). At least 10 independent fields were scored per group for (a) and (b). Representative immunofluorescent staining of vimentin (green) and Dr3 (red) from mid-colon sections are shown from the adoptive transfer model (c) and chronic DSS model (d). Figure insets for (c) and (d) are larger view of the images that were acquired at 200× magnification. At least 8 independent fields were quantitated per group and plotted as Dr3+ cells per high power fields (HPF). Colonic Dr3 (e) and Tl1a (f) mRNA was quantitated and shown as mean+SD (n=5-14). Tl1a Ab treated groups are compared to baseline Rag Co, Wt Co, Pre-Tx, and Iso Ab experimental groups. *P<0.05, P<0.01, *P<0.001. Specifically, FIGS. 11 (c) and (d) show increased Dr3 staining on fibroblasts in the Pre-treatment and Isotype antibody group (both associated with higher collagen deposition) as compared to Tl1a Ab treatment group (associated with lower collagen deposition). Additionally, FIGS. 11(e) and (f) show by RT-PCR expression analysis that both Tl1a and Dr3 expression is downregulated in the Tl1a Ab group (associated with lower collagen deposition) as compared to isotype group (associated with higher collagen deposition).
Figure 11:
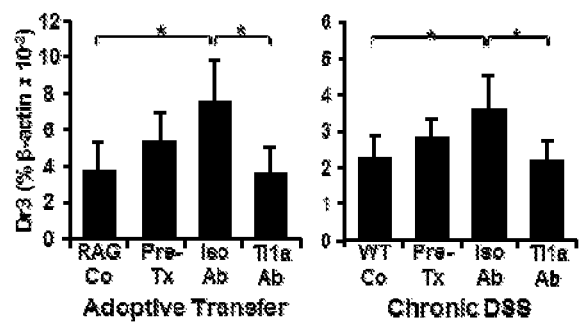
Figure 11:
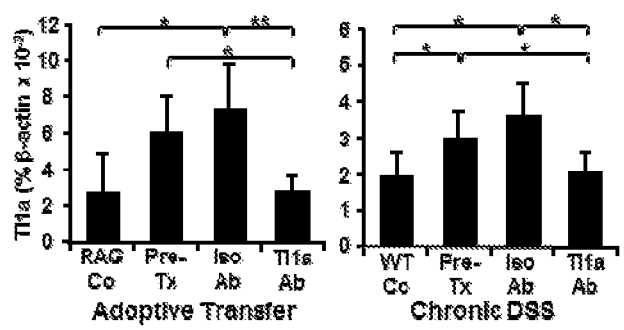

Blocking TL1A-Dr3 Signaling Reduced Numbers of Intestinal Fibroblasts and Myofibroblasts Additional Results Colonic myofibroblasts are a cell population involved in gut fibrogenesis. To study the cellular mechanisms of collagen deposition reduction with Tl1a Ab, fibroblast expression of vimentin and myofibroblast coexpression of vimentin and alpha smooth muscle actin (αSMA) were measured to assess the numbers of these cell types. After naïve T-cell transfer in both the Pre-Tx and Iso Ab groups, the numbers of colonic fibroblasts and myofibroblasts were increased (FIG. 11a). However, treatment with Tl1a Ab led to a reduction in the number of fibroblasts and myofibroblasts to levels similar to normal Rag Co (FIG. 11a).

In the chronic DSS model, mice treated with Tl1a Ab exhibited a similar reduction in the number of colonic fibroblasts and myofibroblasts compared to the Iso or the Pre-Tx groups (FIG. 11b). Consistent with what was observed in the adoptive transfer model, the number of gut fibroblasts and myofibroblasts with Tl1a Ab treatment reduced to a level that was not statistically different from WT baseline control (FIG. 11b). Because there was still significantly worsened colitis with Tl1a Ab treatment as compared to WT Co group in the chronic DSS colitis model, the reduced numbers of myofibroblasts and fibroblasts is consistent with at least in part, a direct consequence of neutralizing Tl1a, rather than solely a secondary effect through reduced inflammation.

It was next assessed whether there were Dr3 expression changes in association with fibrotic changes in these murine models of chronic colitis. Immunofluorescent staining revealed increased Dr3 expression in the Pre-Tx and Iso Ab groups as compared to both baseline control groups (Rag Co and WT Co) and the Tl1a Ab treated groups in both the adoptive transfer and chronic DSS colitis models (FIG. 11c, d). Notably, there was expression of Dr3 in a percentage of fibroblasts in the Pre-Tx and Isotype Ab groups (FIG. 11c, d). Real-time quantitative reverse transcriptase-PCR analysis showed that the expression of Dr3 was significantly higher in the Iso Ab group as compared to mice in the both baseline control (Rag Co and WT Co) and Tl1a Ab treatment groups in both models (FIG. 11e). Additionally, Tl1a mRNA expression was significantly increased in the Iso Ab group as compared to un-inflamed controls (Rag Co and WT Co) and the Tl1a Ab treatment groups in both the adoptive transfer and chronic DSS colitis models (FIG. 11f). These results are consistent with a direct relationship between Dr3-Tl1a expression and increase in intestinal fibrosis.

Figure 12:
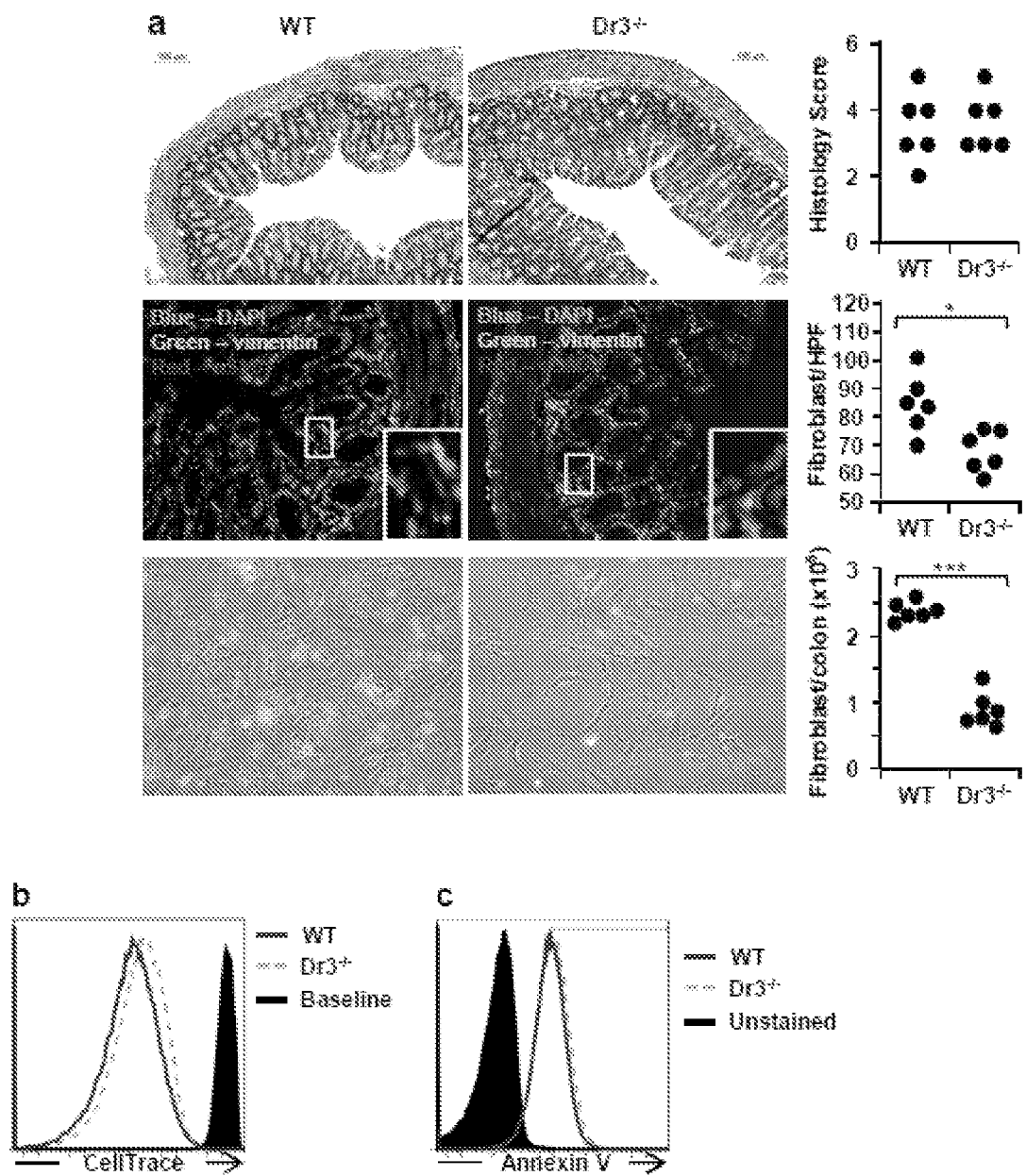
FIG. 12 depicts, in accordance with an embodiment herein, reduced intestinal fibroblasts with Dr3 deficiency. (a) Representative H&E stained colon at 100× magnification with quantitation of inflammation is shown on the upper panels. Representative Vimentin/αSMA stained colon at 200× magnification (insets are larger view at 200× magnification) with quantitation of fibroblasts per HPF is shown in the middle panels. Representative photographs of intestinal fibroblasts recovered from littermate WT and Dr3−/− colon and individual total fibroblasts per colon are shown (a, bottom panels). Representative flow cytometric histograms of proliferating fibroblasts (b) and fibroblasts undergoing apoptosis (c) from WT and Dr3−/− mice are shown. Decreased CellTrace violet fluorescence intensity indicates proliferation. Increased Annexin V staining indicates apoptosis. Representative flow cytometric histograms of at least 6 independent experiments with similar results are shown. *P<0.05, P<0.01, *P<0.001. Specifically, with regard to 12(a), top panel shows there is no difference in histologic inflammation between wildtype and Dr3KO colon to illustrate that it is not the underlying inflammation that is causing the reduced fibroblast number in Dr3KO colon. 12(a) middle shows that there is reduced vimentin positive cells in Dr3 deficient colon on direct staining in colon sections (FIG. 12a, middle panels), this is important to show that the reduced fibroblast already pre-exist in the colon prior to fibroblast isolation from the colon.

To determine whether the reduction in the number of intestinal fibroblasts and myofibroblasts could be due to direct Tl1a-Dr3 signaling, Dr3 deficient (Dr3−/−) mice were generated. Although there was no spontaneous colitis in either WT or Dr3−/− mice up to 8 weeks of age (FIG. 12a, top panel), there were significantly fewer intestinal fibroblasts in Dr3−/− as compared to WT littermate mice as shown by immunofluorescent staining of vimentin (FIG. 12a, middle panel) and quantitation of the total recovered fibroblasts per colon (FIG. 12a, bottom panel). There were no morphological differences between WT and Dr3−/− fibroblasts by immunofluorescent staining with vimentin and αSMA (FIG. 12a, middle panel) or with light microscopy (FIG. 12a, bottom panel). Ex vivo CellTrace Violet assay and Annexin V stain were used to determine whether the difference in the numbers of intestinal fibroblasts between WT and Dr3−/− mice was due to proliferation and/or apoptosis, respectively. Flow cytometric analysis showed similar rates of proliferation as evidenced by the overlapping CellTrace Violet intensity between WT and Dr3−/− intestinal fibroblasts (FIG. 12b). No differences were observed in the rate of apoptosis between WT and Dr3−/− intestinal fibroblasts (FIG. 12c).

Example 17

Intestinal Fibroblasts Express Dr3 and Respond to TL1A Stimulation

Additional Results

Figure 13:
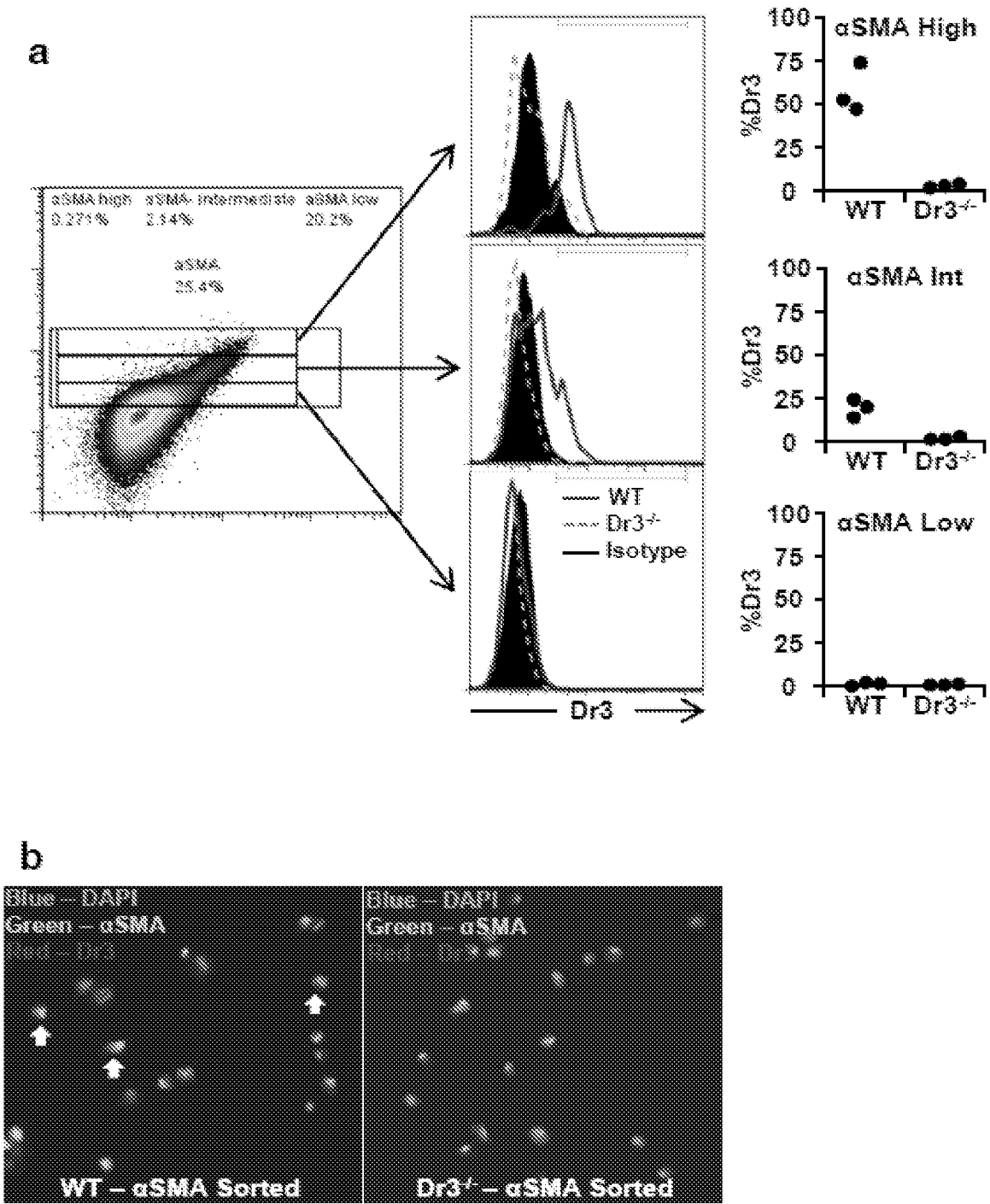
FIG. 13 depicts, in accordance with an embodiment herein, intestinal fibroblasts express Dr3 and respond to Tl1a stimulation. (a) Primary intestinal fibroblasts were stained with Dr3, αSMA and vimentin and analyzed by flow cytometry. Fibroblasts expressing high, intermediate, and low αSMA were gated as shown and Dr3 staining is preferentially found in αSMA high>intermediate>low. Three independent experiments were performed. Specifically.
Figure 13:
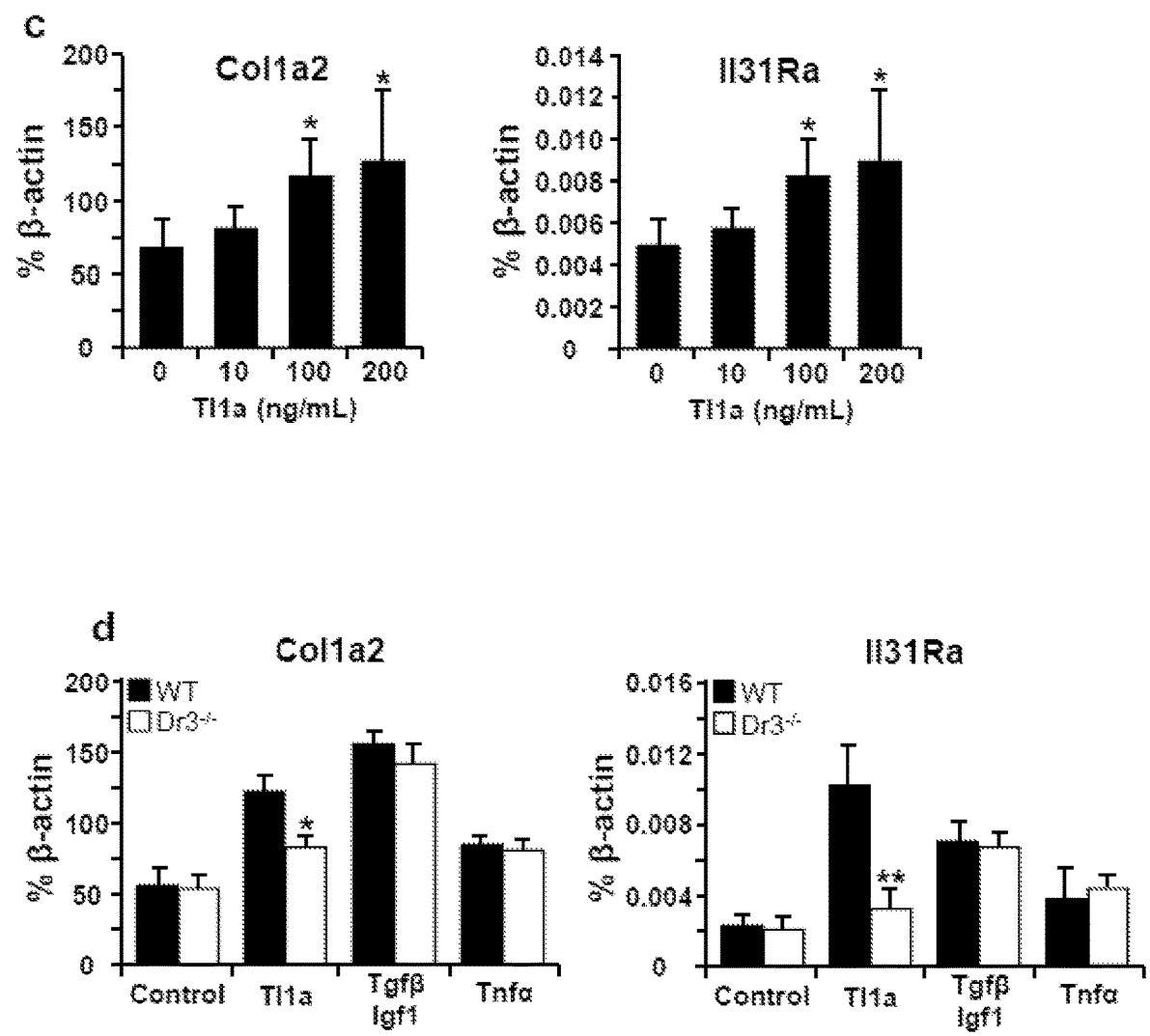

To determine whether intestinal fibroblasts functionally respond to direct Tl1a signaling, mRNA levels of Dr3 were measured and found to be expressed at low levels in WT (0.0018±0.001% β-actin) but undetectable in Dr3 deficient primary intestinal fibroblasts. Flow cytometric analysis was performed to determine whether Dr3 was expressed on vimentin+αSMA− fibroblasts or vimentin+αSMA+ myofibroblasts. The results showed that Dr3 was expressed preferentially on vimentin+αSMA+ myofibroblasts as compared to vimentin+αSMA− fibroblasts. Additionally, there was a direct correlation of Dr3 expression with αSMA levels on myofibroblasts; with a higher proportion of Dr3 expression on myofibroblasts with the highest αSMA expression (FIG. 13a). Additionally, sorted αSMA positive primary intestinal fibroblasts that were immunostained with αSMA and Dr3 showed co-staining of Dr3 in WT but not in Dr3 deficient myofibroblasts, indicating that Dr3 was expressed on αSMA positive primary intestinal fibroblasts (FIG. 13b).

To determine whether intestinal fibroblasts could respond to direct Tl1a stimulation, changes in the expression of collagen (Col1a2, marker for fibroblast function) and Il31Ra (Il31Ra is expressed on fibroblasts) were measured with the addition of exogenous Tl1a protein. Results showed a Tl1a dose-dependent increase in the expression of Col1a2 and Il31Ra in murine primary intestinal fibroblasts ex vivo (FIG. 13c). The specificity of Tl1a stimulation was demonstrated by the blunted Tl1a induction of Col1a2 and Il31Ra in Dr3−/− murine intestinal fibroblasts ex vivo (FIG. 13d). In contrast, a differential induction of Col1a2 or Il31Ra was not seen using known fibroblast growth factors (Tgfβ and Igf1) or proinflammatory stimuli (Tnfα) (FIG. 13d). These data indicated that intestinal fibroblasts expressed Dr3 and could functionally respond to direct Tl1a signaling.

Example 18

Generally

Intestinal fibrostenosis is among the hallmarks of severe Crohn's disease. Patients with certain TNFSF15 (gene name for TL1A) variants over-express TL1A and have a higher risk of developing strictures in the small intestine. Additionally, sustained Tl1a expression in mice leads to small and large intestinal fibrostenosis under colitogenic conditions. The inventors determined whether established murine colonic fibrosis could be reversed with Tl1a antibody. Treatment with neutralizing Tl1a antibody reversed colonic fibrosis back to the original pre-inflamed levels, as result of lowered expression of connective tissue growth factor (Ctgf), Il31Ra, transforming growth factor (Tgf) β1 and insulin-like growth factor-1 (Igf1). Additionally, blocking Tl1a function by either neutralizing Tl1a antibody or deletion of death domain receptor 3 (Dr3) reduced the number of fibroblasts and myofibroblasts, the primary cell types that mediate tissue fibrosis. Primary intestinal myofibroblasts expressed Dr3 and functionally responded to direct Tl1a signaling by increasing collagen and Il31Ra expression. These data demonstrated a direct role for TL1A-DR3 signaling in tissue fibrosis and that modulation of TL1A-DR3 signaling inhibits gut fibrosis.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings.

The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of treating intestinal fibrosis in a subject comprising:
    (a) assaying and detecting a high level of IL31RA in a sample obtained from a subject with intestinal fibrosis, wherein the high level of IL31RA is high as compared to a level of IL31RA in a normal individual;
    (b) administering to the subject in which the high level of IL31RA was detected in (a) a therapeutically effective dosage of one or more inhibitors of TL1A-DR3 binding comprising a blocking TL1A antibody; and
    (c) reducing the high level of IL31RA in the subject, thereby treating the intestinal fibrosis in the subject.

2. The method of claim 1, wherein the one or more inhibitors of TL1A-DR3 binding further comprises one or more DR3 blocking antibodies.

3. The method of claim 1, wherein the one or more inhibitors of TL1A-DR3 binding further comprises an IL31 antibody.

4. The method of claim 1, wherein administering to the subject in which the high level of IL31RA was detected in (a) the therapeutically effective dosage of the one or more inhibitors of TL1A-DR3 binding reverses the intestinal fibrosis in the subject to pre-inflamed levels.

5. The method of claim 1, wherein the intestinal fibrosis is colonic fibrosis.

6. The method of claim 1, wherein administering to the subject in which the high level of IL31RA was detected in (a) the therapeutically effective dosage of the one or more inhibitors of TL1A-DR3 binding inhibits gut inflammation in the subject.

7. The method of claim 1, wherein administering to the subject in which the high level of IL31RA was detected in (a) the therapeutically effective dosage of the one or more inhibitors of TL1A-DR3 binding decreases a number of fibroblasts and/or myofibroblasts in the subject.

8. The method of claim 1, wherein administering to the subject in which the high level of IL31RA was detected in (a) the therapeutically effective dosage of the one or more inhibitors of TL1A-DR3 binding decreases a number of primary intestinal myofibroblasts in the subject.

9. The method of claim 1, wherein the IL31RA is RNA.

10. A method of treating a TL1A associated disease of an intestine in a subject, comprising:
    (a) determining whether a subject with a TL1A associated disease of an intestine has a high level of IL31RA, as compared to a normal individual by:
        (i) obtaining a sample of intestinal tissue from the subject; and
        (ii) assaying the sample to detect a level of IL31RA; and
    (b) if the level of IL31RA detected is high relative to a level of IL31RA in a normal individual, then administering to the subject a therapeutically effective dosage of a blocking TL1A antibody to reduce the level of IL31RA in the subject, thereby treating the TL1A associated disease, wherein the TL1A associated disease comprises Crohn's Disease (CD), Inflammatory Bowel Disease (IBD), strictures in a small intestine, gut inflammation, intestinal fibrostenosis, intestinal fibrosis, or a combination thereof.

11. The method of claim 10, wherein administering to the subject the therapeutically effective dosage of the blocking TL1A antibody decreases a number of fibroblasts and/or myofibroblasts in the subject.

12. The method of claim 10, wherein administering to the subject the therapeutically effective dosage of the blocking TL1A antibody reverses gut inflammation and/or intestinal fibrosis in the subject.

13. The method of claim 10, thereby inhibiting gut inflammation in the subject.

14. The method of claim 10, wherein the IL31RA is RNA.

15. A method of treating intestinal fibrosis in a subject, comprising:
    (a) assaying and detecting a high level of IL31RA a sample obtained from a subject with intestinal fibrosis, wherein the high level of IL31RA is high as compared to a level of IL31RA in a normal individual;
    (b) administering a therapeutically effective dosage of a blocking TL1A antibody and an anti-DR3 antagonist antibody to the subject to reverse the intestinal fibrosis in the subject in which the high level of IL31RA was detected in (a); and
    (c) reducing the high level of IL31RA in the subject.

16. The method of claim 15, comprising decreasing intestinal fibrosis in the subject.

17. A method of reversing intestinal fibrosis in a subject, comprising:
    (a) assaying and detecting a high level of IL3RA in a sample obtained from a subject with intestinal fibrosis, wherein the high level of IL31RA is high as compared to a level of IL31RA in a normal individual;
    (b) administering a therapeutically effective dosage of a blocking TL1A antibody to the subject in which a high level of IL31 RA was detected in (a) to reverse the intestinal fibrosis in the subject; and
    (c) reducing the high level of IL31RA in the subject.

* * * * *